United States Patent [19]
Haselkorn et al.

[11] Patent Number: 5,972,644
[45] Date of Patent: Oct. 26, 1999

[54] CYANOBACTERIAL AND PLANT ACETYL-COA CARBOXYLASE

[75] Inventors: Robert Haselkorn; Piotr Gornicki, both of Chicago, Ill.

[73] Assignee: Arch Development Corporation, Chicago, Ill.

[21] Appl. No.: 08/475,879

[22] Filed: Jun. 7, 1995

Related U.S. Application Data

[62] Division of application No. 07/956,700, Oct. 2, 1992, Pat. No. 5,539,092.

[51] Int. Cl.[6] .............................. C12P 21/06; C12N 5/00; C07H 21/04
[52] U.S. Cl. ................ 435/69.1; 435/252.3; 435/252.33; 435/257.2; 435/320.1; 435/325; 435/419; 536/23.1; 536/23.7; 935/9; 935/67; 935/73
[58] Field of Search ................................. 536/23.7, 23.1; 435/320.1, 69.1, 410, 411, 412, 414, 415, 416, 417, 419, 243, 252.33, 252.3, 257.2, 325; 935/9, 67, 73

[56] References Cited

PUBLICATIONS

L Claesson et al (1983) Proc Natl Acad Sci USA 80:7395–7399.

JD Watson et al (1987) Molecular Biology of the Gene p. 313.

*Primary Examiner*—Bruce R. Campell
*Attorney, Agent, or Firm*—Arnold, White & Durkee

[57] ABSTRACT

The present invention provides isolated and purified polynucleotides that encode plant and cyanobacterial polypeptides that participate in the carboxylation of acetyl-CoA. Isolated cyanobacterial and plant polypeptides that catalyze acetyl-CoA carboxylation are also provided. Processes for altering acetyl-CoA carboxylation, increasing herbicide resistance of plants and identifying herbicide resistant variants of acetyl-CoA carboxylase are also provided.

19 Claims, 18 Drawing Sheets

FIG. 1A

```
ATGCTGGCGTTTATATAGAAAAATTTATTGAACGTCCGGCCACATTGAATTTCAAATTTGGCTGATAATTACGGCAATGTGATTCACT    1980
 M  L  A  F  I  *                                                                         
                  A  G  V  Y  I  E  K  F  I  E  R  P  R  H  I  E  F  Q  I  L  A  D  N  Y  G  N  V  I  H  L
TGGGTGAGAGGGATTGCTCAATTCAGCGTCGTAACCAAAAGTTACTAGAGAAGAAGCCCCCAGCCTTGGACTCAGACCTAAGGGAAA    2070
 G  E  R  D  C  S  I  Q  R  N  Q  K  L  L  E  E  A  P  S  P  A  L  D  S  D  L  R  E  K
AAATGGGACAAGCGCGGTGAAAGCGGCTCAGTTCATCAATTACGCCGGGGCAGGTACTATCGAGTTTTTGCTAGATAGATCCGGTCAGT    2160
 M  G  Q  A  A  V  K  A  A  Q  F  I  N  Y  A  G  T  I  E  F  L  L  D  R  S  G  Q  F
TTTACTTTATGGAGAGATGAACACCCGGATTCAAGTAGAACATCCCGTAACTGAGATGGTTACTGGAGATGGATTTATTGGTTGAGCAAATCA    2250
 F  Y  F  M  E  M  N  T  R  I  Q  V  E  H  P  V  T  E  M  V  T  G  V  D  L  L  V  E  Q  I  R
GAATTGCCAAGGGGAAAGACTTAGACTAACTCAAGACCAAGTAGTTTTACGCGGTCATGCGGATCGAATGTCGCATCCCACGTTACA    2340
 I  A  Q  G  E  R  L  R  L  T  Q  D  Q  V  V  L  R  G  H  A  I  E  C  R  I  N  A  E  D  P
CAGACCACGATTTCCGCCCAGCACCCGGACGCATTAGCGGTTATCTTCCCCCTGGCGGCCGTGCGGATTGACTCCCACGTTTACA    2430
 D  H  D  F  R  P  A  P  G  R  I  S  G  Y  L  P  P  G  G  P  G  V  R  I  D  S  H  V  Y  T
CGGATTACCAAAATTCCGCTACTAGTTGATCGTTGGGAATGGTAAATTGGTAAATTGATCGTTGGGTCTATTAACGCATGA    2520
 D  Y  Q  I  P  P  Y  Y  D  S  L  I  G  K  L  I  V  G  P  D  R  A  T  A  I  N  R  M  K
AACGCGCCCCTCAGGGAATGCGCCAACATGCAGGAGATGAATAAATAGGGTAAGAATTATGGAAGAATTATGAAGAATTTACAAG    2610
 R  A  L  R  E  C  A  I  T  G  L  P  T  T  I  G  F  H  Q  R  I  M  E  N  P  Q  F  L  Q  G
GTAATGTGTCTACTAGTTTGTGCAGGAGATGAATAAATAGGGTAAGTGAATAGAGTTTCAATCACCAATTACC    2700
 V  M  C  L  L  V  C  R  R  *        W  V  M  G  N  R  V  S  I  T  N  Y  Q
                                        * W V M G N R V S I T N Y Q
GTAATGTGTCTACTAGTTTGTGCAGGAGATGAATAAATAGGGTAAGTGAATAGAGTTTCAATCACCAATTACC
 N  V  S  T  S  F  V  Q  E  M  N  K  *        W  V  M  G  N  R  V  S  I  T  N  Y  Q
AATTCCCTAACTCATCCGTCGCCAACATCGTCAGTAATCCTTGCTGGCCTAGAAGAACTTCTCGCAACAGGCTAAAAATACCAACACACAC    2790
 F  P  N  S  S  V  P  T  S  S  V  I  L  A  G  L  E  E  L  L  A  T  G  *

AATGGGGGTGATATCAACACCACCTATTGGTGGGATGATTTTCGCAAGGGAATGAGAAATGGTTCAGTCGGCAAGCAATTAAGTTGAA    2880
GGGCAAACGGTTCAGATCGACGTTGCCGATACCAGGTCAGAATGATACGGAAGAAATAAACAGAAATGTCATCACTCCAATACAGGGCCAAG    2970
AATCCAAACGCTCAGGTTAACACCAGTCATCGATCTAAGCTACTATTTTGTGAATTTACAAAAAACTGCAAGCAAAGCTGAAAATTTTA    3060
AGCTT                                                                                      3065
```

FIG. 1B

ATGCGTTTCA ACAAGATCCT GATCGCCAAT CGCGGCGAAA TCGCCCTGCG CATTCTCCGC

ACTTGTCAAG AACTCGGGAT CGGCACGATC GCCGTTCACT CCACTGTGGA TCGCAACGCG

CTCCATGTGC AGTTAGCGGA CGAAGCGGTC TGTATTGGCG AAGCGGCCAG CAGCAAAAGC

TATCTCAATA TCCCCAACAT CATTGCGGCG GCCCTGACCC CTAATGCCAG CGCCATTCAC

CCCGGCTATG GCTTCTTGGC GGAGAATGCC CGCTTTGCAG AAATCTGCGC CGATCACCAT

CTCACCTTTA TTGGCCCCAG CCCCGATTCG ATTCGAGCCA TGGGCGATAA ATCCACCGCT

AAGGAAACAA TGCAGCGGGT CGGCGTTCCG ACGATTCCGG GCAGTGACGG TCTGCTGACG

GATGTTGATT CGGCTGCCAA AGTTGCTGCC GAGATCGGCT ATCCCGTCAT GATCAAAGCG

ACGGCGGGGG GCGGTGGTCG CGGTATGCGG CTGGTGCGTG ACCCTGCAGA TCTGGAAAAA

CTGTTCCTTG CTGCCCAAGG AGAAGCCGAG GCAGCTTTTG GGAATCCAGG ACTGTATCTC

GAAAAATTTA TCGATCGCCC ACGCCACGTT GAATTTCAGA TCTTGGCCGA TGCCTACGGC

AATGTAGTGC ATCTAGGCGA GCGCGATTGC TCCATTCAAC GTCGTCACCA AAAGCTGCTC

GAAGAAGCCC CCAGTCCGGC GCTATCGGCA GACCTGCGGC AGAAAATGGG CGATGCCGCC

GTCAAAGTCG CTCAAGCGAT CGGCTACATC GGTGCCGGCA CCGTGGAGTT TCTGGTCGAT

GCGACCGGCA ACTTCTACTT CATGGAGATG AATACCCGCA TCCAAGTCGA GCATCCAGTC

ACAGAAATGA TTACGGGACT GGACTTGATT GCGGAGCAGA TTCGGATTGC CCAAGGCGAA

GCGCTGCGCT TCCGGCAAGC CGATATTCAA CTGCGCGGCC ATGCGATCGA ATGCCGTATC

AATGCGGAAG ATCCGGAATA CAATTTCCGG CCGAATCCTG GCCGCATTAC AGGCTATTTA

CCGCCCGGCG GCCCCGGCGT TCGTGTCGAT TCCCATGTTT ATACCGACTA CGAAATTCCG

CCCTATTACG ATTCGCTGAT TGGCAAATTG ATTGTCTGGG GTGCAACACG GGAAGAGGCG

ATCGCGCGGA TGCAGCGTGC TCTGCGGGAA TGCGCCATCA CCGGCTTGCC GACGACCCTT

AGTTTCCATC AGCTGATGTT GCAGATGCCT GAGTTCCTGC GCGGGGAACT CTATACCAAC

FIG. 2A

TTTGTTGAGC AGGTGATGCT ACCTCGGATC CTCAAGTCCT AG amino acid sequence

MRFNKILIAN RGEIALRILR TCEELGIGTI AVHSTVDRNA LHVQLADEAV CIGEAASSKS

YLNIPNIIAA ALTRNASAIH PGYGFLAENA RFAEICADHH LTFIGPSPDS IRAMGDKSTA

KETMQRVGVP TIPGSDGLLT DVDSAADVAA EIGYPVMIKA TAGGGGRGMR LVREPADLEK

LFLAAQGEAE AAFGNPGLYL EKFIDRPRHV EFQILADAYG NVVELGERDC SIQRRHQKLL

EEAPSPALSA DLRQKMGDAA VKVAQAIGYI GAGTVEFLVD ATGNFYFMEM NTRIQVEHPV

TEMITGLDLI AEQIRIAQGE ALRFRQADIQ LRGHAIECRI NAEDPEYNFR PNPGRITGYL

PPGGPGVRVD SHVYTDYEIP PYYDSLIGKL IVWGATREEA IARMQRALRE CAITGLPTTL

SFHQLMLQMP EFLRGELYTN FVEQVMLPRI LKS

FIG. 2B

```
                                                                                     70
Wh ACC    ...............................................................
Rt ACC    MDEPSPLAKTLELNQHSRFIIGSVSEDNSEDEIS-NLVKLDLEEKEGSLSPASVSSDTLSDLGISALQDG
Ch ACC    MEESSQPAKPLEMNPHSRFIIGSVSEDNSEDETSSLVKLDLLEEKERSLSPVSVCSDSLSDLGLPSAQDG
Yt ACC    .........................................................MSEESLFESSP
Sy ACC    ......................................................................
An ACC    ......................................................................
Ec ACC    ......................................................................
Hm PCCA   ......................................................................
Rt PCCA   ...................................................MPYRERFC..........
Yt PC     ......................................................................

140
Wh ACC    ......................................................................
Rt ACC    LAFHMRSSMSGLHLVKQGRKRKKIDSQRDFTVASPAEFVTRFGGNKVIEKVLIANNGIAABKCMRSIRRW
Ch ACC    LANHMRPSMSGLHLVKQGRDRKKVDQRDFTVASPAEFVTRFGGNRVIEKVLIANNGIAAVKCMRSIRRW
Yt ACC    QKMEYEITNYSERHTELPGHFIGLNTVDKLEESPLRDFVKSHGGHTVISKILIANNGIAAVKEIRSVRKW
Sy ACC                                                    MRFNKILIANRGEIALRILRTCEEL
An ACC                                                    MKRFKILIANRGEIALRILRACEEM
Ec ACC                                                     MLDKIVIANRGEIALRILRACKEL
Hm PCCA        MLSAALRTLKHVLYYSRQCLMVSRNLGSVGYDPNEKTFDKILVANRGEIACRVIRTCKKM
Rt PCCA   AIRWCRNSGRSSQQLLWTLKRAPVYSQQCLVVSRSLSSVEYEPKEKTFDKILIANRGEIACRVIKTCRKM
Yt PC               MSQRKFAGLRDNFNLLGEK-NKILVANRGEIPIRIFRTAHEL
                                        *   * ** *
```

FIG. 3A

```
                                                                                        210
Wh ACC   ..........................................................................
Rt ACC   SYEMFRNERAIRFVVMVTPEDLKANAEYIKMADHYVPVPGGANNNNYANVELILDIAKRIPVQAVWAGWG
Ch ACC   SYEMFRNERAIRFVVMVTPEDLKANAEYIKMADHYVPVPGGPNNNNYANVELILDIAKRIPVQAVWAGWG
Yt ACC   AYETFGDDRTVQFVAMATPEDLEANAEYIRMADQYIEVPGGTNNNNYANVDLIVDIAERADVDAVWAGWG
Sy ACC   GIGTIAVHSTVD--RNALHVQLADEAVCIGEAASS---------KSYLNIPNIIAAALTRNASAIHPGTG
An ACC   GIATIAVHSTVD--RNALHVQLADEAVCIGEPASA---------KSYLNIPNIIAAALTRNASAIHPGYG
Ec ACC   GIKTVAVHSSAD--RDLKHVLLADETVCIGPAPSV---------KSYLNIPAIISAAEITGAVAIHPGYG
Hm PCCA  GIKTVAIHSDVD--ASSVHKMADEAVCGPAPTS-----------KSYLNMDAIMEAIKKTRAQAVHPGYG
Rt PCCA  GIRTVAIHSDVD--ASSVHKMADEAVCGPAPTS-----------KSYLNMDAIMEAIKKTGAQAVHPGYG
Yt PC    SMQTVAIYSHED--RLSTHKQKADEAYVIGEVGQYTPV------GAYLAIDEIISIAQKHQVDFIHPGYG
                                             *                *                *  *

280
Wh ACC   ..........................................................................
Rt ACC   HASENPKLPELL--LKNGIAFMGPPSQAMWALGDKIASSIVAQTAGIPTLPWSGSGLRVDWQENDFSKRI
Ch ACC   HASENPKLPELL--HKNGIAFMGPPSQAMWALGDKIASSIVAQTAGIPTLPWNGSGLRVDWQENDLQKRI
Yt ACC   HASENPLLPEKLSQSKRKVIFIGPPGNAMRSLGDKISSTIVAQSAKVPCIPWSGTGVDTVH--VDEKTGL
Sy ACC   FLAENARFAEIC--ADHHLTFIGPSPDSIRAMGDKSTAKETMQRVGVPTIPGSDG-L-------------
An ACC   FLSENAKFAEIC--ADHHIAFIGPTPEAIRLMGDKSTAKETMQKAGVPTCPGSEG-L-------------
Ec ACC   FLSENANFAEQV--ERSGFIFIGPKAETIRLMGDKVSAIAAMKKAGVPCVPGSDGPL-------------
Hm PCCA  FLSENKEFARCL--AAEDVVFIGPDTHAIQAMGDKIESKLLAKKAEVNTIPGFDG-V-------------
Rt PCCA  FLSENKEFAKCL--AAEDVTFIGPDTHAIQAMGDKIESKLLAKRAKVNTIPGFDG-V-------------
Yt PC    FLSENSEFADKV--VKAGITWIGPPAEVIDSVGDKVSARNLAAKANVPTVPGTPG-P-------------
         ***              ***           *     **            *
```

FIG. 3B

```
Wh ACC  ..........................VMIKASWGGGGKGIRKVHNDDEVRALFKQVQGEVPGS----  350
Rt ACC  LNVPQDLYEKGYVKDVDDGLKAAEEVGYPVMIKASEGGGGKGIRKVHNDDEVRALFKQVQGEVPGS----
Ch ACC  LNVPQELYEKGYVKDADDGLRAAEEVGYPVMIKASEGGGGKGIRKVNNADDFPNLFRQVQAEVPGS----
Yt ACC  VSVDDDIYQKGCCTSPEDGLQKAKRIGFPVMIKASEGGGGKGIRQVEREEDFIALYHQAANEIPGS----
Sy ACC  ----------------LTDVDSAAKVAAEIGYPVMIKATAGGGGRGMRLVREPADLEKLFLAAQGEAEAAFGNP
An ACC  ----------------VETEQEGLELAKDIGYPVMIKATAGGGGRGMRLVRSPDEFVKLFLAAQGEAGAAFGNA
Ec ACC  ----------------GDDMDKNRAIAKRIGYPVIIKASGGGGRGMRVVRGDAELAQSISMTRAEAKAAFSND
Hm PCCA ----------------VKDAEEAVRIAREIGYPVMIKASAGGGGKGMRIAWDDEETRDGFRLSSQEAASSFGDD
Rt PCCA ----------------LKDADEAVRIAREIGYPVMIKASAGGGGKGMRIPWDDEETRDGFRFSSQEAASSFGDD
Yt PC   ----------------IETVEEALDFVNEYGYPVIIKAAFGGGGRGMRVVREGDDVADAFQRATSEARTAFGNG
                         ****  *** ****** *  ****           *

Wh ACC  PIFIMKVASQSRHLEVQLLCDKHGNVAALHSRDCSVQRRHQKIIEEGPITVAPPETIKELEQAARRLAKC   420
Rt ACC  PIFVMRLAKQSRHLEVQILADQYGNAISLFGRDCSVQRRHQKIIEEAPAAIATPAVFEHMEQCAVKLAKM
Ch ACC  PIFVMRLAKQSRHLEVQILADQYGNAISLFGRDCSGQRRHQKIIEEAPASIATSVVFEHMEQCAVKLAKM
Yt ACC  PIFIMKLAGRARHLEVQLLADQYGTNISLFGRDCSVQRRHQKIIEEAPVTIAKAETFHEMEKAAVRLGKL
Sy ACC  GLYLEKFIDRPRHVEFQILADAYGNVVHLGERDCSIQRRHQKLLEEAPSPALSADLRQKMGDAAVKVAQA
An ACC  GVYIEKFIERPRHIEFQILADNYGNVIHLGERDCSIQRRNQKLLEEAPSPALDSDLREKMGQAAVKAAQF
Ec ACC  MVYMEKYLENPRHVEIQVLADGQGNAIYLAERDCSMQRRHQKVVEEAPAPGITPELRRYIGERCAKACVD
Hm PCCA RLLIEKFIDNPRHIEIQVLGDKHGNALWLNERECSIQRRNQKVVEEAPSIFLDAETRRAMGEQAVALARA
Rt PCCA RLLIEKFIDNPRHIEIQVLGDKHGNALWLNERECSIQRRNQKVVEEAPSIFLDPETRRAMGEQAVAWPKA
Yt PC   TCFVERFLDKPKHIEVQLLADNHGNVVHLFERDCSVQRRHQKVVEVAPAKTLPREVRDAILTDAVKLAKE
          *   *     * ***  *   **  *   *   ****  **  *
```

FIG. 3C

```
Wh ACC    VQYQGAATVEYLYSMETGEYYFLELNPRLQVEHPVTEWIAEINLPASQVVVGMGIPLYNIPEIRRFYGIE  490
Rt ACC    VGYVSAGTVEYLYSQD-GSFYFLELNPRLQVEHPCTEMVADVNLPAAQLQIAMGIPLFRIKDIRMYGVS
Ch ACC    VGYVSAGTVEYLYSQD-GSFYFLELNPRLQVEHPCTEMVADVNLPAAQLQIAMGIPLHRIKDIRVMGVS
Yt ACC    VGYVSAGTVEYLYSHDDGKFYFLELNPRLQVEHPTTEMVSGVNLPAAQLQIAMGIPMHRISDIRTLYGMN
Sy ACC    IGYIGAGTVEFLVD-ATGNFYFMEMNTRIQVEHPVTEMITGLDLIAEQIRIAQGEALRFRQADIQ-----
An ACC    INYAGAGTIEFLLD-RSGQFYFMEMNTRIQVEHPVTEMTGVDLVEQIRIAQGERLRLTQDQVV-------
Ec ACC    IGYRGAGTFEFLF--ENGEFYFIEMNTRIQVEHPVTEMITGVDLIKEQMRIAAGQPLSIKQEEVH-----
Hm PCCA   VKYSSAGTVEFLVDSK-KNFYFLEMNTRLQVEHPVTECIHWPGPSPGKTVLQEHLSGTNKLIFA------
Rt PCCA   VKYSSAGTVEFLVDSQ-KNFYFLEMNTRLQVEHPVTECITGLDLVQEMILVAKGYPLRHKQEDIP-----
Yt PC     CGYRNAGTAEFLVDNQ-NRHYFIEINPRIQVEHTITEEITGIDIVAAQIQIAAGASLPQLGLFQDKIT--
             *   ***  *        *   *  **  * *   *  *                 ****** **

Wh ACC    HGGGYHAWKEISAVATKFDLDKAQSVKPKGHCVAVRVTSEDPDDGFK-PTSGRVEELNFKSKPNVWAYF-  560
Rt ACC    PWGDAPIDFENSAHVPC---------PRGHVIAARITSENPDEGFK-PSSGTVQELNFRSNKNVWGYF-
Ch ACC    PWGDGSIDFENSAHVPC---------PRGHVIAARITSENPDEGFK-PSSGTVQELNFRSNKNVWGYF-
Yt ACC    PHSASEIDFEFKTQDAT---KKQRRPIPKGHCTACRITSEDPNDGFK-PSGGTLHELNFRSSSNVWGYG-
Sy ACC    ------------------------------LRGHAIECRINAEDPEYNF-RPNPGRITG--YLPPGG-PGVRV
An ACC    ------------------------------LRGHAIECRINAEDPDHDF-RPAPGRISG--YLPPGG-PGVRI
Ec ACC    ------------------------------VRGHAVECRINAEDPN-TF-LPSPGKITR-FHAPGG-FGVRW
Hm PCCA   ------------------------------FNGWAVECRVYAEDPYKSFGLPSIGRLSQ--YQEPLHLPGCRV
Rt PCCA   ------------------------------ISGWAVECRVYAEDPYKSFGLPSIGRLSQ--YQEPIHLPGVRV
Yt PC     ------------------------------TRGFAIQCRITTEDPAKNFQ-PDTGRIEV--YRSAGG-NGVRL
                                            *       *    *       *              *
```

FIG. 3D

```
Wh ACC    ---SVKSGGAIHEFSDSQFGHVFAFGESRSLAIANMVLGLKEIQIRGEIRTNVDYTVDLLNAAEYRENMI  630
Rt ACC    ---SVAAAGGLHEFADSQFGHCFSWGENREEAISNMVALKELSIRGDGRTTVEYLIKLLETESFQLNRI
Ch ACC    ---SVAAAGGLHEFADSQFGHCFSWGENREEAISNMVALKELSIRGDFRTTVEYLIKLLETESFQQNRI
Yt ACC    ---SVGNNGNIHSFSDSQFGHIFAFGENRQASRKHMVALKELSIRGDFRTTVEYLIKLLETEDFEDNTI
Sy ACC    DS-HVYTDYEIPPYYDSLIGKLIVWGATREEAIARMQRALRECAITG-LPTTLSFHQLMLQMPEFLRGEL
An ACC    DS-HVYTDYQIPPYYDSLIFKLIVWGPDRATAINRMRKALRECAITG-LPTTIGFHQRIMENPQFLQGNV
Ec ACC    ES-HIYAGYTVPPYYDSMIGKLICYGENRDVAIARMKNALQELIIDG-IKTNVDLQIRIMNDENFQHGGT
Hm PCCA   DS-GIQPGSDISIYDPMISKLITYGSDRTEALKRMADALDNYVIRG-VTHNIALLREVIINSRFVKGDI
Rt PCCA   DS-GIQPGSDISIYHDPMISKLVTYGSDRAEALKRMEDALDSYVIRG-VTHNIPLLREVIINTRFVKGDI
Yt PC     DGGNAYAGTIISPHYDSMLVKCSCSGSTYEIVRRKMIRALIEFRIRG-VKTNIPFLLTLLTNPVFIEGTY
                *                             *      **   *  *  **  *

Wh ACC    HTGWLDSRIAMRVRAERPPWYLSVVGGALYEASSRSSSSVVTDYVGYLSKGQIPPK------------ 700
Rt ACC    DTGWLDRLIAEKVQAERPDTMLGVVCGALHCADVNLRNSISNGLHSLERGQVLPA-------------
Ch ACC    DTGWLDRLIAEKVQAERPDTMLGVVCGALHVADVSFRNSVSNFLHSLERGQVLPA-------------
Yt ACC    TTGWLDDLITHKMTAEKPDPTLAVICGAATKAFLASEEARHKYIESLQKGQVLSK-------------
Sy ACC    YTNFVEQVMLPRILKS
An ACC    STSFVQEMNK
Ec ACC    NIHYLEKKLGLQEK
Hm PCCA   STKFLSDVYPDGFKGHMLTKSEKNQLLAIASSLFVAFQLRAQHFQENSRMPVIKPDIANWELSVKLHDKV
Rt PCCA   STKFLSDVYPDGFKGHMLTPSERDQLLAIASSLFVASQLRAQRFQEHSRVPVIRPDVAKWELSVKLHDED
Yt PC     WGTFIDDTPQLFQMVSSQNRAQKLLHYLADVADNGSSIKGQIGLPKLKSNPSVPH-#-SYNMYPRVYEDF
Kp ODA                                                              -##-NAIDDVLTVAL
```

```
Wh ACC   --HISLVNLTVTLNIDGSKYTIETVRGGPRSYKLRINESEVEAEIHFLRDGGLLMQLDGNSHVIYAETEA 770
Rt ACC   --HTLLNTVDVELIYEGIKYVLKVTRQSPNSYVVIMNGSCVEVDVHRLSDGGLLLSYDGSSYTTYMKEEV
Ch ACC   --HTLLNTVDVELIYEGRKYVLKVTRQSPNSYVVIMNSSCVEVDVHRLSDGGLLLSYDGSSYTTYMKEEV
Yt ACC   --DLLQTMFPVDFIHEGKRYKFTVAKSGNDRYTLFINGSKCDIILRQLSDGGLLIAIGGKSHTIYWKEEV
An ACC   TLKSDDFELTVRKAVGVNNSVVPVVTAPLSGVVGSGLPSAIPIVAHAAPSPSPEPGTSRAADHAVTSSGS
Ec ACC   MDIRKIKKLIELVEESGISELEISEGEESVRISRAAPAASFPVMQQAYAAPMMQQPAQSNAAAPATVPS
Hm PCCA  HTVASNNGSVFSVEVDGSKLNVTSTWNLASPLLSVSVDGTQRTVQCLSREAGGNMSIQFLGTVYKVNIL
Rt PCCA  HTVASNNGPTFNVEVDGSKLNVTSTWNLASPLLSVNVDGTQRTVQCLSPDAGGNMSIQFLGTVYKVHIL
Yt PC    QKMRETYGDLSVLPTRSFLSPLETDEEIEVVIEQGKTLIIKLQAVGDLNKKTGEREVYFDLNGEMRKIRV
Kp ODA   FPQPGLKFLENRHNPAAFEPVPQAEAAQPVAKAEKPAASGVYTVEVEGKAFVVKVSDGGDVSQLTAAAPA
Ps TC                                            MKLKVTVNGTAYDVDVDVDKSHENPMGTILFGGG

Wh ACC   AGTRLLINGRTCLLQKEHDPSRLLADTPCKLLRFLVADGSHVVADTPYAEVEAMKM.............. 840
Rt ACC   DRYRITIGNKTCVFEKENDPSVMRSPSAGKLIQYIVEDGGHVFAGQCYAEIEVMKMVMTLTAVESGCIHY
Ch ACC   DRYRITIGNKTCVFEKENDPSILRSPSAGKLIQYVVEDGGHVFAGQCFAEIEVMKMVMTLAGESGCIHY
Yt ACC   AATRLSVDSMTTLLEVENDPTQLRTPSPGKLVKFLVENGEHIIKGQPYAEIEVMKMQMPLVSQENGIVQL
An ACC   QPGAKIIDQKLAEVASPMVGTFYRAPAGE--AVFVEVGDRIRQGQTVCIIEAMKM..............
Ec ACC   MEAPAAAEISGHIVRSPMVGTFYRTPSPDA--KAFIEVGQKVNVGDTLCIVEAMKMMNQIEADKSGTVKA
Hm PCCA  TRLAAELNKFMLEKVTEDTSSVLRSPMPGVVVAVSVKPGDAVAEGQEICVIEAMKMQNSMTAGKTGTVKS
Rt PCCA  TKLAAWLNKFMLEKVPKDTSSVLRSPKPGVVVAVSVKPGDMVAEGQEICVIEAMKMQNSMTAGKMGKVKL
Yt PC    ADRSQKVETVTKSKADMHDPLHIGAPMAGVIVEVKVHKGSLIKKGQPVAVLSAMKMEMIISSPSDGQVKE
Kp ODA   PAPAPASAPAAAAPAGAGTPVTAPLAGTVSKILVKEGDTVKAGQTVLVLEAMKMETEINAPTDGKVEK
Ps TC    TGGAPAPRAAGGAGGAGEGEIPAPLAGTVSKILVKEGDTVKAGQTVLVLEAMKMETEINAPTDGKVEK
                *                   *              *         *  *      ***
```

```
Wh ACC    ........................................ 900
Rt ACC    ......VKRPGAALDPGCVIAKMALDNPSKVQQAELHTGSLPQIQSTALRGEKLHRIF
Ch ACC    VKRPGAVLDPGCVIAKLQLDDPSRVQQAELHTGTLPQIQSTALRGEKLHRIF
Yt ACC    LKQPGSTIVAGDIMAIMTLDDPSKVKHALPFEGMLPDFGSPVIEGTKPAYKF
An ACC    ...................................
Ec ACC    ILVESGQPVEFDEPLVVIE
Hm PCCA   VHCQAGDTVGEGDLLVELE
Rt PCCA   VHCKAGDTVGEGDLLVELE
Yt PC     VFVSDGENVDSSDLLVLLEDQVPVETKA
Kp ODA    IAVKAGDAVAVGDTLMTLA
PS TC     VLVKERDAVQGGQGLIKIG
          ------------------
```

FIG. 3G

```
GTGATGATCAAGGCATCATGGGGTGTGGGGTGGTAAAGGAATAAGGAAGGTACATAATGATGAGGTCAGAGCATTGTTAAGCAAGTG    90
 V  M  I  K  A  S  W  G  G  G  G  K  G  I  R  K  V  H  N  D  D  E  V  R  A  L  F  K  Q  V

CAAGGAGAAGTCCCCGGATGCCTATATTTATTGAAGGTGGCATCTCAGAGTGGACATCTAGAGGTTCAATTGTCTCTGACAAGCAT   180
 Q  G  E  V  P  G  S  P  I  F  I  M  K  V  A  S  Q  S  R  H  L  E  V  Q  L  L  C  D  K  H

GGCAACGTGGCAGCACTGCACACTGAGACTGTAGTGTTCAAAGAAGGCATCAAAGATCATTGAGGAGGGACCAATTACAGTTGCTCCT   270
 G  N  V  A  A  L  H  S  R  D  C  S  V  Q  R  R  H  Q  K  I  I  E  E  G  P  I  T  V  A  P

CCAGAAACAATTAAAGAGCTTGAGCAGGCGGCAAGGCGACTAGCTAAATGTGTGCAATATCAGGGTGCTGCTACAGTGGAATATCTGTAC   360
 P  E  T  I  K  E  L  E  Q  A  A  R  R  L  A  K  C  V  Q  Y  Q  G  A  A  T  V  E  Y  L  Y

AGCATGGAAAACAGGCGAATACTATTCCTGGAGCTTAATCCAAGGTTGCAGGTAGAACACCCTGTGACCGAATGGATTGCTGAAATAAAC   450
 S  M  E  T  G  E  Y  Y  F  L  E  L  N  P  R  L  Q  V  E  H  P  V  T  E  W  I  A  E  I  N
                                   C
                                   T

TTACCTGCATCTCAAGTTGTAGTAGGAATGGGCATACCACTCTACAACATTCCAGAGATCAGAGCGCTTTTATGGAATAGAACATGGAGGT   540
 L  P  A  S  Q  V  V  V  G  M  G  I  P  L  Y  N  I  P  E  I  R  R  F  Y  G  I  E  H  G  G
                                                                   C           G
                                                                   C           G

GGCTATCATGCTTGGAAGGAAATATCAGCTGTTGCAACTAAATTTGATTGGACAAAGCACAGTCTGTAAAGCCAAAAGGTCATTGTGTA   630
 G  Y  H  A  W  K  E  I  S  A  V  A  T  K  F  D  L  D  K  A  Q  S  V  K  P  K  G  H  C  V
```

FIG. 6A

```
                                                                          A                    G
                                                                          A                    G
GCAGTTAGAGAGTTACTAGGCGAGGATCCAGATGATGGGTTTAAGCCTACCAGTGGAAGAGTAGAAGAGCTGAACTTTAAAAGTAAACCCAAT  720
 A  V  R  V  T  S  E  D  P  D  D  G  F  K  P  T  S  G  R  V  E  E  L  N  F  K  S  K  P  N

C     G                  C                                         C
                         T     A                  T                                         T
GTTTGGGCCTATTTCTCCGTTAAGTCCGGAGGTGCAATTCACGAGTTCTCTGATTCCCAGTTTGGTCATGTTTTTGCTTTTGGGGAATCT     810
                                                                     S
 V  W  A  Y  F  S  V  K  S  G  G  A  I  H  E  F  S  D  S  Q  F  G  H  V  F  A  F  G  E  S
                                    R
 T
 A
                                                                                T     C
                                                                                A     T
AGGTCATTGGCAATAGCCAATATGGTACTTGGGGTTAAAAGAGATCCAAATTCGTGGAGAGATACGCACTAATGTTGACTACACTGTGGAT    900
 R  S  L  A  I  A  N  M  V  L  G  L  K  E  I  Q  I  R  G  E  I  R  T  N  V  D  Y  T  V  D

A
                        A
CTCTTGAATGCTGCAGAGTACCGAGAAAATATGATTCACACTGGTTGGCTAGACAGCAGAATAGCTATGCGCGTTAGAGCAGAGAGGCCC    990
                        K
 L  L  N  A  A  E  Y  R  E  N  M  I  H  T  G  W  L  D  S  R  I  A  M  R  V  R  A  E  R  P

CCATGGTACCTTTCAGTTGTTGGTGGAGCTCTATATGAAGCATCAAGCAGGAGCTCGAGTGTTGTAACCGATTATGTTGGTTATCTCAGT   1080
 P  W  Y  L  S  V  V  G  G  A  L  Y  E  A  S  S  R  S  S  S  V  V  T  D  Y  V  G  Y  L  S
```

FIG. 6B

```
                                              C
                                              T
AAAGGTCAAATACCACCAAAGCACATCTCTCTTGTCAATTTGACTGTAACACTGAATATAGATGGGAGCAAATATACGATTGAGACAGTA  1170
 K  G  Q  I  P  P  K  H  I  S  L  V  N  L  T  V  T  L  N  I  D  G  S  K  Y  T  I  E  T  V
             A         CG                      C                   A

CG                                      T
CGAGGTGGACCCCGTAGCTACAAATTAAGAATTAATGAATCAGAGGTTGAGGCAGAGATACATTCCTGCGAGATGGCGGACTCTTAATG  1260
 R  G  G  P  R  S  Y  K  L  R  I  N  E  S  E  V  E  A  E  I  H  F  L  R  D  G  G  L  L  M
       T                                             G                    S            P
       C                                             T

CAGTTGGATGGAAACAGTCATGTAATTTACGCCGAGACAGAAGCTGCTGGCACGCGCCTTCTAATCAATGGGAGAACATGTTATTACAG  1350
 Q  L  D  G  N  S  H  V  I  Y  A  E  T  E  A  A  G  T  R  L  L  I  N  G  R  T  C  L  L  Q
    S                                                S                      A
                                                                            G

T                                              A
                                     T                                              G
AAAGAGCACGATCCTTCCAGGTTGTTGGCTGATACACCGTGCAAACTTCTTCGGTTTTTGGTCGGCGGATGGTTCTCATGTGGTTGCTGAT  1440
 K  E  H  D  P  S  R  L  L  A  D  T  P  C  K  L  L  R  F  L  V  A  D  G  S  H  V  V  A  D
          T                                                                  S

ACGCCATATGCCGAGGTGGAGGCCATGAAAAATG
 T  P  Y  A  E  V  E  A  M  K  M
```

FIG. 6C

```
TCTAGACTTTAACGAGATTCGTCAACTGCTGACAACTATTGCACAAACAGATATCGCGGAAGTAACGCTCAAAAGTGATGATTTGAACT    90
 L  D  F  N  E  I  R  Q  L  L  T  T  I  A  Q  T  D  I  A  E  V  T  L  K  S  D  D  F  E  L

AACGGTGCGTAAAGCTGTTGGTGTGTGAATAATAGTGTTGTGCCGGTTGTGACAGCACCCTTGAGTGGTGTGTAGGTTCGGGATTGCCATC   180
 T  V  R  K  A  V  G  V  N  N  S  V  V  P  V  V  T  A  P  L  S  G  V  V  G  S  G  L  P  S

GGCTATACCGATTGTAGCCCATGCTGCCCCATCTCCAGAGCCGGGAACAAGCCGTGCTGCTGATCATGCTGTCACGAGTTCTGG          270
 A  I  P  I  V  A  H  A  A  P  S  P  E  P  G  T  S  R  A  A  D  H  A  V  T  S  S  G

CTCACAGCCAGGAGCAAAAATCATTGACCAAAATTAGCAGAAGTGGCTTCCCCAATGTGGGAACATTTTACCGCGCTCCTGCACCAGG      360
 S  Q  P  G  A  K  I  I  D  Q  K  L  A  E  V  A  S  P  M  V  G  T  F  Y  R  A  P  A  P  G

TGAAGCGGTATTTGTGGAAGTCGGCGATCGCATCCGTCAAGGTCAAACCGTCTGCATCATCGAAGCGATGAAAAUG
 E  A  V  F  V  E  V  G  D  R  I  R  Q  G  Q  T  V  C  I  I  E  A  M  K  M
```

FIG. 8

SEQUENCE LISTING (1) GENERAL INFORMATION:

(iii) NUMBER OF SEQUENCES: 116

(2) INFORMATION FOR SEQ ID NO:1:

(i) SEQUENCE CHARACTERISTICS:
      (A) LENGTH:        3065 base pairs
      (B) TYPE:          Nucleic acid
      (C) STRANDEDNESS:  Single
      (D) TOPOLOGY:      Linear (ii) MOLECULE TYPE: Oligonucleotide (xi) SEQUENCE DESCRIPTION: SEQ ID NO:1:

```
AAGCTTTTAT ATTTTGCCAT TTCTAGAACT TAGCTGCATC GGCCCCAAGT ATTTTGTCAA      60
ATATGGCGAA AAGACTTCAT AAATCAAGGT TAAAGGTTGA CCGTGATGCC AAAACAGGTA     120
ATGGCGACCC CAGAAAGGCC CATCCACGCC AAAACCTAAT TGCAAGGCCT CTGAATTTCC     180
GTAATAAATA CCCCGCACAT CCCGATACAA CTCCGTGCGA AGACGAGCTA GACTTGCCCA     240
AATTGGTAAT GAACGGTTTT GCAAATACTC GTCTACATGG CTGGCTTCCC ACCATGAGGT     300
TGCATAGGCG AGTCGTTGGC CAGAGCGTGT ACGTAGCCAT ACCTGTCGCC GCAGTCTTGG     360
CGCTGGAACA GATTGGATTA AATCCGGCGC ACTATCTAAA TCCAAACCAA TCAATGACAT     420
ATCAATGACA TCGACTTCTG TTGGCTCACC AGTAAGTAAT TCTAAATGCC TTGTGGGTGA     480
GCCATCACCT AAGAGTAGTA GTTGCCACGC TGGAGCCAGC TGAGTGTGAG GCAAACTATG     540
TTTAATTACT TCTTCCCCAC CTTGCCAAAT AGGAGTGAGG CGATGCCATC CGGCTGGCAG     600
TGTTGAGTTG TTGCTTGGAG TAAAAGTGGC AGTCAATGTT CTTTACAAAA GTTCACCTAT     660
TTATATCAAA GCATAAAAAA TTAATTAGTT GTCAGTTGTC ATTGGTTATT CTTCTTTGCT     720
CCCCCTGCCC CCTACTTCCC TCCTCTGCCC AATAATTAGA AAGGTCAGGA GTCAAAAACT     780
TATCACTTTT GACCACTGAC CTTTCACAAT TGACTATAGT CACTAAAAAA TGCGGATGGC     840
GAGACTCGAA CTCGCAAGGC AAAGCCACAC GCACCTCAAG CGTGCGCGTA TACCAATTCC     900
GCCACATCCG CACGGGTTGT ACAAGAAGAT ATACTAGCAC AAAAAAATTG CATAAAACAA     960
GGTAAAACTA TATTTGCCAA ACTTTATGGA AAATTTATCT TGCTAAATAT ACAAATTTCC    1020
CGAAGAGGAT ACGAGACTAA CAGAAATGTA GTATCGCCAC AAGTGATATT AAAGGGGGTA    1080
TGGGGGTTTT CTTCCCTTAC ACCCTTAAAC CCTCACACCC CACCTCCATG AAAAATCTTG    1140
TTGGTAAGTC CGTTTCCTGC AATTTATTTA AAGATGAGCC TGGGGTATCT CCTGTCATAA    1200
TTTGAGATGA AGCGATGCCT AAGGCGGCTA CGCTACGCGC TAAAAGCAAC TTGGATGGGA    1260
GACAATTTCT ATCTGCTGGT ACTGATACTG ATATCGAAAA CTAGAAAATG AAGTTTGACA    1320
AAATATTAAT TGCCAATCGG GGAGAAATAG CGCTGCGCAT TCTCCGCGCC TGTGAGGAAA    1380
TGGGGATTGC GACGATCGCA GTTCATTCGA CTGTTGACCG GAATGCTCTT CATGTCCAAC    1440
TTGCTGACGA AGCGGTTTGT ATTGGCGAAC CTGCTAGCGC TAAAAGTTAT TTGAATATTC    1500
CCAATATTAT TGCTGCGGCT TTAACGCGCA ATGCCAGTGC TATTCATCCT GGGTATGGCT    1560
TTTTATCTGA AAATGCCAAA TTTGCGGAAA TCTGTGCTGA CCATCACATT GCATTCATTG    1620
GCCCCACCCC AGAAGCTATC CGCCTCATGG GGACAAATC  CACTGCCAAG GAAACCATGC    1680
AAAAAGCTGG TGTACCGACA GTACCGGGTA GTGAAGGTTT GGTAGAGACA GAGCAAGAAG    1740
GATTAGAACT GGCGAAAGAT ATTGGCTACC CAGTGATGAT CAAAGCCACG GCTGGTGGTG    1800
GCGGCCGGGG TATGCGACTG GTGCGATCGC CAGATGAATT TGTCAAACTG TTCTTAGCCG    1860
CCCAAGGTGA AGCTGGTGCA GCCTTTGGTA ATGCTGGCGT TTATATAGAA AAATTTATTG    1920
AACGTCCGCG CCACATTGAA TTTCAAATTT TGGCTGATAA TTACGGCAAT GTGATTCACT    1980
TGGGTGAGAG GGATTGCTCA ATTCAGCGTC GTAACCAAAA GTTACTAGAA GAAGCCCCCA    2040
GCCCAGCCTT GGACTCAGAC CTAAGGGAAA AAATGGGACA AGCGGCGGTG AAAGCGGCTC    2100
AGTTTATCAA TTCGCCGGG  GCAGGTACTA TCGAGTTTTT GCTAGATAGA TCCGGTCAGT    2160
TTTACTTTAT GGAGATGAAC ACCCGGATTC AAGTAGAACA TCCCGTAACT GAGATGGTTA    2220
CTGGAGTGGA TTTATTGGTT GAGCAAATCA GAATTGCCCA AGGGGAAAGA CTTAGACTAA    2280
```

```
CTCAAGACCA AGTAGTTTTA CGCGGTCATG CGATCGAATG TCGCATCAAT GCCGAAGACC    2340

CAGACCACGA TTTCCGCCCA GCACCCGGAC GCATTAGCGG TTATCTTCCC CCTGGCGGCC    2400

CTGGCGTGCG GATTGACTCC CACGTTTACA CGGATTACCA AATTCCGCCC TACTACGATT    2460

CCTTAATTGG TAAATTGATC GTTTGGGGCC CTGATCGCGC TACTGCTATT AACCGCATGA    2520

AACGCGCCCT CAGGGAATGC GCCATCACTG GATTACCTAC AACCATTGGG TTTCATCAAA    2580

GAATTATGGA AATCCCCAA TTTTTACAAG GTAATGTGTC TACTAGTTTT GTGCAGGAGA     2640

TGAATAAATA GGGTAATGGG TAATGGGTAA TGGGTAATAA AGTTTCAATC ACCAATTACC    2700

AATTCCCTAA CTCATCCGTG CCAACATCGT CAGTAATCCT TGCTGGCCTA GAAGAACTTC    2760

TCGCAACAGG CTAAAAATAC CAACACACAC AATGGGGGTG ATATCAACAC CACCTATTGG    2820

TGGGATGATT TTTCGCAAGG GAATGAGAAA TGGTTCAGTC GGCCAAGCAA TTAAGTTGAA    2880

GGGCAAACGG TTCAGATCGA CTTGCGGATA CCAGGTCAGA ATGATACGGA AAATAAACAG    2940

AAATGTCATC ACTCCCAATA CAGGGCCAAG AATCCAAACG CTCAGGTTAA CACCAGTCAT    3000

CGATCTAAGC TACTATTTTG TGAATTTACA AAAAACTGCA AGCAAAAGCT GAAAATTTTA    3060

AGCTT                                                                3065
```

(2) INFORMATION FOR SEQ ID NO:2:

(i) SEQUENCE CHARACTERISTICS:
        (A) LENGTH: 32 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:2:

```
Asp Glu Ala Met Pro Lys Ala Ala Thr Leu Arg Ala Lys Ser Asn Leu
              5                  10                  15

Asp Gly Arg Gln Phe Leu Ser Ala Gly Thr Asp Thr Asp Ile Glu Asn
             20                  25                  30
```

(2) INFORMATION FOR SEQ ID NO:3:

(i) SEQUENCE CHARACTERISTICS:
        (A) LENGTH: 427 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:3:

```
Lys Met Lys Phe Asp Lys Ile Leu Ile Ala Asn Arg Gly Glu Ile Ala
              5                  10                  15

Leu Arg Ile Leu Arg Ala Cys Glu Glu Met Gly Ile Ala Thr Ile Ala
             20                  25                  30

Val His Ser Thr Val Asp Arg Asn Ala Leu His Val Gln Leu Ala Asp
             35                  40                  45

Glu Ala Val Cys Ile Gly Glu Pro Ala Ser Ala Lys Ser Tyr Leu Asn
         50                  55                  60

Ile Pro Asn Ile Ile Ala Ala Leu Thr Arg Asn Ala Ser Ala Ile
65                  70                  75                  80

His Pro Gly Tyr Gly Phe Leu Ser Glu Asn Ala Lys Phe Ala Glu Ile
             85                  90                  95

Cys Ala Asp His His Ile Ala Phe Ile Gly Pro Thr Pro Glu Ala Ile
```

```
                    100                 105                 110
Arg Leu Met Gly Asp Lys Ser Thr Ala Lys Glu Thr Met Gln Lys Ala
                115                 120                 125
Gly Val Pro Thr Val Pro Gly Ser Glu Gly Leu Val Glu Thr Glu Gln
130                 135                 140
Glu Gly Leu Glu Leu Ala Lys Asp Ile Gly Tyr Pro Val Met Ile Lys
145                 150                 155                 160
Ala Thr Ala Gly Gly Gly Gly Arg Gly Met Arg Leu Val Arg Ser Pro
                165                 170                 175
Asp Glu Phe Val Lys Leu Phe Leu Ala Ala Gln Gly Glu Ala Gly Ala
                180                 185                 190
Ala Phe Gly Asn Ala Gly Val Tyr Ile Glu Lys Phe Ile Glu Arg Pro
                195                 200                 205
Arg His Ile Glu Phe Gln Ile Leu Ala Asp Asn Tyr Gly Asn Val Ile
                210                 215                 220
His Leu Glu Arg Asp Cys Ser Ile Gln Arg Arg Asn Gln Lys Leu Leu
225                 230                 235                 240
Glu Glu Ala Pro Ser Pro Ala Leu Asp Ser Asp Leu Arg Glu Lys Met
                245                 250                 255
Gly Gln Ala Ala Val Lys Ala Ala Gln Phe Ile Asn Tyr Ala Gly Ala
                260                 265                 270
Gly Thr Ile Glu Phe Leu Leu Asp Arg Ser Gly Gln Phe Gly Val Asp
                275                 280                 285
Leu Leu Val Glu Gln Ile Arg Ile Ala Gln Gly Glu Arg Leu Arg Leu
                290                 295                 300
Thr Gln Asp Gln Val Val Leu Arg Gly His Ala Ile Glu Cys Arg Ile
305                 310                 315                 320
Asn Ala Glu Asp Pro Asp His Asp Phe Arg Pro Ala Pro Gly Arg Ile
                325                 330                 335
Ser Gly Tyr Leu Pro Pro Gly Gly Pro Gly Val Arg Ile Asp Ser His
                340                 345                 350
Val Tyr Thr Asp Tyr Gln Ile Pro Pro Tyr Tyr Asp Ser Leu Ile Gly
                355                 360                 365
Lys Leu Ile Val Trp Gly Pro Asp Arg Ala Thr Ala Ile Asn Arg Met
370                 375                 380
Lys Arg Ala Leu Arg Glu Cys Ala Ile Thr Gly Leu Pro Thr Thr Ile
385                 390                 395                 400
Gly Phe His Gln Arg Ile Met Glu Asn Pro Gln Phe Leu Gln Gly Asn
                405                 410                 415
Val Ser Thr Ser Phe Val Gln Glu Met Asn Lys
                420                 425

(2) INFORMATION FOR SEQ ID NO:4:

(i) SEQUENCE CHARACTERISTICS:
        (A) LENGTH:      36 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:4:

Trp Val Met Gly Asn Arg Val Ser Ile Thr Asn Tyr Gln Phe Pro Asn
                 5                  10                  15
Ser Ser Val Pro Thr Ser Ser Val Ile Leu Ala Gly Leu Glu Glu Leu
                20                  25                  30
```

Leu Ala Thr Gly
    35

(2) INFORMATION FOR SEQ ID NO:5:

(i) SEQUENCE CHARACTERISTICS:
        (A) LENGTH:      1362 base pairs
        (B) TYPE:        Nucleic acid
        (C) STRANDEDNESS: Single
        (D) TOPOLOGY:    Linear (ii) MOLECULE TYPE:    Oligonucleotide (xi) SEQUENCE DESCRIPTION: SEQ ID NO:5:

ATGCGTTTCA ACAAGATCCT GATCGCCAAT CGCGGCGAAA TCGCCCTGCG CATTCTCCGC        60

ACTTGTCAAG AACTCGGGAT CGGCACGATC GCCGTTCACT CCACTGTGGA TCGCAACGCG       120

CTCCATGTGC AGTTAGCGGA CGAAGCGGTC TGTATTGGCG AAGCGGCCAG CAGCAAAAGC       180

TATCTCAATA TCCCCAACAT CATTGCGGCG GCCCTGACCC CTAATGCCAG CGCCATTCAC       240

CCCGGCTATG GCTTCTTGGC GGAGAATGCC CGCTTTGCAG AAATCTGCGC CGATCACCAT       300

CTCACCTTTA TTGGCCCCAG CCCCGATTCG ATTCGAGCCA TGGGCGATAA ATCCACCGCT       360

AAGGAAACAA TGCAGCGGGT CGGCGTTCCG ACGATTCCGG GCAGTGACGG TCTGCTGACG       420

GATGTTGATT CGGCTGCCAA AGTTGCTGCC GAGATCGGCT ATCCCGTCAT GATCAAAGCG       480

ACGGCGGGGG GCGGTGGTCG CGGTATGCGG CTGGTGCGTG ACCCTGCAGA TCTGGAAAAA       540

CTGTTCCTTG CTGCCCAAGG AGAAGCCGAG GCAGCTTTTG GAATCCAGG ACTGTATCTC        600

GAAAAATTTA TCGATCGCCC ACGCCACGTT GAATTTCAGA TCTTGGCCGA TGCCTACGGC       660

AATGTAGTGC ATCTAGGCGA GCGCGATTGC TCCATTCAAC GTCGTCACCA AAAGCTGCTC       720

GAAGAAGCCC CCAGTCCGGC GCTATCGGCA GACCTGCGGC AGAAAATGGG CGATGCCGCC       780

GTCAAAGTCG CTCAAGCGAT CGGCTACATC GGTGCCGGCA CCGTGGAGTT TCTGGTCGAT       840

GCGACCGGCA ACTTCTACTT CATGGAGATG AATACCCGCA TCCAAGTCGA GCATCCAGTC       900

ACAGAAATGA TTACGGGACT GGACTTGATT GCGGAGCAGA TTCGGATTGC CCAAGGCGAA       960

GCGCTGCGCT TCCGGCAAGC CGATATTCAA CTGCGCGGCC ATGCGATCGA ATGCCGTATC      1020

AATGCGGAAG ATCCGGAATA CAATTTCCGG CCGAATCCTG GCCGCATTAC AGGCTATTTA      1080

CCGCCCGGCG GCCCCGGCGT TCGTGTCGAT TCCCATGTTT ATACCGACTA CGAAATTCCG      1140

CCCTATTACG ATTCGCTGAT GGCAAATTG ATTGTCTGGG GTGCAACACG GGAAGAGGCG       1200

ATCGCGCGGA TGCAGCGTGC TCTGCGGGAA TGCGCCATCA CCGGCTTGCC GACGACCCTT      1260

AGTTTCCATC AGCTGATGTT GCAGATGCCT GAGTTCCTGC GCGGGGAACT CTATACCAAC      1320

TTTGTTGAGC AGGTGATGCT ACCTCGGATC CTCAAGTCCT AG                        1362

(2) INFORMATION FOR SEQ ID NO:6:

(i) SEQUENCE CHARACTERISTICS:
        (A) LENGTH:      453 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:6:

Met Arg Phe Asn Lys Ile Leu Ile Ala Asn Arg Gly Glu Ile Ala Leu
              5                  10                  15

-continued

```
Arg Ile Leu Arg Thr Cys Glu Glu Leu Gly Ile Gly Thr Ile Ala Val
            20                  25                  30

His Ser Thr Val Asp Arg Asn Ala Leu His Val Gln Leu Ala Asp Glu
        35                  40                  45

Ala Val Cys Ile Gly Glu Ala Ala Ser Ser Lys Ser Tyr Leu Asn Ile
 50                  55                  60

Pro Asn Ile Ile Ala Ala Ala Leu Thr Arg Asn Ala Ser Ala Ile His
 65                  70                  75                  80

Pro Gly Tyr Gly Phe Leu Ala Glu Asn Ala Arg Phe Ala Glu Ile Cys
                85                  90                  95

Ala Asp His His Leu Thr Phe Ile Gly Pro Ser Pro Asp Ser Ile Arg
            100                 105                 110

Ala Met Gly Asp Lys Ser Thr Ala Lys Glu Thr Met Gln Arg Val Gly
            115                 120                 125

Val Pro Thr Ile Pro Gly Ser Asp Gly Leu Leu Thr Asp Val Asp Ser
130                 135                 140

Ala Ala Lys Val Ala Ala Glu Ile Gly Tyr Pro Val Met Ile Lys Ala
145                 150                 155                 160

Thr Ala Gly Gly Gly Arg Gly Met Arg Leu Val Arg Glu Pro Ala
                165                 170                 175

Asp Leu Glu Lys Leu Phe Leu Ala Ala Gln Gly Glu Ala Glu Ala Ala
            180                 185                 190

Phe Gly Asn Pro Gly Leu Tyr Leu Glu Lys Phe Ile Asp Arg Pro Arg
            195                 200                 205

His Val Glu Phe Gln Ile Leu Ala Asp Ala Tyr Gly Asn Val Val Glu
            210                 215                 220

Leu Gly Glu Arg Asp Cys Ser Ile Gln Arg Arg His Gln Lys Leu Leu
225                 230                 235                 240

Glu Glu Ala Pro Ser Pro Ala Leu Ser Ala Asp Leu Arg Gln Lys Met
                245                 250                 255

Gly Asp Ala Ala Val Lys Val Ala Gln Ala Ile Gly Tyr Ile Gly Ala
            260                 265                 270

Gly Thr Val Glu Phe Leu Val Asp Ala Thr Gly Asn Phe Tyr Phe Met
            275                 280                 285

Glu Met Asn Thr Arg Ile Gln Val Glu His Pro Val Thr Glu Met Ile
            290                 295                 300

Thr Gly Leu Asp Leu Ile Ala Glu Gln Ile Arg Ile Ala Gln Gly Glu
305                 310                 315                 320

Ala Leu Arg Phe Arg Gln Ala Asp Ile Gln Leu Arg Gly His Ala Ile
                325                 330                 335

Glu Cys Arg Ile Asn Ala Glu Asp Pro Glu Tyr Asn Phe Arg Pro Asn
            340                 345                 350

Pro Gly Arg Ile Thr Gly Tyr Leu Pro Pro Gly Gly Pro Gly Val Arg
            355                 360                 265

Val Asp Ser His Val Tyr Thr Asp Tyr Glu Ile Pro Pro Tyr Tyr Asp
370                 375                 380

Ser Leu Ile Gly Lys Leu Ile Val Trp Gly Ala Thr Arg Glu Glu Ala
385                 390                 395                 400

Ile Ala Arg Met Gln Arg Ala Leu Arg Glu Gly Ala Ile Thr Gly Leu
                405                 410                 415

Pro Thr Thr Leu Ser Phe His Gln Leu Met Leu Gln Met Pro Glu Phe
            420                 425                 430

Leu Arg Gly Glu Leu Tyr Thr Asn Phe Val Glu Gln Val Met Leu Pro
            435                 440                 445
```

Arg Ile Leu Lys Ser
    450

(2) INFORMATION FOR SEQ ID NO:7:

(i) SEQUENCE CHARACTERISTICS:
        (A) LENGTH:       34 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION:  SEQ ID NO:7:

Met Asp Glu Pro Ser Pro Leu Ala Lys Thr Leu Glu Leu Asn Gln His
                5                  10                  15

Ser Arg Phe Ile Ile Gly Ser Val Ser Glu Asp Asn Ser Glu Asp Glu
            20                  25                  30

Ile Ser (2) INFORMATION FOR SEQ ID NO:8:

(i) SEQUENCE CHARACTERISTICS:
        (A) LENGTH:       187 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION:  SEQ ID NO:8:

Asn Leu Val Lys Leu Asp Leu Glu Glu Lys Glu Gly Ser Leu Ser Pro
                5                  10                  15

Ala Ser Val Ser Ser Asp Thr Leu Ser Asp Leu Gly Ile Ser Ala Leu
            20                  25                  30

Gln Asp Gly Leu Ala Phe His Met Arg Ser Ser Met Ser Gly Leu His
        35                  40                  45

Leu Val Lys Gln Gly Arg Asp Arg Lys Lys Ile Asp Ser Gln Arg Asp
 50                  55                  60

Phe Thr Val Ala Ser Pro Ala Glu Phe Val Thr Arg Phe Gly Gly Asn
65                  70                  75                  80

Lys Val Ile Glu Lys Val Leu Ile Ala Asn Asn Gly Ile Ala Ala Val
                85                  90                  95

Lys Cys Met Arg Ser Ile Arg Arg Trp Ser Tyr Glu Met Phe Arg Asn
            100                 105                 110

Glu Arg Ala Ile Arg Phe Val Val Met Val Thr Pro Glu Asp Leu Lys
        115                 120                 125

Ala Asn Ala Glu Tyr Ile Lys Met Ala Asp His Tyr Val Pro Val Pro
    130                 135                 140

Gly Gly Ala Asn Asn Asn Asn Tyr Ala Asn Val Glu Leu Ile Leu Asp
145                 150                 155                 160

Ile Ala Lys Arg Ile Pro Val Gln Ala Val Trp Ala Gly Trp Gly His
                165                 170                 175

Ala Ser Glu Asn Pro Lys Leu Pro Glu Leu Leu
            180                 185

(2) INFORMATION FOR SEQ ID NO:9:

(i) SEQUENCE CHARACTERISTICS:
        (A) LENGTH:       122 amino acids
        (B) TYPE:         Amino acid (C) STRANDEDNESS: Single
        (D) TOPOLOGY:    Linear (ii) MOLECULE TYPE:    Peptide (xi) SEQUENCE DESCRIPTION: SEQ ID NO:9:

Leu Lys Asn Gly Ile Ala Phe Met Gly Pro Pro Ser Gln Ala Met Trp
                 5                  10                  15

Ala Leu Gly Asp Lys Ile Ala Ser Ser Ile Val Ala Gln Thr Ala Gly
             20                  25                  30

Ile Pro Thr Leu Pro Trp Ser Gly Ser Gly Leu Arg Val Asp Trp Gln
         35                  40                  45

Glu Asn Asp Phe Ser Lys Arg Ile Leu Asn Val Pro Gln Asp Leu Tyr
     40                  55                  60

Glu Lys Gly Tyr Val Lys Asp Val Asp Gly Leu Lys Ala Ala Glu
65                  70                  75                  80

Glu Val Gly Tyr Pro Val Met Ile Lys Ala Ser Glu Gly Gly Gly
                 85                  90                  95

Lys Gly Ile Arg Lys Val Asn Asn Ala Asp Asp Phe Pro Asn Leu Phe
             100                 105                 110

Arg Gln Val Gln Ala Glu Val Pro Gly Ser
         115                 120

(2) INFORMATION FOR SEQ ID NO:10:

(i) SEQUENCE CHARACTERISTICS:
        (A) LENGTH:      86 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:10:

Pro Ile Phe Val Met Arg Leu Ala Lys Gln Ser Arg His Leu Glu Val
                 5                  10                  15

Gln Ile Leu Ala Asp Gln Tyr Gly Asn Ala Ile Ser Leu Phe Gly Arg
             20                  25                  30

Asp Cys Ser Val Gln Arg Arg His Gln Lys Ile Ile Glu Glu Ala Pro
         35                  40                  45

Ala Ala Ile Ala Thr Pro Ala Val Phe Glu His Met Glu Gln Cys Ala
50                  55                  60

Val Lys Leu Ala Lys Met Val Gly Tyr Val Ser Ala Gly Thr Val Glu
65                  70                  75                  80

Tyr Leu Tyr Ser Gln Asp
                 85

(2) INFORMATION FOR SEQ ID NO:11:

(i) SEQUENCE CHARACTERISTICS:
        (A) LENGTH:      70 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:11:

Gly Ser Phe Tyr Phe Leu Glu Leu Asn Pro Arg Leu Gln Val Glu His
                 5                  10                  15

Pro Cys Thr Glu Met Val Ala Asp Val Asn Leu Pro Ala Ala Gln Leu
             20                  25                  30

```
Gln Ile Ala Met Gly Ile Pro Leu Phe Arg Ile Lys Asp Ile Arg Met
            35                  40                  45
Met Tyr Gly Val Ser Pro Trp Gly Asp Ala Pro Ile Asp Phe Glu Asn
 50                  55                  60
Ser Ala His Val Pro Cys
 65                  70
```

(2) INFORMATION FOR SEQ ID NO:12:

(i) SEQUENCE CHARACTERISTICS:
        (A) LENGTH:        20 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:12:

```
Pro Arg Gly His Val Ile Ala Ala Arg Ile Thr Ser Glu Asn Pro Asp
                  5                  10                  15
Glu Gly Phe Lys
             20
```

(2) INFORMATION FOR SEQ ID NO:13:

(i) SEQUENCE CHARACTERISTICS:
        (A) LENGTH:        21 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:13:

```
Pro Ser Ser Gly Thr Val Gln Glu Leu Asn Phe Arg Ser Asn Lys Asn
                  5                  10                  15
Val Trp Gly Tyr Phe
             20
```

(2) INFORMATION FOR SEQ ID NO:14:

(i) SEQUENCE CHARACTERISTICS:
        (A) LENGTH:        122 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:14:

```
Ser Val Ala Ala Ala Gly Gly Leu His Glu Phe Ala Asp Ser Gln Phe
                  5                  10                  15
Gly His Cys Phe Ser Trp Gly Glu Asn Arg Glu Ala Ile Ser Asn
             20                  25                  30
Met Val Ala Leu Lys Glu Leu Ser Ile Arg Gly Asp Phe Arg Thr
      35                  40                  45
Thr Val Glu Tyr Leu Ile Lys Leu Leu Glu Thr Glu Ser Phe Gln Leu
 50                  55                  60
Asn Arg Ile Asp Thr Gly Trp Leu Asp Arg Leu Ile Ala Glu Lys Val
 65                  70                  75                  80
Gln Ala Glu Arg Pro Asp Thr Met Leu Gly Val Val Cys Gly Ala Leu
                 85                  90                  95
His Val Ala Asp Val Asn Leu Arg Asn Ser Ile Ser Asn Phe Leu His
```

```
                        100                 105                 110
Ser Leu Glu Arg Gly Gln Val Leu Pro Ala
            115                 120

(2) INFORMATION FOR SEQ ID NO:15:

(i) SEQUENCE CHARACTERISTICS:
        (A) LENGTH:      190 amino acids
        (B) TYPE:        Amino acid
        (C) STRANDEDNESS: Single
        (D) TOPOLOGY:    Linear (ii) MOLECULE TYPE:      Peptide (xi) SEQUENCE DESCRIPTION: SEQ ID NO:15:

His Thr Leu Leu Asn Thr Val Asp Val Glu Leu Ile Tyr Glu Gly Ile
                5                  10                  15

Lys Tyr Val Leu Lys Val Thr Arg Gln Ser Pro Asn Ser Tyr Val Val
             20                  25                  30

Ile Met Asn Gly Ser Cys Val Glu Val Asp Val His Arg Leu Ser Asp
         35                  40                  45

Gly Gly Leu Leu Leu Ser Tyr Asp Gly Ser Ser Tyr Thr Thr Tyr Met
     50                  55                  60

Lys Glu Glu Val Asp Arg Tyr Arg Ile Thr Ile Gly Asn Lys Thr Cys
65                  70                  75                  80

Val Phe Glu Lys Glu Asn Asp Pro Ser Val Met Arg Ser Pro Ser Ala
                 85                  90                  95

Gly Lys Leu Ile Gln Tyr Ile Val Glu Asp Gly Gly His Val Phe Ala
            100                 105                 110

Gly Gln Cys Tyr Ala Glu Ile Glu Val Met Lys Met Val Met Thr Leu
        115                 120                 125

Thr Ala Val Glu Ser Gly Cys Ile His Tyr Val Lys Arg Pro Gly Ala
    130                 135                 140

Ala Leu Asp Pro Gly Cys Val Ile Ala Lys Met Gln Leu Asp Asn Pro
145                 150                 155                 160

Ser Lys Val Gln Gln Ala Glu Leu His Thr Gly Ser Leu Pro Gln Ile
                165                 170                 175

Gln Ser Thr Ala Leu Arg Gly Leu Lys Leu His Arg Ile Phe
            180                 185                 190

(2) INFORMATION FOR SEQ ID NO:16:

(i) SEQUENCE CHARACTERISTICS:
        (A) LENGTH:      37 amino acids
        (B) TYPE:        Amino acid
        (C) STRANDEDNESS: Single
        (D) TOPOLOGY:    Linear (ii) MOLECULE TYPE:      Peptide (xi) SEQUENCE DESCRIPTION: SEQ ID NO:16:

Val Met Ile Lys Ala Ser Trp Gly Gly Gly Gly Lys Gly Ile Arg Lys
                5                  10                  15

Val His Asn Asp Asp Glu Val Arg Ala Leu Phe Lys Gln Val Gln Gly
             20                  25                  30

Glu Val Pro Gly Ser
         35

(2) INFORMATION FOR SEQ ID NO:17:

(i) SEQUENCE CHARACTERISTICS:
```

```
            (A) LENGTH:        187 amino acids
            (B) TYPE:          Amino acid
            (C) STRANDEDNESS:  Single
            (D) TOPOLOGY:      Linear (ii) MOLECULE TYPE:       Peptide (xi) SEQUENCE DESCRIPTION:  SEQ ID NO:17:
```

Pro Ile Phe Ile Met Lys Val Ala Ser Gln Ser Arg His Leu Glu Val
                 5                  10                  15

Gln Leu Leu Cys Asp Lys His Gly Asn Val Ala Ala Leu His Ser Arg
                20                  25                  30

Asp Cys Ser Val Gln Arg Arg His Gln Lys Ile Ile Glu Glu Gly Pro
                35                  40                  45

Ile Thr Val Ala Pro Pro Glu Thr Ile Lys Glu Leu Glu Gln Ala Ala
        50                  55                  60

Arg Arg Leu Ala Lys Cys Val Gln Tyr Gln Gly Ala Ala Thr Val Glu
65                  70                  75                  80

Tyr Leu Tyr Ser Met Glu Thr Gly Glu Tyr Tyr Phe Leu Glu Leu Asn
                85                  90                  95

Pro Arg Leu Gln Val Glu His Pro Val Thr Glu Trp Ile Ala Glu Ile
                100                 105                 110

Asn Leu Pro Ala Ser Gln Val Val Val Gly Met Gly Ile Pro Leu Tyr
                115                 120                 125

Asn Ile Pro Glu Ile Arg Arg Phe Tyr Gly Ile Glu His Gly Gly Gly
                130                 135                 140

Tyr His Ala Trp Lys Glu Ile Ser Ala Val Ala Thr Lys Phe Asp Leu
145                 150                 155                 160

Asp Lys Ala Gln Ser Val Lys Pro Lys Gly His Cys Val Ala Val Arg
                165                 170                 175

Val Thr Ser Glu Asp Pro Asp Asp Gly Phe Lys
                180                 185

(2) INFORMATION FOR SEQ ID NO:18:

```
     (i) SEQUENCE CHARACTERISTICS:
            (A) LENGTH:        21 amino acids
            (B) TYPE:          Amino acid
            (C) STRANDEDNESS:  Single
            (D) TOPOLOGY:      Linear (ii) MOLECULE TYPE:       Peptide (xi) SEQUENCE DESCRIPTION:  SEQ ID NO:18:
```

Pro Thr Ser Gly Arg Val Glu Glu Leu Asn Phe Lys Ser Lys Pro Asn
                5                   10                  15

Val Trp Ala Tyr Phe
                20

(2) INFORMATION FOR SEQ ID NO:19:

```
     (i) SEQUENCE CHARACTERISTICS:
            (A) LENGTH:        122 amino acids
            (B) TYPE:          Amino acid
            (C) STRANDEDNESS:  Single
            (D) TOPOLOGY:      Linear (ii) MOLECULE TYPE:       Peptide (xi) SEQUENCE DESCRIPTION:  SEQ ID NO:19:
```

Ser Val Lys Ser Gly Gly Ala Ile His Glu Phe Ser Asp Ser Gln Phe
                5                   10                  15

Gly His Val Phe Ala Phe Gly Glu Ser Arg Ser Leu Ala Ile Ala Asn
                    20                  25                  30

Met Val Leu Gly Leu Lys Glu Ile Gln Ile Arg Gly Glu Ile Arg Thr
             35                  40                  45

Asn Val Asp Tyr Thr Val Asp Leu Leu Asn Ala Ala Glu Tyr Arg Glu
         50                  55                  60

Asn Met Ile His Thr Gly Trp Leu Asp Ser Arg Ile Ala Met Arg Val
65                   70                  75                   80

Arg Ala Glu Arg Pro Pro Trp Tyr Leu Ser Val Val Gly Gly Ala Leu
                 85                  90                  95

Tyr Glu Ala Ser Ser Arg Ser Ser Val Val Thr Asp Tyr Val Gly
                100                 105                 110

Tyr Leu Ser Lys Gly Gln Ile Pro Pro Lys
            110                 120

(2) INFORMATION FOR SEQ ID NO:20:

(i) SEQUENCE CHARACTERISTICS:
        (A) LENGTH:       124 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:20:

His Ile Ser Leu Val Asn Leu Thr Val Thr Leu Asn Ile Asp Gly Ser
                 5                  10                  15

Lys Tyr Thr Ile Glu Thr Val Arg Gly Gly Pro Arg Ser Tyr Lys Leu
                20                  25                  30

Arg Ile Asn Glu Ser Glu Val Glu Ala Glu Ile His Phe Leu Arg Asp
            35                  40                  45

Gly Gly Leu Leu Met Gln Leu Asp Gly Asn Ser His Val Ile Tyr Ala
         50                  55                  60

Glu Thr Glu Ala Ala Gly Thr Arg Leu Leu Ile Asn Gly Arg Thr Cys
65                   70                  75                   80

Leu Leu Gln Lys Glu His Asp Pro Ser Arg Leu Leu Ala Asp Thr Pro
                 85                  90                  95

Cys Lys Leu Leu Arg Phe Leu Val Ala Asp Gly Ser His Val Val Ala
                100                 105                 110

Asp Thr Pro Tyr Ala Glu Val Glu Ala Met Lys Met
            115                 120

(2) INFORMATION FOR SEQ ID NO:21:

(i) SEQUENCE CHARACTERISTICS:
        (A) LENGTH:       222 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:21:

Met Glu Glu Ser Ser Gln Pro Ala Lys Pro Leu Glu Met Asn Pro His
                 5                  10                  15

Ser Arg Phe Ile Ile Gly Ser Val Ser Glu Asp Asn Ser Glu Asp Glu
                20                  25                  30

Thr Ser Ser Leu Val Lys Leu Asp Leu Leu Glu Glu Lys Glu Arg Ser
            35                  40                  45

```
Leu Ser Pro Val Ser Val Cys Ser Asp Ser Leu Ser Asp Leu Gly Leu
 50                  55                  60
Pro Ser Ala Gln Asp Gly Leu Ala Asn His Met Arg Pro Ser Met Ser
 65                  70                  75                  80
Gly Leu His Leu Val Lys Gln Gly Arg Asp Arg Lys Lys Val Asp Val
                 85                  90                  95
Gln Arg Asp Phe Thr Val Ala Ser Pro Ala Glu Phe Val Thr Arg Phe
                100                 105                 110
Gly Gly Asn Arg Val Ile Glu Lys Val Leu Ile Ala Asn Asn Gly Ile
                115                 120                 125
Ala Ala Val Lys Cys Met Arg Ser Ile Arg Arg Trp Ser Tyr Glu Met
130                 135                 140
Phe Arg Asn Glu Arg Ala Ile Arg Phe Val Val Met Val Thr Pro Glu
145                 150                 155                 160
Asp Leu Lys Ala Asn Ala Glu Tyr Ile Lys Met Ala Asp His Tyr Val
                165                 170                 175
Pro Val Pro Gly Gly Pro Asn Asn Asn Tyr Ala Asn Val Glu Leu
                180                 185                 190
Ile Leu Asp Ile Ala Lys Arg Ile Pro Val Gln Ala Val Trp Ala Gly
                195                 200                 205
Trp Gly His Ala Ser Glu Asn Pro Lys Leu Pro Glu Leu Leu
210                 215                 220

(2) INFORMATION FOR SEQ ID NO:22:

(i) SEQUENCE CHARACTERISTICS:
        (A) LENGTH:       122 amino acids
        (B) TYPE:         Amino acid
        (C) STRANDEDNESS: Single
        (D) TOPOLOGY:     Linear (ii) MOLECULE TYPE:       Peptide (xi) SEQUENCE DESCRIPTION: SEQ ID NO:22:

His Lys Asn Gly Ile Ala Phe Met Gly Pro Pro Ser Gln Ala Met Trp
                 5                  10                  15
Ala Leu Gly Asp Lys Ile Ala Ser Ser Ile Val Ala Gln Thr Ala Gly
                20                  25                  30
Ile Pro Thr Leu Pro Trp Asn Gly Ser Gly Leu Arg Val Asp Trp Gln
                35                  40                  45
Glu Asn Asp Leu Gln Lys Arg Ile Leu Asn Val Pro Gln Glu Leu Tyr
 50                  55                  60
Glu Lys Gly Tyr Val Lys Asp Ala Asp Gly Leu Arg Ala Ala Glu
 65                  70                  75                  80
Glu Val Gly Tyr Pro Val Met Ile Lys Ala Ser Glu Gly Gly Gly Gly
                 85                  90                  95
Lys Gly Ile Arg Lys Val Asn Asn Ala Asp Asp Phe Pro Asn Leu Phe
                100                 105                 110
Arg Gln Val Gln Ala Glu Val Pro Gly Ser
                115                 120

(2) INFORMATION FOR SEQ ID NO:23:

(i) SEQUENCE CHARACTERISTICS:
        (A) LENGTH:       95 amino acids
        (B) TYPE:         Amino acid
        (C) STRANDEDNESS: Single
        (D) TOPOLOGY:     Linear (ii) MOLECULE TYPE:       Peptide
```

(xi) SEQUENCE DESCRIPTION: SEQ ID NO:23:

Pro Ile Phe Val Met Arg Leu Ala Lys Gln Ser Arg His Leu Glu Val
            5                   10                  15

Gln Ile Leu Ala Asp Gln Tyr Gly Asn Ala Ile Ser Leu Phe Gly Arg
            20                  25                  30

Asp Cys Ser Val Gln Arg Arg His Gln Lys Ile Ile Glu Glu Ala Gly
            35                  40                  45

Leu Arg Ala Ala Glu Glu Val Gly Tyr Pro Val Met Ile Lys Ala Ser
50                  55                  60

Glu Gly Gly Gly Gly Lys Gly Ile Arg Lys Val Asn Ala Asp Asp
65                  70                  75              80

Phe Pro Asn Leu Phe Arg Gln Val Gln Ala Glu Val Pro Gly Ser
85                  90                  95

(2) INFORMATION FOR SEQ ID NO:24:

(i) SEQUENCE CHARACTERISTICS:
        (A) LENGTH:      86 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:24:
        Pro Ile Phe Val Met Arg Leu Ala Lys Gln Ser Arg His Leu Glu Val
        5                   10                  15
        Gln Ile Leu Ala Asp Gln Tyr Gly Asn Ala Ile Ser Leu Phe Gly Arg
        20                  25                  30
        Asp Cys Ser Val Gln Arg Arg His Gln Lys Ile Ile Glu Glu Ala Pro
        35                  40                  45
        Ala Ser Ile Ala Thr Ser Val Val Phe Glu His Met Gly Gln Cys Ala
        50                  55                  60
        Val Lys Leu Ala Lys Met Val Gly Tyr Val Ser Ala Gly Thr Val Glu
        65                  70                  75              80
        Tyr Leu Tyr Ser Gln Asp
        85

(2) INFORMATION FOR SEQ ID NO:25:

(i) SEQUENCE CHARACTERISTICS:
        (A) LENGTH:      70 amino acids
        (B) TYPE:        Amino acids
        (C) STRANDEDNESS: Single
        (D) TOPOLOGY:    Linear (ii) MOLECULE TYPE:    Peptide (xi) SEQUENCE DESCRIPTION: SEQ ID NO:25:
        Gly Ser Phe Tyr Phe Leu Glu Leu Asn Pro Arg Leu Gln Val Glu His
        5                   10                  15
        Pro Cys Thr Glu Met Val Ala Asp Val Asn Leu Pro Ala Ala Gln Leu
        20                  25                  30
        Gln Ile Ala Met Gly Ile Pro Leu His Arg Ile Lys Asp Ile Arg Val
        35                  40                  45
        Met Tyr Gly Val Ser Pro Trp Gly Asp Gly Ser Ile Asp Phe Glu Asn
        50                  35                  60
        Ser Ala His Val Pro Cys
        65                  70

(2) INFORMATION FOR SEQ ID NO:26:

(i) SEQUENCE CHARACTERISTICS:
        (A) LENGTH:      20 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:26:
        Pro Arg Gly His Val Ile Ala Ala Arg Ile Thr Ser Glu Asn Pro Asp

```
                    5              10              15
            Glu Gly Phe Lys
            20
```

(2) INFORMATION FOR SEQ ID NO:27:

(i) SEQUENCE CHARACTERISTICS:
       (A) LENGTH:       21 amino acids
       (B) TYPE:         Amino acid
       (C) STRANDEDNESS: Single
       (D) TOPOLOGY:     Linear (ii) MOLECULE TYPE:    Peptide (xi) SEQUENCE DESCRIPTION: SEQ ID NO:27:

```
            Pro Ser Ser Gly Thr Val Gln Glu Leu Asn Phe Arg Ser Asn Lys Asn
            5                   10                  15
            Val Trp Gly Tyr Phe
            20
```

(2) INFORMATION FOR SEQ ID NO:28:

(i) SEQUENCE CHARACTERISTICS:
       (A) LENGTH:       122 amino acids
       (B) TYPE:         Amino acid
       (C) STRANDEDNESS: Single
       (D) TOPOLOGY:     Linear (ii) MOLECULE TYPE:    Peptide (xi) SEQUENCE DESCRIPTION: SEQ ID NO:28:

```
            Ser Val Ala Ala Ala Gly Gly Leu His Glu Phe Ala Asp Ser Gln Phe
            5                   10                  15
            Gly His Cys Phe Ser Trp Gly Glu Asn Arg Glu Glu Ala Ile Ser Asn
            20                  25                  30
            Met Val Val Ala Leu Lys Glu Leu Ser Ile Arg Gly Asp Phe Arg Thr
            35                  40                  45
            Thr Val Glu Tyr Leu Ile Lys Leu Leu Glu Thr Glu Ser Phe Gln Gln
            50                  55                  60
            Asn Arg Ile Asp Thr Gly Trp Leu Asp Arg Leu Ile Ala Glu Lys Val
            65                  70                  75                  80
            Gln Ala Glu Arg Pro Asp Thr Met Leu Gly Val Val Cys Gly Ala Leu
            85                  90                  95
            His Val Ala Asp Val Ser Phe Arg Asn Ser Val Ser Asn Phe Leu His
            100                 105                 110
            Ser Leu Glu Arg Gly Gln Val Leu Pro Ala
            115                 120
```

(2) INFORMATION FOR SEQ ID NO:29:

(i) SEQUENCE CHARACTERISTICS:
       (A) LENGTH:       90 amino acids
       (B) TYPE:         Amino acid
       (C) STRANDEDNESS: Single
       (D) TOPOLOGY:     Linear (ii) MOLECULE TYPE:    Peptide (xi) SEQUENCE DESCRIPTION: SEQ ID NO:29:

```
            Met Val Val Ala Leu Lys Glu Leu Ser Ile Arg Gly Asp Phe Arg Thr
            5                   10                  15
            Thr Val Glu Tyr Leu Ile Lys Leu Leu Glu Thr Glu Ser Phe Gln Gln
            20                  25                  30
            Asn Arg Ile Asp Thr Gly Trp Leu Asp Arg Leu Ile Ala Glu Lys Val
            35                  40                  45
            Gln Ala Glu Arg Pro Asp Thr Met Leu Gly Val Val Cys Gly Ala Leu
            50                  55                  60
            His Val Ala Asp Val Ser Phe Arg Asn Ser Val Ser Asn Phe Leu His
            65                  70                  75                  80
            Ser Leu Glu Arg Gly Gln Val Leu Pro Ala
            85                  90
```

(2) INFORMATION FOR SEQ ID NO:30:

(i) SEQUENCE CHARACTERISTICS:
       (A) LENGTH:       190 amino acids
       (B) TYPE:         Amino acid
       (C) STRANDEDNESS: Single
       (D) TOPOLOGY:     Linear

```
    (ii) MOLECULE TYPE:      Peptide (xi) SEQUENCE DESCRIPTION: SEQ ID NO:30:
             His Thr Leu Leu Asn Thr Val Asp Val Glu Leu Ile Tyr Glu Gly Arg
             5                   10                  15
             Lys Tyr Val Leu Lys Val Thr Arg Gln Ser Pro Asn Ser Tyr Val Val
             20                  25                  30
             Ile Met Asn Ser Ser Cys Val Glu Val Asp Val His Arg Leu Ser Asp
             35                  40                  45
             Gly Gly Leu Leu Leu Ser Tyr Asp Gly Ser Ser Tyr Thr Thr Tyr Met
             50                  55                  60
             Lys Glu Glu Val Asp Arg Tyr Arg Ile Thr Ile Gly Asn Lys Thr Cys
             65                  70                  75                  80
             Val Phe Glu Lys Glu Asn Asp Pro Ser Ile Leu Arg Ser Pro Ser Ala
             85                  90                  95
             Gly Lys Leu Ile Gln Tyr Val Val Glu Asp Gly His Val Phe Ala
             100                 105                 110
             Gly Gln Cys Phe Ala Glu Ile Glu Val Met Lys Met Val Met Thr Leu
             115                 120                 125
             Thr Ala Gly Glu Ser Gly Cys Ile His Tyr Val Lys Arg Pro Gly Ala
             130                 135                 140
             Val Leu Asp Pro Gly Cys Val Ile Ala Lys Leu Gln Leu Asp Asp Pro
             145                 150                 155                 160
             Ser Arg Val Gln Gln Ala Glu Leu His Thr Gly Thr Leu Pro Gln Ile
             165                 170                 175
             Gln Ser Thr Ala Leu Arg Gly Glu Lys Leu His Arg Ile Phe
             180                 185                 190

(2) INFORMATION FOR SEQ ID NO:31:

(i) SEQUENCE CHARACTERISTICS:
         (A) LENGTH:       41 amino acids
         (B) TYPE:         Amino acid
         (C) STRANDEDNESS: Single
         (D) TOPOLOGY:     Linear (ii) MOLECULE TYPE:      Peptide (xi) SEQUENCE DESCRIPTION: SEQ ID NO:31:
             Met Ser Glu Glu Ser Leu Phe Glu Ser Pro Gln Lys Met Glu Tyr
             5                   10                  15
             Glu Ile Thr Asn Tyr Ser Glu Arg His Thr Glu Leu Pro Gly His Phe
             20                  25                  30
             Ile Gly Leu Asn Thr Val Asp Lys Leu
             35                  40

(2) INFORMATION FOR SEQ ID NO:32:

(i) SEQUENCE CHARACTERISTICS:
         (A) LENGTH:       74 amino acids
         (B) TYPE:         Amino acid
         (C) STRANDEDNESS: Single
         (D) TOPOLOGY:     Linear (ii) MOLECULE TYPE:      Peptide (xi) SEQUENCE DESCRIPTION: SEQ ID NO:32:
             Ala Asp Val Asp Ala Val Trp Ala Gly Trp Gly His Ala Ser Glu Asn
             5                   10                  15
             Pro Leu Leu Pro Glu Lys Leu Ser Gln Ser Lys Arg Lys Val Ile Phe
             20                  25                  30
             Ile Gly Pro Pro Gly Asn Ala Met Arg Ser Leu Gly Asp Lys Ile Ser
             35                  40                  45
             Ser Thr Thr Ile Val Ala Gln Ser Ala Lys Val Pro Cys Ile Pro Trp
             50                  55                  60
             Ser Gly Thr Thr Gly Val Asp Thr Val His
             65                  70

(2) INFORMATION FOR SEQ ID NO:33:

(i) SEQUENCE CHARACTERISTICS:
         (A) LENGTH:       73 amino acids
         (B) TYPE:         Amino acid
         (C) STRANDEDNESS: Single
         (D) TOPOLOGY:     Linear (ii) MOLECULE TYPE:      Peptide (xi) SEQUENCE DESCRIPTION: SEQ ID NO:33:
             Val Asp Glu Lys Thr Gly Leu Val Ser Val Asp Asp Ile Tyr Gln
```

```
            5
    Lys Gly Cys Cys Thr Ser Pro Glu Asp Gly Leu Gln Lys Ala Lys Arg
     20                      25                          30
    Ile Gly Phe Pro Val Met Ile Lys Ala Ser Glu Gly Gly Gly Gly Lys
     35                      40                      45
    Gly Ile Arg Gln Val Glu Arg Glu Glu Asp Phe Ile Ala Leu Tyr His
     50                      55                          60
    Gln Ala Ala Asn Glu Ile Pro Gly Ser
     65                      70
```

(2) INFORMATION FOR SEQ ID NO:34:

(i) SEQUENCE CHARACTERISTICS:
        (A) LENGTH: 157 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:34:

```
            Pro Ile Phe Ile Met Lys Leu Ala Gly Arg Ala Arg His Leu Glu Val
             5                      10                          15
            Gln Leu Leu Ala Asp Gln Tyr Gly Thr Asn Ile Ser Leu Phe Gly Arg
             20                      25                          30
            Asp Cys Ser Val Gln Arg Arg His Gln Lys Ile Ile Glu Glu Ala Pro
             35                      40                          45
            Val Thr Ile Ala Lys Ala Glu Thr Phe His Glu Met Gly Lys Ala Ala
             50                      55                      60
            Val Arg Leu Gly Lys Leu Val Gly Tyr Val Ser Ala Gly Thr Val Glu
             65                      70                      75                      80
            Tyr Leu Tyr Ser His Asp Asp Gly Lys Phe Tyr Phe Leu Glu Leu Asn
             85                      90                      95
            Pro Arg Leu Gln Val Glu His Pro Thr Thr Glu Met Val Ser Gly Val
            100                     105                     110
            Asn Leu Pro Ala Ala Gln Leu Gln Ile Ala Met Gly Ile Pro Met His
            115                     120                     125
            Arg Ile Ser Asp Ile Arg Thr Leu Tyr Gly Met Asn Pro His Ser Ala
            130                     135                     140
            Ser Glu Ile Asp Phe Glu Phe Lys Thr Gln Asp Ala Thr
            145                     150                     155
```

(2) INFORMATION FOR SEQ ID NO:35:

(i) SEQUENCE CHARACTERISTICS:
        (A) LENGTH: 27 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:35:

```
            Lys Lys Gln Arg Arg Pro Ile Pro Lys Gly His Cys Thr Ala Cys Arg
             5                      10                          15
            Ile Thr Ser Glu Asp Pro Asn Asp Gly Phe Lys
             20                      25
```

(2) INFORMATION FOR SEQ ID NO:36:

(i) SEQUENCE CHARACTERISTICS:
        (A) LENGTH: 21 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:36:

```
            Pro Ser Gly Gly Thr Leu His Glu Leu Asn Phe Arg Ser Ser Ser Asn
             5                      10                          15
            Val Trp Gly Tyr Phe
             20
```

(2) INFORMATION FOR SEQ ID NO:37:

(i) SEQUENCE CHARACTERISTICS:
        (A) LENGTH: 122 amino acids
        (B) TYPE: Amino acid
        (C) STRANDEDNESS: Single (D) TOPOLOGY: Linear (ii) MOLECULE TYPE: Peptide (xi) SEQUENCE DESCRIPTION: SEQ ID NO:37:

```
        Ser Val Gly Asn Asn Gly Asn Ile His Ser Phe Ser Asp Ser Gln Phe
        5                   10                                  15
        Gly His Ile Phe Ala Phe Gly Glu Asn Arg Gln Ala Ser Arg Lys His
        20                  25                  30
        Met Val Ala Leu Lys Glu Leu Ser Ile Arg Gly Asp Phe Arg Thr
        35                  40                  45
        Thr Val Glu Tyr Leu Ile Lys Leu Leu Glu Thr Glu Asp Phe Glu Asp
        50                  55                  60
        Asn Thr Ile Thr Thr Gly Trp Leu Asp Asp Leu Ile Thr His Lys Met
        65                  70                  75                  80
        Thr Ala Glu Lys Pro Asp Pro Thr Leu Ala Val Ile Cys Gly Ala Ala
        85                  90                  95
        Thr Lys Ala Phe Leu Ala Ser Glu Glu Ala Arg His Lys Tyr Ile Glu
        100                 105                 110
        Ser Leu Gln Lys Gly Gln Val Leu Ser Lys
        115                 120
```

(2) INFORMATION FOR SEQ ID NO:38:

(i) SEQUENCE CHARACTERISTICS:
        (A) LENGTH: 190 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:38:

```
        Asp Leu Leu Gln Thr Met Phe Pro Val Asp Phe Ile His Glu Gly Lys
        5                   10                  15
        Arg Tyr Lys Phe Thr Val Ala Lys Ser Gly Asn Asp Arg Tyr Thr Leu
        20                  25                  30
        Phe Ile Asn Gly Ser Lys Cys Asp Ile Ile Leu Arg Gln Leu Ser Asp
        35                  40                  45
        Gly Gly Leu Leu Ile Ala Ile Gly Gly Lys Ser His Thr Ile Tyr Trp
        50                  55                  60
        Lys Glu Glu Val Ala Ala Thr Arg Leu Ser Val Asp Ser Met Thr Thr
        65                  70                  75                  80
        Leu Leu Glu Val Glu Asn Asp Pro Thr Gln Leu Arg Thr Pro Ser Pro
        85                  90                  95
        Gly Lys Leu Val Lys Phe Leu Val Glu Asn Gly Glu His Ile Ile Lys
        100                 105                 110
        Gly Gln Pro Tyr Ala Glu Ile Glu Val Met Lys Met Gln Met Pro Leu
        115                 120                 125
        Val Ser Gln Glu Asn Gly Ile Val Gln Leu Leu Lys Gln Pro Gly Ser
        130                 135                 140
        Thr Ile Val Ala Gly Asp Ile Met Ala Ile Met Thr Leu Asp Asp Pro
        145                 150                                     160
        Ser Lys Val Lys His Ala Leu Pro Phe Glu Gly Met Leu Pro Asp Phe
        165                 170                 175
        Gly Ser Pro Val Ile Glu Gly Thr Lys Pro Ala Tyr Lys Phe
        180                 185                 190
```

(2) INFORMATION FOR SEQ ID NO:39:

(i) SEQUENCE CHARACTERISTICS:
        (A) LENGTH: 37 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:39:

```
        Met Arg Phe Asn Lys Ile Leu Ile Ala Asn Arg Gly Glu Ile Ala Leu
        5                   10                  15
        Arg Ile Leu Arg Thr Cys Glu Glu Leu Gly Ile Gly Thr Ile Ala Val
        20                  25                  30
        His Ser Thr Val Asp
        35
```

(2) INFORMATION FOR SEQ ID NO:40:

(i) SEQUENCE CHARACTERISTICS:
        (A) LENGTH: 21 amino acids

```
            (B) TYPE:          Amino acid
            (C) STRANDEDNESS: Single
            (D) TOPOLOGY:      Linear (ii) MOLECULE TYPE:        Peptide (xi) SEQUENCE DESCRIPTION: SEQ ID NO:40:
            Arg Asn Ala Leu His Val Gln Leu Ala Asp Glu Ala Val Cys Ile Gly
            5                   10                  15
            Glu Ala Ala Ser Ser
            20

(2) INFORMATION FOR SEQ ID NO:41:

(i) SEQUENCE CHARACTERISTICS:
            (A) LENGTH:        38 amino acids
            (B) TYPE:          Amino acid
            (C) STRANDEDNESS: Single
            (D) TOPOLOGY:      Linear (ii) MOLECULE TYPE:        Peptide (xi) SEQUENCE DESCRIPTION: SEQ ID NO:41:
            Lys Ser Tyr Leu Asn Ile Pro Asn Ile Ile Ala Ala Ala Leu Thr Arg
            5                   10                  15
            Asn Ala Ser Ala Ile His Pro Gly Tyr Gly Phe Leu Ala Glu Asn Ala
            20                  25                  30
            Arg Phe Ala Glu Ile Cys
            35

(2) INFORMATION FOR SEQ ID NO:42:

(i) SEQUENCE CHARACTERISTICS:
            (A) LENGTH:        41 amino acids
            (B) TYPE:          Amino acid
            (C) STRANDEDNESS: Single
            (D) TOPOLOGY:      Linear (ii) MOLECULE TYPE:        Peptide (xi) SEQUENCE DESCRIPTION: SEQ ID NO:42:
            Ala Asp His His Leu Thr Phe Ile Gly Pro Ser Pro Asp Ser Ile Arg
            5                   10                  15
            Ala Met Gly Asp Lys Ser Thr Ala Lys Glu Thr Met Gln Arg Val Gly
            20                  25                  30
            Val Pro Thr Ile Pro Gly Ser Asp Gly
            35                  40

(2) INFORMATION FOR SEQ ID NO:43:

(i) SEQUENCE CHARACTERISTICS:
            (A) LENGTH:        143 amino acids
            (B) TYPE:          Amino acid
            (C) STRANDEDNESS: Single
            (D) TOPOLOGY:      Linear (ii) MOLECULE TYPE:        Peptide (xi) SEQUENCE DESCRIPTION: SEQ ID NO:43:
            Leu Leu Thr Asp Val Asp Ser Ala Ala Lys Val Ala Ala Glu Ile Gly
            5                   10                  15
            Tyr Pro Val Met Ile Lys Ala Thr Ala Gly Gly Gly Gly Arg Gly Met
            20                  25                  30
            Arg Leu Val Arg Glu Pro Ala Asp Leu Glu Lys Leu Phe Leu Ala Ala
            35                  40                  45
            Gln Gly Glu Ala Glu Ala Phe Gly Asn Pro Gly Leu Tyr Leu Glu
            50                  55                  60
            Lys Phe Ile Asp Arg Pro Arg His Val Glu Phe Gln Ile Leu Ala Asp
            65                  70                  75                  80
            Ala Tyr Gly Asn Val Val His Leu Gly Glu Arg Asp Cys Ser Ile Gln
            85                  90                  95
            Arg Arg His Gln Lys Leu Leu Glu Glu Ala Pro Ser Pro Ala Leu Ser
            100                 105                 110
            Ala Asp Leu Arg Gln Lys Met Gly Asp Ala Ala Val Lys Val Ala Gln
            115                 120                 125
            Ala Ile Gly Tyr Ile Gly Ala Gly Thr Val Glu Phe Leu Val Asp
            130                 135                 140

(2) INFORMATION FOR SEQ ID NO:44:
```

(i) SEQUENCE CHARACTERISTICS:
            (A) LENGTH:       50 amino acids
            (B) TYPE:         Amino acid
            (C) STRANDEDNESS: Single
            (D) TOPOLOGY:     Linear (ii) MOLECULE TYPE:    Peptide (xi) SEQUENCE DESCRIPTION: SEQ ID NO:44:
            Ala Thr Gly Asn Phe Tyr Phe Met Glu Met Asn Thr Arg Ile Gln Val
            5                   10                  15
            Glu His Pro Val Thr Glu Met Ile Thr Gly Leu Asp Leu Ile Ala Glu
            20                  25                  30
            Gln Ile Arg Ile Ala Gln Gly Glu Ala Leu Arg Phe Arg Gln Ala Asp
            35                  40                  45
            Ile Gln
            50

(2) INFORMATION FOR SEQ ID NO:45:

(i) SEQUENCE CHARACTERISTICS:
            (A) LENGTH:       19 amino acids
            (B) TYPE:         Amino acid
            (C) STRANDEDNESS: Single
            (D) TOPOLOGY:     Linear (ii) MOLECULE TYPE:    Peptide (xi) SEQUENCE DESCRIPTION: SEQ ID NO:45:
            Leu Arg Gly His Ala Ile Glu Cys Arg Ile Asn Ala Glu Asp Pro Glu
            5                   10                  15
            Tyr Asn Phe (2) INFORMATION FOR SEQ ID NO:46:

(i) SEQUENCE CHARACTERISTICS:
            (A) LENGTH:       9 amino acids
            (B) TYPE:         Amino acid
            (C) STRANDEDNESS: Single
            (D) TOPOLOGY:     Linear (ii) MOLECULE TYPE:    Peptide (xi) SEQUENCE DESCRIPTION: SEQ ID NO:46:
            Arg Pro Asn Pro Gly Arg Ile Thr Gly
            5

(2) INFORMATION FOR SEQ ID NO:47:

(i) SEQUENCE CHARACTERISTICS:
            (A) LENGTH:       7 amino acids
            (B) TYPE:         Amino acid
            (C) STRANDEDNESS: Single
            (D) TOPOLOGY:     Linear (ii) MOLECULE TYPE:    Peptide (xi) SEQUENCE DESCRIPTION: SEQ ID NO:47:
            Pro Gly Val Arg Val Asp Ser
            5

(2) INFORMATION FOR SEQ ID NO:48:

(i) SEQUENCE CHARACTERISTICS:
            (A) LENGTH:       44 amino acids
            (B) TYPE:         Amino acid
            (C) STRANDEDNESS: Single
            (D) TOPOLOGY:     Linear (ii) MOLECULE TYPE:    Peptide (xi) SEQUENCE DESCRIPTION: SEQ ID NO:48:
            His Val Tyr Thr Asp Tyr Glu Ile Pro Pro Tyr Asp Ser Leu Ile
            5                   10                  15
            Gly Lys Leu Ile Val Trp Gly Ala Thr Arg Glu Glu Ala Ile Ala Arg
            20                  25                  30
            Met Gln Arg Ala Leu Arg Glu Cys Ala Ile Thr Gly
            35                  40

(2) INFORMATION FOR SEQ ID NO:49:

```
    (i) SEQUENCE CHARACTERISTICS:
        (A) LENGTH:       38 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:49:
        Leu Pro Thr Thr Leu Ser Phe His Gln Leu Met Leu Gln Met Pro Glu
        5                   10                  15
        Phe Leu Arg Gly Glu Leu Tyr Thr Asn Phe Val Glu Gln Val Met Leu
        20                  25                  30
        Pro Arg Ile Leu Lys Ser
        35

(2) INFORMATION FOR SEQ ID NO:50:

(i) SEQUENCE CHARACTERISTICS:
        (A) LENGTH:       37 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:50:
        Met Lys Phe Asp Lys Ile Leu Ile Ala Asn Arg Gly Glu Ile Ala Leu
        5                   10                  15
        Arg Ile Leu Arg Ala Cys Glu Glu Met Gly Ile Ala Thr Ile Ala Val
        20                  25                  30
        His Ser Thr Val Asp
        35

(2) INFORMATION FOR SEQ ID NO:51:

(i) SEQUENCE CHARACTERISTICS:
        (A) LENGTH:       21 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:51:
        Arg Asn Ala Leu His Val Gln Leu Ala Asp Glu Ala Val Cys Ile Gly
        5                   10                  15
        Glu Pro Ala Ser Ala
        20

(2) INFORMATION FOR SEQ ID NO:52:

(i) SEQUENCE CHARACTERISTICS:
        (A) LENGTH:       38 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:52:
        Lys Ser Tyr Leu Asn Ile Pro Asn Ile Ile Ala Ala Ala Leu Thr Arg
        5                   10                  15
        Asn Ala Ser Ala Ile His Pro Gly Tyr Gly Phe Leu Ser Glu Asn Ala
        20                  25                  30
        Lys Phe Ala Glu Ile Cys
        35

(2) INFORMATION FOR SEQ ID NO:53:

(i) SEQUENCE CHARACTERISTICS:
        (A) LENGTH:       42 amino acids
        (B) TYPE:         Amino acid
        (C) STRANDEDNESS: Single
        (D) TOPOLOGY:     Linear (ii) MOLECULE TYPE:    Peptide (xi) SEQUENCE DESCRIPTION: SEQ ID NO:53:
```

```
        Ala Asp His His Ile Ala Phe Ile Gly Pro Thr Pro Glu Ala Ile Arg
        5                   10                  15
        Leu Met Gly Asp Lys Ser Thr Ala Lys Glu Thr Met Gln Lys Ala Gly
        20                  25                  30
        Val Pro Thr Val Pro Gly Ser Glu Gly Leu
        35                  40
```

(2) INFORMATION FOR SEQ ID NO:54:

(i) SEQUENCE CHARACTERISTICS:
        (A) LENGTH:     142 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:  SEQ ID NO:54:

```
        Val Glu Thr Glu Gln Glu Gly Leu Glu Leu Ala Lys Asp Ile Gly Tyr
        5                   10                  15
        Pro Val Met Ile Lys Ala Thr Ala Gly Gly Gly Arg Gly Met Arg
        20                  25                  30
        Leu Val Arg Ser Pro Asp Glu Phe Val Lys Leu Phe Leu Ala Ala Gln
        35                  40                  45
        Gly Glu Ala Gly Ala Ala Phe Gly Asn Ala Gly Val Tyr Ile Glu Lys
        50                  55                  60
        Phe Ile Glu Arg Pro Arg His Ile Glu Phe Gln Ile Leu Ala Asp Asn
        65                  70                  75                  80
        Tyr Gly Asn Val Ile His Leu Gly Glu Arg Asp Cys Ser Ile Gln Arg
        85                  90                  95
        Arg Asn Gln Lys Leu Leu Glu Glu Ala Pro Ser Pro Ala Leu Asp Ser
        100                 105                 110
        Asp Leu Arg Glu Lys Met Gly Gln Ala Ala Val Lys Ala Ala Gln Phe
        115                 120                 125
        Ile Asn Tyr Ala Gly Ala Gly Thr Ile Glu Phe Leu Leu Asp
        130                 135                 140
```

(2) INFORMATION FOR SEQ ID NO:55:

(i) SEQUENCE CHARACTERISTICS:
        (A) LENGTH:     50 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:  SEQ ID NO:55:

```
        Arg Ser Gly Gln Phe Tyr Phe Met Glu Met Asn Thr Arg Ile Gln Val
        5                   10                  15
        Glu His Pro Val Thr Glu Met Val Thr Gly Val Asp Leu Leu Val Glu
        20                  25                  30
        Gln Ile Arg Ile Ala Gln Gly Glu Arg Leu Arg Leu Thr Gln Asp Gln
        35                  40                  45
        Val Val
        50
```

(2) INFORMATION FOR SEQ ID NO:56:

(i) SEQUENCE CHARACTERISTICS:
        (A) LENGTH:     19 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:  SEQ ID NO:56:

```
        Leu Arg Gly His Ala Ile Glu Cys Arg Ile Asn Ala Glu Asp Pro Asp
        5                   10                  15
        His Asp Phe
```

(2) INFORMATION FOR SEQ ID NO:57:

(i) SEQUENCE CHARACTERISTICS:
        (A) LENGTH:     9 amino acids
        (B) TYPE:       Amino acid
        (C) STRANDEDNESS: Single
        (D) TOPOLOGY:   Linear

```
      (ii) MOLECULE TYPE:      Peptide (xi) SEQUENCE DESCRIPTION: SEQ ID NO:57:
             Arg Pro Ala Pro Gly Arg Ile Ser Gly
             5

(2) INFORMATION FOR SEQ ID NO:58:

(i) SEQUENCE CHARACTERISTICS:
            (A) LENGTH:       6 amino acids
            (B) TYPE:         Amino acid
            (C) STRANDEDNESS: Single
            (D) TOPOLOGY:     Linear (ii) MOLECULE TYPE:      Peptide (xi) SEQUENCE DESCRIPTION: SEQ ID NO:58:
             Tyr Leu Pro Pro Gly Gly
             5

(2) INFORMATION FOR SEQ ID NO:59:

(i) SEQUENCE CHARACTERISTICS:
            (A) LENGTH:       7 amino acids
            (B) TYPE:         Amino acid
            (C) STRANDEDNESS: Single
            (D) TOPOLOGY:     Linear (ii) MOLECULE TYPE:      Peptide (xi) SEQUENCE DESCRIPTION: SEQ ID NO:59:
             Pro Gly Val Arg Ile Asp Ser
             5

(2) INFORMATION FOR SEQ ID NO:60:

(i) SEQUENCE CHARACTERISTICS:
            (A) LENGTH:       44 amino acids
            (B) TYPE:         Amino acid
            (C) STRANDEDNESS: Single
            (D) TOPOLOGY:     Linear (ii) MOLECULE TYPE:      Peptide (xi) SEQUENCE DESCRIPTION: SEQ ID NO:60:
             His Val Tyr Thr Asp Tyr Gln Ile Pro Pro Tyr Tyr Asp Ser Leu Ile
             5                   10                  15
             Gly Lys Leu Ile Val Trp Gly Pro Asp Arg Ala Thr Ala Ile Asn Arg
             20                  25                  30
             Met Lys Arg Ala Leu Arg Glu Cys Ala Ile Thr Gly
             35                  40

(2) INFORMATION FOR SEQ ID NO:61:

(i) SEQUENCE CHARACTERISTICS:
            (A) LENGTH:       154 amino acids
            (B) TYPE:         Amino acid
            (C) STRANDEDNESS: Single
            (D) TOPOLOGY:     Linear (ii) MOLECULE TYPE:      Peptide (xi) SEQUENCE DESCRIPTION: SEQ ID NO:61:
             Leu Pro Thr Thr Ile Gly Phe His Gln Arg Ile Met Glu Asn Pro Gln
             5                   10                  15
             Phe Leu Gln Gly Asn Val Ser Thr Ser Phe Val Gln Glu Met Asn Lys
             20                  25                  30
             Pro Leu Asp Phe Asn Glu Ile Arg Gln Leu Leu Thr Thr Ile Ala Gln
             35                  40                  45
             Thr Asp Ile Ala Glu Val Thr Leu Lys Ser Asp Asp Phe Glu Leu Thr
             50                  55                  60
             Val Arg Lys Ala Val Gly Val Asn Asn Ser Val Pro Val Val Thr
             65                  50                  75                  80
             Ala Pro Leu Ser Gly Val Gly Ser Gly Leu Pro Ser Ala Ile Pro
             85                  90                  95
             Ile Val Ala His Ala Ala Pro Ser Pro Ser Pro Glu Pro Gly Thr Ser
             100                 105                 110
             Arg Ala Ala Asp His Ala Val Thr Ser Ser Gly Ser Gln Pro Gly Ala
             115                 120                 125
             Lys Ile Ile Asp Gln Lys Leu Ala Glu Val Ala Ser Pro Met Val Gly
```

```
                    130                 135                 140
            Thr Phe Tyr Arg Ala Pro Ala Pro Gly Glu
            145                 150
```

(2) INFORMATION FOR SEQ ID NO:62:

(i) SEQUENCE CHARACTERISTICS:
        (A) LENGTH:      24 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:62:

```
            Ala Val Phe Val Glu Val Gly Asp Arg Ile Arg Gln Gly Gln Thr Val
            5                   10                  15
            Cys Ile Ile Glu Ala Met Lys Met
            20
```

(2) INFORMATION FOR SEQ ID NO:63:

(i) SEQUENCE CHARACTERISTICS:
        (A) LENGTH:      36 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:63:

```
            Met Leu Asp Lys Ile Val Ile Ala Asn Arg Gly Glu Ile Ala Leu Arg
            5                   10                  15
            Ile Leu Arg Ala Cys Lys Glu Leu Gly Ile Lys Thr Val Ala Val His
            20                  25                  30
            Ser Ser Ala Asp
            35
```

(2) INFORMATION FOR SEQ ID NO:64:

(i) SEQUENCE CHARACTERISTICS:
        (A) LENGTH:      21 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:64:

```
            Arg Asp Leu Lys His Val Leu Leu Ala Asp Glu Thr Val Cys Ile Gly
            5                   10                  15
            Pro Ala Pro Ser Val
            20
```

(2) INFORMATION FOR SEQ ID NO:65:

(i) SEQUENCE CHARACTERISTICS:
        (A) LENGTH:      38 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:65:

```
            Lys Ser Tyr Leu Asn Ile Pro Ala Ile Ile Ser Ala Ala Glu Ile Thr
            5                   10                  15
            Gly Ala Val Ala Ile His Pro Gly Tyr Gly Phe Leu Ser Glu Asn Ala
            20                  25                  30
            Asn Phe Ala Glu Gln Val
            35
```

(2) INFORMATION FOR SEQ ID NO:66:

(i) SEQUENCE CHARACTERISTICS:
        (A) LENGTH:      43 amino acids
        (B) TYPE:        Amino acid
        (C) STRANDEDNESS: Single
        (D) TOPOLOGY:    Linear

```
    (ii) MOLECULE TYPE:      Peptide (xi) SEQUENCE DESCRIPTION: SEQ ID NO:66:
            Glu Arg Ser Gly Phe Ile Phe Ile Gly Pro Lys Ala Glu Thr Ile Arg
            5                   10                  15
            Leu Met Gly Asp Lys Val Ser Ala Ile Ala Ala Met Lys Lys Ala Gly
            20                  25                  30
            Val Pro Cys Val Pro Gly Ser Asp Gly Pro Leu
            35                  40

(2) INFORMATION FOR SEQ ID NO:67:

(i) SEQUENCE CHARACTERISTICS:
         (A) LENGTH:        141 amino acids
         (B) TYPE:          Amino acid
         (C) STRANDEDNESS: Single
         (D) TOPOLOGY:      Linear (ii) MOLECULE TYPE:      Peptide (xi) SEQUENCE DESCRIPTION: SEQ ID NO:67:
            Gly Asp Asp Met Asp Lys Asn Arg Ala Ile Ala Lys Arg Ile Gly Tyr
            5                   10                  15
            Pro Val Ile Ile Lys Ala Ser Gly Gly Gly Gly Arg Gly Met Arg
            20                  25                  30
            Val Val Arg Gly Asp Ala Glu Leu Ala Gln Ser Ile Ser Met Thr Arg
            35                  40                  45
            Ala Glu Ala Lys Ala Ala Phe Ser Asn Asp Met Val Tyr Met Glu Lys
            50                  55                  60
            Tyr Leu Glu Asn Pro Arg His Val Glu Ile Gln Val Leu Ala Asp Gly
            65                  70                  75                  80
            Gln Gly Asn Ala Ile Tyr Leu Ala Glu Arg Asp Cys Ser Met Gln Arg
            85                  90                  95
            Arg His Gln Lys Val Val Glu Glu Ala Pro Ala Pro Gly Ile Thr Pro
            100                 105                 110
            Glu Leu Arg Arg Tyr Ile Gly Gly Arg Cys Ala Lys Ala Cys Val Asp
            115                 120                 125
            Ile Gly Tyr Arg Gly Ala Gly Thr Phe Glu Phe Leu Phe
            130                 135                 140

(2) INFORMATION FOR SEQ ID NO:68:

(i) SEQUENCE CHARACTERISTICS:
         (A) LENGTH:        50 amino acids
         (B) TYPE:          Amino acid
         (C) STRANDEDNESS: Single
         (D) TOPOLOGY:      Linear (ii) MOLECULE TYPE:      Peptide (xi) SEQUENCE DESCRIPTION: SEQ ID NO:68:
            Glu Asn Gly Glu Phe Tyr Phe Ile Glu Met Asn Thr Arg Ile Gln Val
            5                   10                  15
            Glu His Pro Val Thr Glu Met Ile Thr Gly Val Asp Leu Ile Lys Glu
            20                  25                  30
            Gln Met Arg Ile Ala Ala Gly Gln Pro Leu Ser Ile Lys Gln Glu Glu
            35                  40                  45
            Val His
            50

(2) INFORMATION FOR SEQ ID NO:69:

(i) SEQUENCE CHARACTERISTICS:
         (A) LENGTH:        25 amino acids
         (B) TYPE:          Amino acid
         (C) STRANDEDNESS: Single
         (D) TOPOLOGY:      Linear (ii) MOLECULE TYPE:      Peptide (xi) SEQUENCE DESCRIPTION: SEQ ID NO:69:
            Val Arg Gly His Ala Val Glu Cys Arg Ile Asn Ala Glu Asp Pro Asn
            5                   10                  15
            Leu Pro Ser Pro Gly Lys Ile Thr Arg
            20                  25

(2) INFORMATION FOR SEQ ID NO:70:

(i) SEQUENCE CHARACTERISTICS:
         (A) LENGTH:        6 amino acids
```

```
        (B) TYPE:          Amino acid
        (C) STRANDEDNESS:  Single
        (D) TOPOLOGY:      Linear (ii) MOLECULE TYPE:    Peptide (xi) SEQUENCE DESCRIPTION:  SEQ ID NO:70:
         Phe His Ala Pro Gly Gly
          5

(2) INFORMATION FOR SEQ ID NO:71:

(i) SEQUENCE CHARACTERISTICS:
        (A) LENGTH:        7 amino acids
        (B) TYPE:          Amino acid
        (C) STRANDEDNESS:  Single
        (D) TOPOLOGY:      Linear (ii) MOLECULE TYPE:    Peptide (xi) SEQUENCE DESCRIPTION:  SEQ ID NO:71:
         Phe Gly Val Arg Trp Glu Ser
          5

(2) INFORMATION FOR SEQ ID NO:72:

(i) SEQUENCE CHARACTERISTICS:
        (A) LENGTH:        44 amino acids
        (B) TYPE:          Amino acid
        (C) STRANDEDNESS:  Single
        (D) TOPOLOGY:      Linear (ii) MOLECULE TYPE:    Peptide (xi) SEQUENCE DESCRIPTION:  SEQ ID NO:72:
         His Ile Tyr Ala Gly Tyr Thr Val Pro Pro Tyr Tyr Asp Ser Met Ile
          5                  10                  15
         Gly Lys Leu Ile Cys Tyr Gly Glu Asn Arg Asp Val Ala Ile Ala Arg
          20                  25                  30
         Met Lys Asn Ala Leu Gln Glu Leu Ile Ile Asp Gly
          35                  40

(2) INFORMATION FOR SEQ ID NO:73:

(i) SEQUENCE CHARACTERISTICS:
        (A) LENGTH:        135 amino acids
        (B) TYPE:          Amino acid
        (C) STRANDEDNESS:  Single
        (D) TOPOLOGY:      Linear (ii) MOLECULE TYPE:    Peptide (xi) SEQUENCE DESCRIPTION:  SEQ ID NO:73:
         Ile Lys Thr Asn Val Asp Leu Gln Ile Arg Ile Met Asn Asp Glu Asn
          5                  10                  15
         Phe Gln His Gly Gly Thr Asn Ile His Tyr Leu Glu Lys Lys Leu Gly
          20                  25                  30
         Leu Gln Glu Lys Met Asp Ile Arg Lys Ile Lys Lys Leu Ile Glu Leu
          35                  40                  45
         Val Glu Glu Ser Gly Ile Ser Glu Leu Glu Ile Ser Glu Gly Glu Glu
          50                  55                  60
         Ser Val Arg Ile Ser Arg Ala Ala Pro Ala Ala Ser Phe Pro Val Met
          65                  70                  75                  80
         Gln Gln Ala Tyr Ala Ala Pro Met Met Gln Gln Pro Ala Gln Ser Asn
          85                  90                  95
         Ala Ala Ala Pro Ala Thr Val Pro Ser Met Glu Ala Pro Ala Ala Ala
          100                 105                 110
         Glu Ile Ser Gly His Ile Val Arg Ser Pro Met Val Gly Thr Phe Tyr
          115                 120                 125
         Arg Thr Pro Ser Pro Asp Ala
          130                 135

(2) INFORMATION FOR SEQ ID NO:74:

(i) SEQUENCE CHARACTERISTICS:
        (A) LENGTH:        57 amino acids
        (B) TYPE:          Amino acid
        (C) STRANDEDNESS:  Single
        (D) TOPOLOGY:      Linear
```

```
        (ii) MOLECULE TYPE:        Peptide (xi) SEQUENCE DESCRIPTION:  SEQ ID NO:74:
                Lys Ala Phe Ile Glu Val Gly Gln Lys Val Asn Val Gly Asp Thr Leu
                 5                  10                  15
                Cys Ile Val Glu Ala Met Lys Met Met Asn Gln Ile Glu Ala Asp Lys
                20                  25                  30
                Ser Gly Thr Val Lys Ala Ile Leu Val Glu Ser Gly Gln Pro Val Glu
                35                  40                  45
                Phe Asp Glu Pro Leu Val Val Ile Glu
                50                  55

(2) INFORMATION FOR SEQ ID NO:75:

(i) SEQUENCE CHARACTERISTICS:
             (A) LENGTH:        72 amino acids
             (B) TYPE:          Amino acid
             (C) STRANDEDNESS:  Single
             (D) TOPOLOGY:      Linear (ii) MOLECULE TYPE:        Peptide (xi) SEQUENCE DESCRIPTION:  SEQ ID NO:75:
                Met Leu Ser Ala Ala Leu Arg Thr Leu Lys His Val Leu Tyr Tyr Ser
                 5                  10                  15
                Arg Gln Cys Leu Met Val Ser Arg Asn Leu Gly Ser Val Gly Tyr Asp
                20                  25                  30
                Pro Asn Glu Lys Thr Phe Asp Lys Ile Leu Val Ala Asn Arg Gly Glu
                35                  40                  45
                Ile Ala Cys Arg Val Ile Arg Thr Cys Lys Lys Met Gly Ile Lys Thr
                50                  55                  60
                Val Ala Ile His Ser Asp Val Asp
                65                  70

(2) INFORMATION FOR SEQ ID NO:76:

(i) SEQUENCE CHARACTERISTICS:
             (A) LENGTH:        21 amino acids
             (B) TYPE:          Amino acid
             (C) STRANDEDNESS:  Single
             (D) TOPOLOGY:      Linear (ii) MOLECULE TYPE:        Peptide (xi) SEQUENCE DESCRIPTION:  SEQ ID NO:76:
                Ala Ser Ser Val His Val Lys Met Ala Asp Glu Ala Val Cys Val Gly
                 5                  10                  15
                Pro Ala Pro Thr Ser
                20

(2) INFORMATION FOR SEQ ID NO:77:

(i) SEQUENCE CHARACTERISTICS:
             (A) LENGTH:        38 amino acids
             (B) TYPE:          Amino acid
             (C) STRANDEDNESS:  Single
             (D) TOPOLOGY:      Linear (ii) MOLECULE TYPE:        Peptide (xi) SEQUENCE DESCRIPTION:  SEQ ID NO:77:
                Lys Ser Tyr Leu Asn Met Asp Ala Ile Met Glu Ala Ile Lys Lys Thr
                 5                  10                  15
                Arg Ala Gln Ala Val His Pro Gly Tyr Gly Phe Leu Ser Glu Asn Lys
                20                  25                  30
                Glu Phe Ala Arg Cys Leu
                35

(2) INFORMATION FOR SEQ ID NO:78:

(i) SEQUENCE CHARACTERISTICS:
             (A) LENGTH:        41 amino acids
             (B) TYPE:          Amino acid
             (C) STRANDEDNESS:  Single
             (D) TOPOLOGY:      Linear (ii) MOLECULE TYPE:        Peptide (xi) SEQUENCE DESCRIPTION:  SEQ ID NO:78:
                Ala Ala Glu Asp Val Val Phe Ile Gly Pro Asp Thr His Ala Ile Gln
```

```
                 5              10             15
        Ala Met Gly Asp Lys Ile Glu Ser Lys Leu Leu Ala Lys Lys Ala Glu
         20                  25                  30
        Val Asn Thr Ile Pro Gly Phe Asp Gly
         35                  40
```

(2) INFORMATION FOR SEQ ID NO:79:

(i) SEQUENCE CHARACTERISTICS:
        (A) LENGTH:      144 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:79:

```
            Val Lys Asp Ala Glu Glu Ala Val Arg Ile Ala Arg Glu Ile Gly Tyr
             5                  10                  15
            Pro Val Met Ile Lys Ala Ser Ala Gly Gly Gly Lys Gly Met Arg
             20                  25                  30
            Ile Ala Trp Asp Asp Glu Glu Thr Arg Asp Gly Phe Arg Leu Ser Ser
             35                  40                  45
            Gln Glu Ala Ala Ser Ser Phe Gly Asp Asp Arg Leu Leu Ile Glu Lys
             50                  55                  60
            Phe Ile Asp Asn Pro Arg His Ile Glu Ile Gln Val Leu Gly Asp Lys
             65                  70              75                   80
            His Gly Asn Ala Leu Trp Leu Asn Glu Arg Glu Cys Ser Ile Gln Arg
             85                  90                  95
            Arg Asn Gln Lys Val Val Glu Glu Ala Pro Ser Ile Phe Leu Asp Ala
            100                 105                 110
            Glu Thr Arg Arg Ala Met Gly Glu Gln Ala Val Ala Leu Ala Arg Ala
            115                 120                 125
            Val Lys Tyr Ser Ser Ala Gly Thr Val Glu Phe Leu Val Asp Ser Lys
            130                 135                 140
```

(2) INFORMATION FOR SEQ ID NO:80:

(i) SEQUENCE CHARACTERISTICS:
        (A) LENGTH:      47 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:80:

```
            Lys Asn Phe Tyr Phe Leu Glu Met Asn Thr Arg Leu Gln Val Glu His
             5                  10                  15
            Pro Val Thr Glu Cys Ile His Trp Pro Gly Pro Ser Pro Gly Lys Thr
             20                  25                  30
            Val Leu Gln Glu His Leu Ser Gly Thr Asn Lys Leu Ile Phe Ala
             35                  40                  45
```

(2) INFORMATION FOR SEQ ID NO:81:

(i) SEQUENCE CHARACTERISTICS:
        (A) LENGTH:      29 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:81:

```
            Phe Asn Gly Trp Ala Val Glu Cys Arg Val Tyr Ala Glu Asp Pro Tyr
             5                  10                  15
            Lys Ser Phe Gly Leu Pro Ser Ile Gly Arg Leu Ser Gln
             20                  25
```

(2) INFORMATION FOR SEQ ID NO:82:

(i) SEQUENCE CHARACTERISTICS:
        (A) LENGTH:      14 amino acids
        (B) TYPE:        Amino acid
        (C) STRANDEDNESS: Single
        (D) TOPOLOGY:    Linear (ii) MOLECULE TYPE:    Peptide

```
        (xi) SEQUENCE DESCRIPTION: SEQ ID NO:82:
             Tyr Gln Glu Pro Leu His Leu Pro Gly Val Arg Val Asp Ser
             5                   10

(2) INFORMATION FOR SEQ ID NO:83:

(i) SEQUENCE CHARACTERISTICS:
         (A) LENGTH:        44 amino acids
         (B) TYPE:          Amino acid
         (C) STRANDEDNESS:  Single
         (D) TOPOLOGY:      Linear (ii) MOLECULE TYPE:     Peptide (xi) SEQUENCE DESCRIPTION: SEQ ID NO:83:
             Gly Ile Gln Pro Gly Ser Asp Ile Ser Ile Tyr Tyr Asp Pro Met Ile
             5                   10                  15
             Ser Lys Leu Ile Thr Tyr Gly Ser Asp Arg Thr Glu Ala Leu Lys Arg
             20                  25                  30
             Met Ala Asp Ala Leu Asp Asn Tyr Val Ile Arg Gly
             35                  40

(2) INFORMATION FOR SEQ ID NO:84:

(i) SEQUENCE CHARACTERISTICS:
         (A) LENGTH:        251 amino acids
         (B) TYPE:          Amino acid
         (C) STRANDEDNESS:  Single
         (D) TOPOLOGY:      Linear (ii) MOLECULE TYPE:     Peptide (xi) SEQUENCE DESCRIPTION: SEQ ID NO:84:
             Val Thr His Asn Ile Ala Leu Leu Arg Glu Val Ile Ile Asn Ser Arg
             5                   10                  15
             Phe Val Lys Gly Asp Ile Ser Thr Lys Phe Leu Ser Asp Val Tyr Pro
             20                  25                  30
             Asp Gly Phe Lys Gly His Met Leu Thr Lys Ser Glu Lys Asn Gln Leu
             35                  40                  45
             Leu Ala Ile Ala Ser Ser Leu Phe Val Ala Phe Gln Leu Arg Ala Gln
             50                  55                  60
             His Phe Gln Glu Asn Ser Arg Met Pro Val Ile Lys Pro Asp Ile Ala
             65                  70                  75                  80
             Asn Trp Glu Leu Ser Val Lys Leu His Asp Lys Val His Thr Val Val
             85                  90                  95
             Ala Ser Asn Asn Gly Ser Val Phe Ser Val Glu Val Asp Gly Ser Lys
             100                 105                 110
             Leu Asn Val Thr Ser Thr Trp Asn Leu Ala Ser Pro Leu Leu Ser Val
             115                 120                 125
             Ser Val Asp Gly Thr Gln Arg Thr Val Gln Cys Leu Ser Arg Glu Ala
             130                 135                 140
             Gly Gly Asn Met Ser Ile Gln Phe Leu Gly Thr Val Tyr Lys Val Asn
             145                 150                 155                 160
             Ile Leu Thr Arg Leu Ala Ala Glu Leu Asn Lys Phe Met Leu Glu Lys
             165                 170                 175
             Val Thr Glu Asp Thr Ser Ser Val Leu Arg Ser Pro Met Pro Gly Val
             180                 185                 190
             Val Val Ala Val Ser Val Lys Pro Gly Asp Ala Val Ala Glu Gly Gln
             195                 200                 205
             Glu Ile Cys Val Ile Glu Ala Met Lys Met Gln Asn Ser Met Thr Ala
             210                 215                 220
             Gly Lys Thr Gly Thr Val Lys Ser Val His Cys Gln Ala Gly Asp Thr
             225                 230                 235                 240
             Val Gly Glu Gly Asp Leu Leu Val Glu Leu Glu
             245                 250

(2) INFORMATION FOR SEQ ID NO:85:

(i) SEQUENCE CHARACTERISTICS:
         (A) LENGTH:        90 amino acids
         (B) TYPE:          Amino acid
         (C) STRANDEDNESS:  Single
         (D) TOPOLOGY:      Linear (ii) MOLECULE TYPE:     Peptide (xi) SEQUENCE DESCRIPTION: SEQ ID NO:85:
             Met Pro Tyr Arg Glu Arg Phe Cys Ala Ile Arg Trp Cys Arg Asn Ser
             5                   10                  15
             Gly Arg Ser Ser Gln Gln Leu Leu Trp Thr Leu Lys Arg Ala Pro Val
```

```
                    20                  25                  30
            Tyr Ser Gln Gln Cys Leu Val Val Ser Arg Ser Leu Ser Ser Val Glu
            35                  40                              45
            Tyr Glu Pro Lys Glu Lys Thr Phe Asp Lys Ile Leu Ile Ala Asn Arg
            50                      55                  60
            Gly Glu Ile Ala Cys Arg Val Ile Lys Thr Cys Arg Lys Met Gly Ile
            65                  70                  75                  80
            Arg Thr Val Ala Ile His Ser Asp Val Asp
            85                  90
```

(2) INFORMATION FOR SEQ ID NO:86:

(i) SEQUENCE CHARACTERISTICS:
        (A) LENGTH:      21 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:86:
```
            Ala Ser Ser Val His Val Lys Met Ala Asp Glu Ala Val Cys Val Gly
            5                       10                  15
            Pro Ala Pro Thr Ser
            20
```

(2) INFORMATION FOR SEQ ID NO:87:

(i) SEQUENCE CHARACTERISTICS:
        (A) LENGTH:      38 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:87:
```
            Lys Ser Tyr Leu Asn Met Asp Ala Ile Met Glu Ala Ile Lys Lys Thr
            5                       10                  15
            Gly Ala Gln Ala Val His Pro Gly Tyr Gly Phe Leu Ser Glu Asn Lys
            20                  25                  30
            Glu Phe Ala Lys Cys Leu
            35
```

(2) INFORMATION FOR SEQ ID NO:88:

(i) SEQUENCE CHARACTERISTICS:
        (A) LENGTH:      41 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:88:
```
            Ala Ala Glu Asp Val Thr Phe Ile Gly Pro Asp Thr His Ala Ile Gln
            5                       10                  15
            Ala Met Gly Asp Lys Ile Glu Ser Lys Leu Leu Ala Lys Arg Ala Lys
            20                  25                  30
            Val Asn Thr Ile Pro Gly Phe Asp Gly
            35                  40
```

(2) INFORMATION FOR SEQ ID NO:89:

(i) SEQUENCE CHARACTERISTICS:
        (A) LENGTH:      144 amino acids
        (B) TYPE:        Amino acid
        (C) STRANDEDNESS: Single
        (D) TOPOLOGY:    Linear (ii) MOLECULE TYPE:     Peptide (xi) SEQUENCE DESCRIPTION: SEQ ID NO:89:
```
            Leu Lys Asp Ala Asp Glu Ala Val Arg Ile Ala Arg Glu Ile Gly Tyr
            5                       10                  15
            Pro Val Met Ile Lys Ala Ser Ala Gly Gly Gly Gly Lys Gly Met Arg
            20                  25                  30
            Ile Pro Trp Asp Asp Glu Glu Thr Arg Asp Gly Phe Arg Phe Ser Ser
            35                  40                              45
            Gln Glu Ala Ala Ser Ser Phe Gly Asp Asp Arg Leu Leu Ile Glu Lys
```

```
                50              55                  60
        Phe Ile Asp Asn Pro Arg His Ile Glu Ile Gln Val Leu Gly Asp Lys
        65                  70                  75                  80
        His Gly Asn Ala Leu Trp Leu Asn Glu Arg Glu Cys Ser Ile Gln Arg
                85                  90                  95
        Arg Asn Gln Lys Val Val Glu Glu Ala Pro Ser Ile Phe Leu Asp Pro
        100                 105                 110
        Glu Thr Arg Arg Ala Met Gly Glu Gln Ala Val Ala Trp Pro Lys Ala
        115                 120                 125
        Val Lys Tyr Ser Ser Ala Gly Thr Val Glu Phe Leu Val Asp Ser Gln
        130                 135                 140
```

(2) INFORMATION FOR SEQ ID NO:90:

(i) SEQUENCE CHARACTERISTICS:
        (A) LENGTH:     48 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:   SEQ ID NO:90:

```
        Lys Asn Phe Tyr Phe Leu Glu Met Asn Thr Arg Leu Gln Val Glu His
        5                   10                  15
        Pro Val Thr Glu Cys Ile Thr Gly Leu Asp Leu Val Gln Glu Met Ile
        20                  25                  30
        Leu Val Ala Lys Gly Tyr Pro Leu Arg His Lys Gln Glu Asp Ile Pro
        35                  40                  45
```

(2) INFORMATION FOR SEQ ID NO:91:

(i) SEQUENCE CHARACTERISTICS:
        (A) LENGTH:     29 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:   SEQ ID NO:91:

```
        Ile Ser Gly Trp Ala Val Glu Cys Arg Val Tyr Ala Glu Asp Pro Tyr
        5                   10                  15
        Lys Ser Phe Gly Leu Pro Ser Ile Gly Arg Leu Ser Gln
        20                  25
```

(2) INFORMATION FOR SEQ ID NO:92:

(i) SEQUENCE CHARACTERISTICS:
        (A) LENGTH:     14 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:   SEQ ID NO:92:

```
        Tyr Gln Glu Pro Ile His Leu Pro Gly Val Arg Val Asp Ser
        5                   10
```

(2) INFORMATION FOR SEQ ID NO:93:

(i) SEQUENCE CHARACTERISTICS:
        (A) LENGTH:     44 amino acids
        (B) TYPE:       Amino acid
        (C) STRANDEDNESS: Single
        (D) TOPOLOGY:   Linear (ii) MOLECULE TYPE:     Peptide (xi) SEQUENCE DESCRIPTION:   SEQ ID NO:93:

```
        Gly Ile Gln Pro Gly Ser Asp Ile Ser Ile Tyr His Asp Pro Met Ile
        5                   10                  15
        Ser Lys Leu Val Thr Tyr Gly Ser Asp Arg Ala Glu Ala Leu Lys Arg
        20                  25                  30
        Met Glu Asp Ala Leu Asp Ser Tyr Val Ile Arg Gly
        35                  40
```

(2) INFORMATION FOR SEQ ID NO:94:

```
    (i) SEQUENCE CHARACTERISTICS:
         (A) LENGTH:        251 amino acids
         (B) TYPE:          Amino acid
         (C) STRANDEDNESS:  Single
         (D) TOPOLOGY:      Linear (ii) MOLECULE TYPE:      Peptide (xi) SEQUENCE DESCRIPTION:  SEQ ID NO:94:
         Val Thr His Asn Ile Pro Leu Leu Arg Glu Val Ile Ile Asn Thr Arg
         5                   10                  15
         Phe Val Lys Gly Asp Ile Ser Thr Lys Phe Leu Ser Asp Val Tyr Pro
         20                  25                  30
         Asp Gly Phe Lys Gly His Met Leu Thr Pro Ser Glu Arg Asp Gln Leu
         35                  40                  45
         Leu Ala Ile Ala Ser Ser Leu Phe Val Ala Ser Gln Leu Arg Ala Gln
         50                  55                  60
         Arg Phe Gln Glu His Ser Arg Val Pro Val Ile Arg Pro Asp Val Ala
         65                  70                  75                  80
         Lys Trp Glu Leu Ser Val Lys Leu His Asp Glu Asp His Thr Val Val
         85                  90                  95
         Ala Ser Asn Asn Gly Pro Thr Phe Asn Val Glu Val Asp Gly Ser Lys
         100                 105                 110
         Leu Asn Val Thr Ser Thr Trp Asn Leu Ala Ser Pro Leu Leu Ser Val
         115                 120                 125
         Asn Val Asp Gly Thr Gln Arg Thr Val Gln Cys Leu Ser Pro Asp Ala
         130                 135                 140
         Gly Gly Asn Met Ser Ile Gln Phe Leu Gly Thr Val Tyr Lys Val His
         145                 150                 155                 160
         Ile Leu Thr Lys Leu Ala Ala Glu Leu Asn Lys Phe Met Leu Glu Lys
         165                 170                 175
         Val Pro Lys Asp Thr Ser Ser Val Leu Arg Ser Pro Lys Pro Gly Val
         180                 185                 190
         Val Val Ala Val Ser Val Lys Pro Gly Asp Met Val Ala Glu Gly Gln
         195                 200                 205
         Glu Ile Cys Val Ile Glu Ala Met Lys Met Gln Asn Ser Met Thr Ala
         210                 215                 220
         Gly Lys Met Gly Lys Val Lys Leu Val His Cys Lys Ala Gly Asp Thr
         225                 230                 235                 240
         Val Gly Glu Gly Asp Leu Leu Val Glu Leu Glu
         245                 250

(2) INFORMATION FOR SEQ ID NO:95:

(i) SEQUENCE CHARACTERISTICS:
         (A) LENGTH:        17 amino acids
         (B) TYPE:          Amino acid
         (C) STRANDEDNESS:  Single
         (D) TOPOLOGY:      Linear (ii) MOLECULE TYPE:      Peptide (xi) SEQUENCE DESCRIPTION:  SEQ ID NO:95:
         Gln Arg Lys Phe Ala Gly Leu Arg Asp Asn Phe Asn Leu Leu Gly Glu
         5                   10                  15
         Lys (2) INFORMATION FOR SEQ ID NO:96:

(i) SEQUENCE CHARACTERISTICS:
         (A) LENGTH:        34 amino acids
         (B) TYPE:          Amino acid
         (C) STRANDEDNESS:  Single
         (D) TOPOLOGY:      Linear (ii) MOLECULE TYPE:      Peptide (xi) SEQUENCE DESCRIPTION:  SEQ ID NO:96:
         Asn Lys Ile Leu Val Ala Asn Arg Gly Glu Ile Pro Ile Arg Ile Phe
         5                   10                  15
         Arg Thr Ala His Glu Leu Ser Met Gln Thr Val Ala Ile Tyr Ser His
         20                  25                  30
         Glu Asp (2) INFORMATION FOR SEQ ID NO:97:

(i) SEQUENCE CHARACTERISTICS:
         (A) LENGTH:        24 amino acids
         (B) TYPE:          Amino acid
         (C) STRANDEDNESS:  Single
```

(D) TOPOLOGY:      Linear (ii) MOLECULE TYPE:        Peptide (xi) SEQUENCE DESCRIPTION: SEQ ID NO:97:
            Arg Leu Ser Thr His Lys Gln Lys Ala Asp Glu Ala Tyr Val Ile Gly
            5                   10                  15
            Glu Val Gly Gln Tyr Thr Pro Val
            20

(2) INFORMATION FOR SEQ ID NO:98:

(i) SEQUENCE CHARACTERISTICS:
        (A) LENGTH:        38 amino acids
        (B) TYPE:          Amino acid
        (C) STRANDEDNESS:  Single
        (D) TOPOLOGY:      Linear (ii) MOLECULE TYPE:        Peptide (xi) SEQUENCE DESCRIPTION: SEQ ID NO:98:
            Gly Ala Tyr Leu Ala Ile Asp Glu Ile Ile Ser Ile Ala Gln Lys His
            5                   10                  15
            Gln Val Asp Phe Ile His Pro Gly Tyr Gly Phe Leu Ser Glu Asn Ser
            20                  25                  30
            Glu Phe Ala Asp Lys Val
            35

(2) INFORMATION FOR SEQ ID NO:99:

(i) SEQUENCE CHARACTERISTICS:
        (A) LENGTH:        41 amino acids
        (B) TYPE:          Amino acid
        (C) STRANDEDNESS:  Single
        (D) TOPOLOGY:      Linear (ii) MOLECULE TYPE:        Peptide (xi) SEQUENCE DESCRIPTION: SEQ ID NO:99:
            Val Lys Ala Gly Ile Thr Trp Ile Gly Pro Pro Ala Glu Val Ile Asp
            5                   10                  15
            Ser Val Gly Asp Lys Val Ser Ala Arg Asn Leu Ala Ala Lys Ala Asn
            20                  25                  30
            Val Pro Thr Val Pro Gly Thr Pro Gly
            35                  40

(2) INFORMATION FOR SEQ ID NO:100:

(i) SEQUENCE CHARACTERISTICS:
        (A) LENGTH:        144 amino acids
        (B) TYPE:          Amino acid
        (C) STRANDEDNESS:  Single
        (D) TOPOLOGY:      Linear (ii) MOLECULE TYPE:        Peptide (xi) SEQUENCE DESCRIPTION: SEQ ID NO:100:
            Ile Glu Thr Val Glu Glu Ala Leu Asp Phe Val Asn Glu Tyr Gly Tyr
            5                   10                  15
            Pro Val Ile Ile Lys Ala Ala Phe Gly Gly Gly Gly Arg Gly Met Arg
            20                  25                  30
            Val Val Arg Glu Gly Asp Asp Val Ala Asp Ala Phe Gln Arg Ala Thr
            35                  40                  45
            Ser Glu Ala Arg Thr Ala Phe Gly Asn Gly Thr Cys Phe Val Glu Arg
            50                  55                  60
            Phe Leu Asp Lys Pro Lys His Ile Glu Val Gln Leu Leu Ala Asp Asn
            65                  70                  75                  80
            His Gly Asn Val Val His Leu Phe Glu Arg Asp Cys Ser Val Gln Arg
            85                  90                  95
            Arg His Gln Lys Val Val Glu Val Ala Pro Ala Lys Thr Leu Pro Arg
            100                 105                 110
            Glu Val Arg Asp Ala Ile Leu Thr Asp Ala Val Lys Leu Ala Lys Glu
            115                 120                 125
            Cys Gly Tyr Arg Asn Ala Gly Thr Ala Glu Phe Leu Val Asp Asn Gln
            130                 135                 140

(2) INFORMATION FOR SEQ ID NO:101:

(i) SEQUENCE CHARACTERISTICS:
        (A) LENGTH:        51 amino acids (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:101:
            Asn Arg His Tyr Phe Ile Glu Ile Asn Pro Arg Ile Gln Val Glu His
            5                   10                  15
            Thr Ile Thr Glu Glu Ile Thr Gly Ile Asp Ile Val Ala Ala Gln Ile
            20                  25                  30
            Gln Ile Ala Ala Gly Ala Ser Leu Pro Gln Leu Gly Leu Phe Gln Asp
            35                  40                  45
            Lys Ile Thr
            50

(2) INFORMATION FOR SEQ ID NO:102:

(i) SEQUENCE CHARACTERISTICS:
        (A) LENGTH:        20 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:102:
            Thr Arg Gly Phe Ala Ile Gln Cys Arg Ile Thr Thr Glu Asp Pro Ala
            5                   10                  15
            Lys Asn Phe Gln
            20

(2) INFORMATION FOR SEQ ID NO:103:

(i) SEQUENCE CHARACTERISTICS:
        (A) LENGTH:        14 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:103:
            Pro Asp Thr Gly Arg Ile Glu Val Tyr Arg Ser Ala Gly Gly
            5                   10

(2) INFORMATION FOR SEQ ID NO:104:

(i) SEQUENCE CHARACTERISTICS:
        (A) LENGTH:        52 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:104:
            Asn Gly Val Arg Leu Asp Gly Gly Asn Ala Tyr Ala Gly Thr Ile Ile
            5                   10                  15
            Ser Pro His Tyr Asp Ser Met Leu Val Lys Cys Ser Cys Ser Gly Ser
            20                  25                  30
            Thr Tyr Glu Ile Val Arg Arg Lys Met Ile Arg Ala Leu Ile Glu Phe
            35                  40                  45
            Arg Ile Arg Gly
            50

(2) INFORMATION FOR SEQ ID NO:105:

(i) SEQUENCE CHARACTERISTICS:
        (A) LENGTH:        257 amino acids
        (B) TYPE:          Amino acid
        (C) STRANDEDNESS: Single
        (D) TOPOLOGY:      Linear (ii) MOLECULE TYPE:      Peptide (xi) SEQUENCE DESCRIPTION:  SEQ ID NO:105:
            Val Lys Thr Asn Ile Pro Phe Leu Leu Thr Leu Leu Thr Asn Pro Val
            5                   10                  15
            Phe Ile Glu Gly Thr Tyr Trp Gly Thr Phe Ile Asp Asp Thr Pro Gln

```
            20                  25                  30
        Leu Phe Gln Met Val Ser Ser Gln Asn Arg Ala Gln Lys Leu Leu His
         35                  40                  45
        Tyr Leu Ala Asp Val Ala Asp Asn Gly Ser Ser Ile Lys Gly Gln Ile
         50                  55                  60
        Gly Leu Pro Lys Leu Lys Ser Asn Pro Ser Val Pro His Ser Tyr Asn
         65                  70                  75                  80
        Met Tyr Pro Arg Val Tyr Glu Asp Phe Gln Lys Met Arg Glu Thr Tyr
         85                  90                  95
        Gly Asp Leu Ser Val Leu Pro Thr Arg Ser Phe Leu Ser Pro Leu Glu
        100                 105                 110
        Thr Asp Glu Glu Ile Glu Val Val Ile Glu Gln Gly Lys Thr Leu Ile
        115                 120                 125
        Ile Lys Leu Gln Ala Val Gly Asp Leu Asn Lys Lys Thr Gly Glu Arg
        130                 135                 140
        Glu Val Tyr Phe Asp Leu Asn Gly Glu Met Arg Lys Ile Arg Val Ala
        145                 150                 155                 160
        Asp Arg Ser Gln Lys Val Glu Thr Val Thr Lys Ser Lys Ala Asp Met
        165                 170                 175
        His Asp Pro Leu His Ile Gly Ala Pro Met Ala Gly Val Ile Val Glu
        180                 185                 190
        Val Lys Val His Lys Gly Ser Leu Ile Lys Lys Gly Gln Pro Val Ala
        195                 200                 205
        Val Leu Ser Ala Met Lys Met Glu Met Ile Ile Ser Ser Pro Ser Asp
        210                 215                 220
        Gly Gln Val Lys Glu Val Phe Val Ser Asp Gly Glu Asn Val Asp Ser
        225                 230                 235                 240
        Ser Asp Leu Leu Val Leu Leu Glu Asp Gln Val Pro Val Glu Thr Lys
        245                 250                 255
        Ala
```

(2) INFORMATION FOR SEQ ID NO:106:

(i) SEQUENCE CHARACTERISTICS:
        (A) LENGTH:       165 amino acids
        (B) TYPE:         Amino acid
        (C) STRANDEDNESS: Single
        (D) TOPOLOGY:     Linear (ii) MOLECULE TYPE:     Peptide (xi) SEQUENCE DESCRIPTION: SEQ ID NO:106:

```
        Val Leu Thr Val Ala Leu Phe Pro Gln Pro Gly Leu Lys Phe Leu Glu
         5                   10                  15
        Asn Arg His Asn Pro Ala Ala Phe Glu Pro Val Pro Gln Ala Glu Ala
         20                  25                  30
        Ala Gln Pro Val Ala Lys Ala Glu Lys Pro Ala Ala Ser Gly Val Tyr
         35                  40                  45
        Thr Val Glu Val Glu Gly Lys Ala Phe Val Lys Val Ser Asp Gly
         50                  55                  60
        Gly Asp Val Ser Gln Leu Thr Ala Ala Pro Ala Pro Ala Pro Ala
         65                  70                  75                  80
        Pro Ala Pro Ala Ser Ala Pro Ala Ala Ala Pro Ala Gly Ala Gly
         85                  90                  95
        Thr Pro Val Thr Ala Pro Leu Ala Gly Thr Ile Trp Lys Val Leu Ala
        100                 105                 110
        Ser Glu Gly Gln Thr Val Ala Ala Gly Glu Val Leu Leu Ile Leu Glu
        115                 120                 125
        Ala Met Lys Met Glu Thr Glu Ile Arg Ala Ala Gln Ala Gly Thr Val
        130                 135                 140
        Arg Gly Ile Ala Val Lys Ala Gly Asp Ala Val Ala Val Gly Asp Thr
        145                 150                 155                 160
        Leu Met Thr Leu Ala
        165
```

(2) INFORMATION FOR SEQ ID NO:107:

(i) SEQUENCE CHARACTERISTICS:
        (A) LENGTH:       123 amino acids
        (B) TYPE:         Amino acid
        (C) STRANDEDNESS: Single
        (D) TOPOLOGY:     Linear (ii) MOLECULE TYPE:     Peptide (xi) SEQUENCE DESCRIPTION: SEQ ID NO:107:

```
        Met Lys Leu Lys Val Thr Val Asn Gly Thr Ala Tyr Asp Val Asp Val
         5                   10                  15
        Asp Val Asp Lys Ser His Glu Asn Pro Met Gly Thr Ile Leu Phe Gly
         20                  25                  30
```

```
            Gly Gly Thr Gly Gly Ala Pro Ala Pro Arg Ala Ala Gly Gly Ala Gly
             35                  40                  45
            Ala Gly Lys Ala Gly Glu Gly Glu Ile Pro Ala Pro Leu Ala Gly Thr
             50                  55                  60
            Val Ser Lys Ile Leu Val Lys Glu Gly Asp Thr Val Lys Ala Gly Gln
             65                  70                  75                  80
            Thr Val Leu Val Leu Glu Ala Met Lys Met Glu Thr Glu Ile Asn Ala
                 85                  90                  95
            Pro Thr Asp Gly Lys Val Glu Lys Val Leu Val Lys Glu Arg Asp Ala
            100                 105                 110
            Val Gln Gly Gly Gln Gly Leu Ile Lys Ile Gly
            115                 120

(2) INFORMATION FOR SEQ ID NO:108:

(i) SEQUENCE CHARACTERISTICS:
        (A) LENGTH:       1473 base pairs
        (B) TYPE:         Nucleic acid
        (C) STRANDEDNESS: Single
        (D) TOPOLOGY:     Linear (ii) MOLECULE TYPE:    Oligonucleotide (xi) SEQUENCE DESCRIPTION:  SEQ ID NO:108:
            GTGATGATCA AGGCATCATG GGGTGGGGGT GGTAAAGGAA TAAGGAAGGT ACATAATGAT   60
            GATGAGGTCA GAGCATTGTT TAAGCAAGTG CAAGGAGAAG TCCCCGGATC GCCTATATTT  120
            ATTATGAAGG TGGCATCTCA GAGTCGACAT CTAGAGGTTC AATTGCTCTG TGACAAGCAT  180
            GGCAACGTGG CAGCACTGCA CAGTCGAGAC TGTAGTGTTC AAAGAAGGCA TCAAAAGATC  240
            ATTGAGGAGG GACCAATTAC AGTTGCTCCT CCAGAAACAA TTAAAGAGCT TGAGCAGGCG  300
            GCAAGGCGAC TAGCTAAATG TGTGCAATAT CAGGGTGCTG CTACAGTGGA ATATCTGTAC  360
            AGCATGGAAA CAGGCGAATA CTATTTCCTG GAGCTTAATC CAAGGTTGCA GGTAGAACAC  420
            CCTGTGACCG AATGGATTGC TGAAATAAAC TTACCYGCAT CTCAAGTTGT AGTAGGAATG  480
            GGCATACCAC TCTACAACAT TCCAGAGATC AGACGCTTTT ATGGAATAGA ACATGGAGGT  540
            GGCTATCAYG CTTGGAAGGA AATATCAGCT GTTGCAACTA AATTTGATYT GGACAAAGCA  600
            CAGTCTGTAA AGCCAAARGG TCATTGTGTA GCAGTTAGAG TTACTAGCGA GGATCCAGAT  660
            GATGGGTTTA AGCCTACMAG TGGAAGAGTR GAAGAGCTGA ACTTTAAAAG TAAACCCAAT  720
            GTTTGGGCCT ATTTCTCYGT TARGTCCGGA GGTGCAATTC AYGAGTTCTC TGATTCCCAG  780
            TTTGGTCATG TTTTTGCTTY TGGGGAATCT AGGTCWTTGG CAATAGCCAA TATGGTACTT  840
            GGGTTAAAAG AGATCCAAAT TCGTGGAGAG ATACGCACTA ATGTTGACTA CACTGTGGAT  900
            CTCTTGAATG CTGCAGAGTA CCGAGAAAAT AWGATTCACA CTGGTTGGCT AGACAGCAGA  960
            ATAGCWATGC GYGTTAGAGC AGAGAGGCCC CCATGGTACC TTTCAGTTGT TGGTGGAGCT 1020
            CTATATGAAG CATCAAGCAG GAGCTCGAGT GTTGTAACCG ATTATGTTGG TTATCTCAGT 1080
            AAAGGTCAAA TACCACCAAA GCACATCTCT CTTGTCAAYT TGACTGTAAC ACTGAATATA 1140
            GATGGGAGCA AATATACGAT TGAGACAGTA CGAGGTGGAC CCCGTAGCTA CAAATTAAGA 1200
            ATTAATGAAT CAGAGGTTGA RGCAGAGATA CATTTCCTGC GGATGGCGG ACYCTTAATG 1260
            CAGTYGGATG GAAACAGTCA TGTAATTTAC GCCGAGACAG AAGCTKCTGG CACGCGCCTT 1320
            CTAATCAATG GGAGAACATG CTTATTACAG AAAGAGCAYG ATCCTTCCAG GTTGTTGGCT 1380
            GATACACCRT GCAARCTTCT TCGGTTTTTG GTCGCGGATR GTTCTCATGT GGTTGCTGAT 1440
            ACGCCATATG CYGAGGTGGA GGCCATGAAA ATG                              1473

(2) INFORMATION FOR SEQ ID NO:109:

(i) SEQUENCE CHARACTERISTICS:
        (A) LENGTH:       491 amino acids
        (B) TYPE:         Amino acid
        (C) STRANDEDNESS: Single
        (D) TOPOLOGY:     Linear (ii) MOLECULE TYPE:    Peptide (ix) FEATURE:
        (A) NAME/KEY: Xaa
        (B) LOCATION: 248, 267, 311, 412, 418, 422, 436, and 474
        (C) IDENTIFICATION METHOD:  Xaa = any amino acid (xi) SEQUENCE DESCRIPTION:  SEQ ID NO:109:
            Val Met Ile Lys Ala Ser Trp Gly Gly Gly Lys Gly Ile Arg Lys
              5                  10                  15
            Val His Asn Asp Asp Glu Val Arg Ala Leu Phe Lys Gln Val Gln Gly
             20                  25                  30
            Glu Val Pro Gly Ser Pro Ile Phe Ile Met Lys Val Ala Ser Gln Ser
             35                  40                  45
            Arg His Leu Glu Val Gln Leu Leu Cys Asp Lys His Gly Asn Val Ala
             50                  55                  60
            Ala Leu His Ser Arg Asp Cys Ser Val Gln Arg Arg His Gln Lys Ile
             65                  70                  75                  80
            Ile Glu Glu Gly Pro Ile Thr Val Ala Pro Glu Thr Ile Lys Glu
                 85                  90                  95
            Leu Glu Gln Ala Ala Arg Arg Leu Ala Lys Cys Val Gln Tyr Gln Gly
            100                 105                 110
```

```
              Ala Ala Thr Val Glu Tyr Leu Tyr Ser Met Glu Thr Gly Tyr Tyr
              115                 120                 125
              Phe Leu Glu Leu Asn Pro Arg Leu Gln Val Glu His Pro Val Thr Glu
              130                 135                 140
              Trp Ile Ala Glu Ile Asn Leu Pro Ala Ser Gln Val Val Val Gly Met
              145                 150                 155                 160
              Gly Ile Pro Leu Tyr Asn Ile Pro Glu Ile Arg Arg Phe Tyr Gly Ile
              165                 170                 175
              Glu His Gly Gly Gly Tyr His Ala Trp Lys Glu Ile Ser Ala Val Ala
              180                 185                 190
              Thr Lys Phe Asp Leu Asp Lys Ala Gln Ser Val Lys Pro Lys Gly His
              195                 200                 205
              Cys Val Ala Val Arg Val Thr Ser Glu Asp Pro Asp Asp Gly Phe Lys
              210                 215                 220
              Pro Thr Ser Gly Arg Val Glu Glu Leu Asn Phe Lys Ser Lys Pro Asn
              225                 230                 235                 240
              Val Trp Ala Tyr Phe Ser Val Xaa Ser Gly Gly Ala Ile His Glu Phe
              245                 250                 255
              Ser Asp Ser Gln Phe Gly His Val Phe Ala Xaa Gly Glu Ser Arg Ser
              260                 265                 270
              Leu Ala Ile Ala Asn Met Val Leu Gly Leu Lys Glu Ile Gln Ile Arg
              275                 280                 285
              Gly Glu Ile Arg Thr Asn Val Asp Tyr Thr Val Asp Leu Leu Asn Ala
              290                 295                 300
              Ala Glu Tyr Arg Glu Asn Xaa Ile His Thr Gly Trp Leu Asp Ser Arg
              305                 310                 315                 320
              Ile Ala Met Arg Val Arg Ala Glu Arg Pro Pro Trp Tyr Leu Ser Val
              325                 330                 335
              Val Gly Ala Leu Tyr Glu Ala Ser Ser Arg Ser Ser Ser Val Val
              340                 345                 350
              Thr Asp Tyr Val Gly Tyr Leu Ser Lys Gly Gln Ile Pro Pro Lys His
              355                 360                 365
              Ile Ser Leu Val Asn Leu Thr Val Thr Leu Asn Ile Asp Gly Ser Lys
              370                 375                 380
              Tyr Thr Ile Glu Thr Val Arg Gly Gly Pro Arg Ser Tyr Lys Leu Arg
              385                 390                 395                 400
              Ile Asn Glu Ser Glu Val Glu Ala Glu Ile His Xaa Leu Arg Asp Gly
              405                 410                 415
              Gly Xaa Leu Met Gln Xaa Asp Gly Asn Ser His Val Ile Tyr Ala Glu
              420                 425                 430
              Thr Glu Ala Xaa Gly Thr Arg Leu Leu Ile Asn Gly Arg Thr Cys Leu
              435                 440                 445
              Leu Gln Lys Glu His Asp Pro Ser Arg Leu Leu Ala Asp Thr Pro Cys
              450                 455                 460
              Lys Leu Leu Arg Phe Leu Val Ala Asp Xaa Ser His Val Val Ala Asp
              465                 470                 475                 480
              Thr Pro Tyr Ala Glu Val Glu Ala Met Lys Met
              485                 490
```

(2) INFORMATION FOR SEQ ID NO:110:

(i) SEQUENCE CHARACTERISTICS:
        (A) LENGTH:      436 base pairs
        (B) TYPE:        Nucleic acid
        (C) STRANDEDNESS: Single
        (D) TOPOLOGY:    Linear (ii) MOLECULE TYPE:    Oligonucleotide (xi) SEQUENCE DESCRIPTION: SEQ ID NO:110:

```
              TCTAGACTTT AACGAGATTC GTCAACTGCT GACAACTATT GCACAAACAG ATATCGCGGA      60
              AGTAACGCTC AAAAGTGATG ATTTTGAACT AACGGTGCGT AAAGCTGTTG GTGTGAATAA     120
              TAGTGTTGTG CCGGTTGTGA CAGCACCCTT GAGTGGTGTG GTAGGTTCGG GATTGCCATC     180
              GGCTATACCG ATTGTAGCCC ATGCTGCCCA ATCTCCATCT CCAGAGCCGG GAACAAGCCG     240
              TGCTGCTGAT CATGCTGTCA CGAGTTCTGG CTCACAGCCA GGAGCAAAAA TCATTGACCA     300
              AAAATTAGCA GAAGTGGCTT CCCCAATGGT GGGAACATTT TACCGCGCTC CTGCACCAGG     360
              TGAAGCGGTA TTTGTGGAAG TCGGCGATCG CATCCGTCAA GGTCAAACCG TCTGCATCAT     420
              CGAAGCGATG AAAAUG                                                     436
```

(2) INFORMATION FOR SEQ ID NO:111:

(i) SEQUENCE CHARACTERISTICS:
        (A) LENGTH:      145 amino acids
        (B) TYPE:        Amino acid
        (C) STRANDEDNESS: Single
        (D) TOPOLOGY:    Linear (ii) MOLECULE TYPE:    Peptide (xi) SEQUENCE DESCRIPTION: SEQ ID NO:111:

```
            Leu Asp Phe Asn Glu Ile Arg Gln Leu Leu Thr Thr Ile Ala Gln Thr
            5                   10                  15
            Asp Ile Ala Glu Val Thr Leu Lys Ser Asp Asp Phe Glu Leu Thr Val
            20                  25                  30
            Arg Lys Ala Val Gly Val Asn Asn Ser Val Val Pro Val Val Thr Ala
            35                  40                  45
            Pro Leu Ser Gly Val Val Gly Ser Gly Leu Pro Ser Ala Ile Pro Ile
            50                  55                  60
            Val Ala His Ala Ala Pro Ser Pro Ser Pro Glu Pro Gly Thr Ser Arg
            65                  70                  75                  80
            Ala Ala Asp His Ala Val Thr Ser Ser Gly Ser Gln Pro Gly Ala Lys
            85                  90                  95
            Ile Ile Asp Gln Lys Leu Ala Glu Val Ala Ser Pro Met Val Gly Thr
            100                 105                 110
            Phe Tyr Arg Ala Pro Ala Pro Gly Glu Ala Val Phe Val Glu Val Gly
            115                 120                 125
            Asp Arg Ile Arg Gln Gly Gln Thr Val Cys Ile Ile Glu Ala Met Lys
            130                 135                 140
            Met
            145
```

(2) INFORMATION FOR SEQ ID NO:112:

(i) SEQUENCE CHARACTERISTICS:
        (A) LENGTH:     22 base units
        (B) TYPE:       Nucleic acid
        (C) STRANDEDNESS: Single
        (D) TOPOLOGY:   Linear (ii) MOLECULE TYPE:    Oligonucleotide (ix) FEATURE:
        (A) NAME/KEY: N
        (B) LOCATION: 11, 14
        (C) IDENTIFICATION METHOD:  N = A, G, C, T (xi) SEQUENCE DESCRIPTION: SEQ ID NO:112:
        TCGAATTCGT NATNATHAAR GC                                     22

(2) INFORMATION FOR SEQ ID NO:113:

(i) SEQUENCE CHARACTERISTICS:
        (A) LENGTH:     22 base pairs
        (B) TYPE:       Nucleic acid
        (C) STRANDEDNESS: Single
        (D) TOPOLOGY:   Linear (ii) MOLECULE TYPE:    Oligonucleotide (ix) FEATURE:
        (A) NAME/KEY: N
        (B) LOCATION: 17
        (C) IDENTIFICATION METHOD:  N = A, G, C, T (xi) SEQUENCE DESCRIPTION: SEQ ID NO:113:
        GCTCTAGAGK RTGYTCNACY TC                                     22

(2) INFORMATION FOR SEQ ID NO:114:

(i) SEQUENCE CHARACTERISTICS:
        (A) LENGTH:     21 base pairs
        (B) TYPE:       Nucleic acid
        (C) STRANDEDNESS: Single
        (D) TOPOLOGY:   Linear (ii) MOLECULE TYPE:    Oligonucleotide (xi) SEQUENCE DESCRIPTION: SEQ ID NO:114:
        GCTCTAGAAT ACTATTTCCT G                                        21

(2) INFORMATION FOR SEQ ID NO:115:

(i) SEQUENCE CHARACTERISTICS:
        (A) LENGTH:     22 base pairs
        (B) TYPE:       Nucleic acid
        (C) STRANDEDNESS: Single
        (D) TOPOLOGY:   Linear (ii) MOLECULE TYPE:    Oligonucleotide

```
    (ix) FEATURE:
          (A) NAME/KEY:  N
          (B) LOCATION:  10, 20
          (C) IDENTIFICATION METHOD:  N = A, G, C, T (xi) SEQUENCE DESCRIPTION:  SEQ ID NO:115:
         TCGAATTCWN CATYTTCATN RC                                              22

(2) INFORMATION FOR SEQ ID NO:116:

(i) SEQUENCE CHARACTERISTICS:
          (A) LENGTH:       23 base pairs
          (B) TYPE:         Nucleic acid
          (C) STRANDEDNESS: Single
          (D) TOPOLOGY:     Linear (ii) MOLECULE TYPE:     Oligonucleotide (xi) SEQUENCE DESCRIPTION:  SEQ ID NO:116:
         GCTCTAGAYT TYAAYGARAT HMG                                             23
```

CYANOBACTERIAL AND PLANT ACETYL-COA CARBOXYLASE

This is a divisional of application Ser. No. 07/956,700 filed Oct. 2, 1992, U.S. Pat. No. 5,539,092.

The United States Government has certain rights in the present invention pursuant to Grant No. 90-34190-5207 from the United States Department of Agriculture through the midwest biotechnology consortium.

TECHNICAL FIELD OF THE INVENTION

The present invention relates to polynucleotides and polypeptides of acetyl-CoA carboxylase in cyanobacteria and plants. Polynucleotides encoding acetyl-CoA carboxylase have use in conferring herbicide resistance and in determining the herbicide resistance of plants in a breeding program.

BACKGROUND OF THE INVENTION

Acetyl-CoA carboxylase (ACC) is the first enzyme of the biosynthetic pathway to fatty acids. It belongs to a group of carboxylases that use biotin as cofactor and bicarbonate as a source of the carboxyl group. ACC catalyzes the addition of $CO_2$ to acetyl-CoA to yield malonyl-CoA in two steps as shown below.

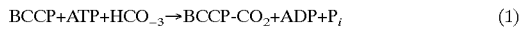

$$BCCP+ATP+HCO_3^- \rightarrow BCCP\text{-}CO_2+ADP+P_i \quad (1)$$

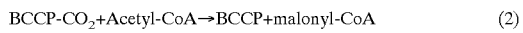

$$BCCP\text{-}CO_2+Acetyl\text{-}CoA \rightarrow BCCP+malonyl\text{-}CoA \quad (2)$$

Fist, biotin becomes carboxylated at the expense of ATP. The carboxyl group is then transferred to Ac-CoA [Knowles, 1989]. This irreversible reaction is the committed step in fatty acid synthesis and is a target for multiple regulatory mechanisms. Reaction (1) is catalyzed by biotin carboxylase (BC); reaction (2) by transcarboxylase (TC); BCCP=biotin carboxyl carrier protein.

ACC purified from *E.coli* contains three distinct, separable components.: biotin carboxylase (BC), a dimer of 49-kD monomers, biotin carboxyl carrier protein (BCCP) a dimer of 17-kD monomers and transcarboxylase (TC), a tetramer containing two each of 33-kD and 35-kD subunits. The biotin prosthetic group is covalently attached to the γ-amino group of a lysine residue of BCCP. The primary structure of *E. coli* BCCP and BC is known (fabE and fabG genes, respectively, have been cloned and sequenced) [Alix, 1989; Maramatsu, et al., 1989; Li, et al., 1992]. In bacteria, fatty acids are primarily precursors of phospholipids rather than storage fuels, and so ACC activity is coordinated with cell growth and division.

Rat and chicken ACC consist of a dimer of about 265 kD (rat has also a 280 kD isoform) subunits that contains all of the bacterial enzyme activities. Both mammalian and avian ACC are cytoplasmic enzymes and their substrate is transported out of mitochondria via citrate. ACC content and/or activity varies with the rate of fatty acid synthesis or energy requirements in different nutritional, hormonal and developmental states. ACC mRNA is transcribed using different promoters and can be regulated by alternative splicing. ACC catalytic activity is regulated allosterically by a number of metabolites and by reversible phospriorylation of the enzyme. The primary structure of rat and chicken enzymes, and the primary structure of the 5'-untranslated region of mRNA have been deduced from cDNA sequences [Lopez-Casillas, et al., 1988; Takai, et al., 1988]. The primary structure of yeast ACC has also been determined [Feel, et al., 1992].

Studies on plant ACC are far less advanced [Harwood, 1988]. It was originally thought that plant ACC consisted of low molecular weight dissociable subunits similar to those of bacteria. Those results appeared to be due to degradation of the enzyme during purification. More recent results indicate that the wheat enzyme, as well as those from parsley and rape, are composed of two about 220 kD monomers, similar to the enzyme from rat and chicken [Harwood, 1988; Egin-Buhler, et al., 1983; Wurtelle, et al., 1990; Slabas, et al., 1985]. The plant ACC is located entirely in the stroma of plastids, where all plant fatty acid synthesis occurs. No plant gene encoding ACC has been reported to date. The gene must be nuclear because no corresponding sequence is seen in the complete chloroplast DNA sequences of tobacco, liverwort or rice. ACC, like the vast majority of chloroplast proteins which are encoded in nuclear DNA, must be synthesized in the cytoplasm and then transported into the chloroplast, probably requiring a chloroplast transport sequence. Although the basic features of plant ACC must be the same as those of prokaryotic and other eucaryotic ACCs, significant differences can be also expected due, for example, to differences in plant cell metabolism and ACC cellular localization.

Structural similarities deduced from the available amino acid sequences suggest strong evolutionary conservation among biotin carboxylases and biotin carboxylase domains of all biotin-dependent carboxylases. On the contrary, the BCCP domains show very little conservation outside the sequence E(A/V)MKM (lysine residue is biotinylated) which is found in all biotinylated proteins including pyruvate carboxylase and propionyl-CoA carboxylase [Knowles, 1989; Samols, et al., 1988]. It is likely that the three functional domains of ACC located in *E.coli* on separate polypeptides are present in carboxylases containing two (human propionyl-CoA carboxylase) or only one (yeast pyruvate carboxylase, mammalian, avian and probably also plant ACC) polypeptide as a result of gene fusion during evolution.

Several years ago it was shown that aryloxyphenoxypropionates and cyclohexanediones, powerful herbicides effective against monocot weeds, inhibit fatty acid biosynthesis in sensitive plants. Recently it has been determined that ACC is the target enzyme for both of these classes of herbicide. Dicotyledonous plants are resistant to these compounds, as are other eukaryotes and prokaryotes. The mechanisms of inhibition and resistance of the enzyme are not known [Lichtenthaler, 1990].

It has occurred to others that the evolutionary relatedness of cyanobacteria and plants make the former useful sources of cloned genes for the isolation of plant cDNAs. For example, Pecker et al used the cloned gene for the enzyme phytoene desaturase, which functions in the synthesis of carotenoids, from cyanobacteria as a probe to isolate the cDNA for that gene from tomato [Pecker, et al., 1992].

BRIEF SUMMARY OF THE INVENTION

In one aspect the present invention provides an isolated and purified polynucleotide of from about 1350 to about 40,000 base pairs that encodes a polypeptide having the ability to catalyze the carboxylation of a biotin carboxyl carrier protein of a cyanobacterium. Preferably, that polypeptide is a subunit of acetyl-CoA carboxylase and participates in the carboxylation of acetyl-CoA. In a preferred embodiment, a cyanobacterium is Anabaena or Synechococcus. The biotin carboxyl carrier protein preferably includes the amino acid residue sequence shown in SEQ ID NO:111 or a functional equivalent thereof.

In another preferred embodiment, the polypeptide has the amino acid residue sequence of FIG. 1 or FIG. 2. The polynucleotide preferably includes the DNA sequence of SEQ ID NO:1, the DNA sequence of SEQ ID NO:1 from about nucleotide position 1300 to about nucleotide position 2650 or the DNA sequence of SEQ ID NO:5.

In another aspect, the present invention provides an isolated and purified polynucleotide of from about 480 to about 40,000 base pairs that encodes a biotin carboxyl carrier protein of a cyanobacterium and, preferably Anabaena. The biotin carboxyl carrier protein preferably includes the amino acid residue sequence of SEQ ID NO:111 and the polynucleotide preferably includes the DNA sequence of SEQ ID NO:110.

Another polynucleotide provided by the present invention encodes a plant polypeptide having the ability to catalyze the carboxylation of acetyl-CoA. A plant polypeptide is preferably (1) a monocotyledonous plant polypeptide such as a wheat, rice, maize, barley, rye, oats or timothy grass polypeptide or (2) a dicotyledonous plant polypeptide such as a soybean, rape, sunflower, tobacco, Arabiodopsis, petunia, Canola, pea, bean, tomato, potato, lettuce, spinach, alfalfa, cotton or carrot polypeptide. Preferably, that polypeptide is a subunit of ACC and participates ih the carboxylation of acetyl-CoA.

Such a polynucleotide preferably includes the nucleotide sequence of SEQ ID NO:108 and encodes the amino acid residue sequence of SEQ ID NO:109.

In yet another aspect, the present invention provides an isolated and purified DNA molecule comprising a promoter operatively linked to a coding region that encodes (1) a polypeptide having the ability to catalyze the carboxylation of a biotin carboxyl carrier protein of a cyanobacterium, (2) a biotin carboxyl carrier protein of a cyanobacterium or (3) a plant polypeptide having the ability to catalyze the carboxylation of acetyl-CoA, which coding region is operatively linked to a transcription-terminating region, whereby said promoter drives the transcription of said coding region.

In another aspect, the present invention provides an isolated polypeptide having the ability to catalyze the carboxylation of a biotin carboxyl carrier protein of a cyanobacterium such as Anabaena or Synechococcus. Preferably a biotin carboxyl carrier protein includes the amino acid sequence of SEQ ID NO:111 and the polypeptide has the amino acid residue sequence of FIG. 1 or FIG. 2 (SEQ ID NO:5 and SEQ ID NO:6).

The present invention also provides (1) an isolated and purified biotin carboxyl carrier protein of a cyanobacterium such as Anabaena, which protein includes the amino acid residue sequence of SEQ ID NO:111 and (2) an isolated and purified plant polypeptide having a molecular weight of about 220 kD, dimers of which have the ability to catalyze the carboxylation of acetyl-CoA.

In yet another aspect, the present invention provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a polypeptide is an acetyl-CoA carboxylase enzyme and, more preferably, a dicotyledonous plant acetyl-CoA carboxylase. In a preferred embodiment, a coding region includes the DNA sequence of SEQ ID NO:108 and a promoter is CaMV35.

The present invention also provides a transformed plant produced in accordance with the above process as well as a transgenic plant and a transgenic plant seed having incorporated into its genome a transgene that encodes a herbicide resistant polypeptide having the ability to catalyze the carboxylation of acetyl-CoA.

In yet another aspect, the present invention provides a process of altering the carboxylation of acetyl-CoA in a cell comprising transforming the cell with a DNA molecule comprising a promoter operatively linked to a coding region that encodes a plant polypeptide having the ability to catalyze the carboxylation of acetyl-CoA, which coding region is operatively linked to a transcription-terminating region, whereby the promoter is capable of driving the transcription of the coding region in the cell.

In a preferred embodiment, a cell is a cyanobacterium or a plant cell and a plant polypeptide is a monocotyledonous plant acetyl-CoA carboxylase enzyme such as wheat acetyl-CoA carboxylase enzyme. The present invention also provides a transformed cyanobacterium produced in accordance with such a process.

The present invention still further provides a process for determining the inheritance of plant resistance to herbicides of the aryloxyphenocypropionate or cyclohexanedione class, which process comprises the steps of:

(a) measuring resistance to herbicides of the aryloxyphenocypropionate or cyclohexanedione class in a parental plant line and in progeny of the parental plant line;

(b) purifying DNA from said parental plant line and the progeny;

(c) digesting the DNA with restriction enzymes to form DNA fragments;

(d) fractionating the fragments on a gel;

(e) transferring the fragments to a filter support;

(f) annealing the fragments with a labelled RFLP probe consisting of a DNA molecule that encodes acetyl-CoA carboxylase or a portion thereof; and (g) detecting the presence of complexes between the fragments and the RFLP probe; and (h) correlating the herbicide resistance of step (a) with the complexes of step (g) and thereby the inheritance of herbicide resistance.

Preferably, the acetyl-CoA carboxylase is a dicotyledonous plant acetyl-CoA carboxylase enzyme or a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

In still yet another aspect, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed cyanobacteria;

(b) inactivating cyanobacterial acetyl-CoA carboxylase;

(c) exposing the transformed cyanobacteria to a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

BRIEF DESCRIPTION OF THE DRAWINGS

In the drawings which form a portion of the specification:

FIG. 1A and FIG. 1B shows the complete nucleotide sequence (SEQ ID NO:1) of a HindIII fragment that includes the fabG gene coding biotin carboxylase from the cyanobacterium Anabaena 7120, along with the amino acid sequence (SEQ ID NOS:2–4) deduced from the coding sequence of the DNA.

FIG. 2A and FIG. 2B shows the nucleotide sequence (SEQ ID NO:5) of the coding region of the fabG gene from the cyanobacterium *Anacystis nidulans* R2, along with the amino acid sequence (SEQ ID NO:6) deduced from the coding sequence of the DNA.

FIG. 3A, FIG. 3B, FIG. 3C, FIG. 3D, FIG. 3E, and FIG. 3F shows an alignment of the amino acid sequences (SEQ ID NOS:6–107 and 109) of the BC proteins from both cyanobacteria and from *E. coli*, the BCCP proteins from Anabaena and from *E. coli*, along with the ACC enzymes from rat and chicken and several other biotin-containing carboxylases. Stars indicate positions that are identical in all sequences or all but one. The conventional one letter abbreviations for amino acids are used. The BC domains are indicated by a solid underline, the BCCP domains by a dashed underline. The symbol # indicates sequences not related to BC and, therefore, not considered in the alignment. The wheat ACC sequence deduced from the sequence of our cloned cDNA fragment is on the top line. Abbreviations used in the Figure are: Wh ACC, wheat ACC; Rt, rat; Ch, chicken; Yt, yeast; Sy ACC, Synechococcus BC; An ACC, Anabaena BC and BCCP proteins; EC ACC, *E. coli* BC and BCCP; Hm PCCA, human propionyl CoA carboxylase; Rt PCCA, rat propionyl CoA carboxylase;, Yt PC, yeast pyruvate carboxylase.

FIG. 6A, FIG. 6B, and FIG. 6C shows the nucleotide sequence (SEQ ID NO:108) of a portion of the wheat cDNA corresponding to ACC. The amino acid sequence (SEQ ID NO:109) deduced from the nucleotide sequence is also shown. The underlined sequences correspond to the primer sites shown in FIG. 5. A unique sequence was found for the BC domain, suggesting that a single mRNA was the template for the final amplified products. For the sequence between the BC and BCCP domains, three different variants were found among four products sequenced, suggesting that three different gene transcripts were among the amplified products. This is not unexpected because wheat is hexaploid, i.e. it has three pairs of each chromosome.

FIG. 8 shows the nucleotide sequence (SEQ ID NO:110) of a PCR product corresponding to a portion of the fabE gene encoding about 75% of the biotin carboxyl carrier protein from the cyanobacterium Anabaena, along with the amino acid sequence (SEQ ID NO:111) deduced from the coding sequence. The underlined sequences correspond to the primer sites shown in FIG. 7.

DETAILED DESCRIPTION OF THE INVENTION

I. Definitions

Figure 4:
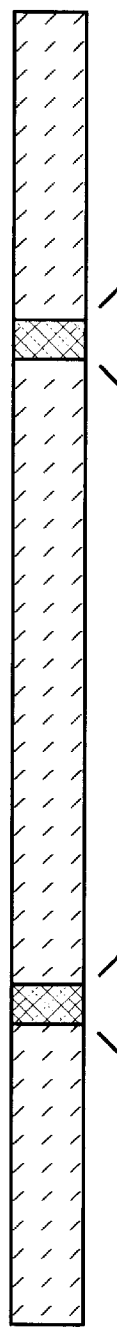
FIG. 4 shows the conserved amino acid sequences used to design primers for the PCR to amplify the BC domain of ACC from wheat. The sequences of the oligonucleotide primers (SEQ ID NOS:112 and 113) are also shown. In this and other figures showing primer sequences, A means adenine, C means cytosine, G means guanine, T means thymine, N means all four nucleotides, Y means T or C, R means A or G, K means G or T, M means A or C, W means A or T, and H means A, C or T.

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g. plant protoplast or explant).

Structural gene: A gene that is expressed to produce a polypeptide.

Transformation: A process of introducing an exogenous DNA sequence (e.g. a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g. somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

Certain polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides polynucleotides and polypeptides relating to a whole or a portion of acetyl-CoA carboxylase (ACC) of cyanobacteria and plants as well as processes using those polynucleotides and polypeptides.

II Polynucleotides

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 150,000 base pairs. Preferred lengths of particular polynucleotides are set hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

A. Cyanobacteria

In one embodiment, the present invention contemplates an isolated and purified polynucleotide of from about 1350 to about 40,000 base pairs that encodes a polypeptide having the ability to catalyze the carboxylation of a biotin carboxyl carrier protein of a cyanobacterium.

Preferably, a biotin carboxyl carrier protein (BCCP) is derived from a cyanobacterium such as Anabaena or Synechococcus. A preferred Anabaena is Anabaena 7120. A preferred Synechococcus is *Anacystis nidulans* R2 (Synechococcus sp. strain pcc7942). A biotin carboxyl carrier protein preferably includes the amino acid residue sequence shown in SEQ ID NO:111 or a functional equivalent thereof.

Figure 1A:
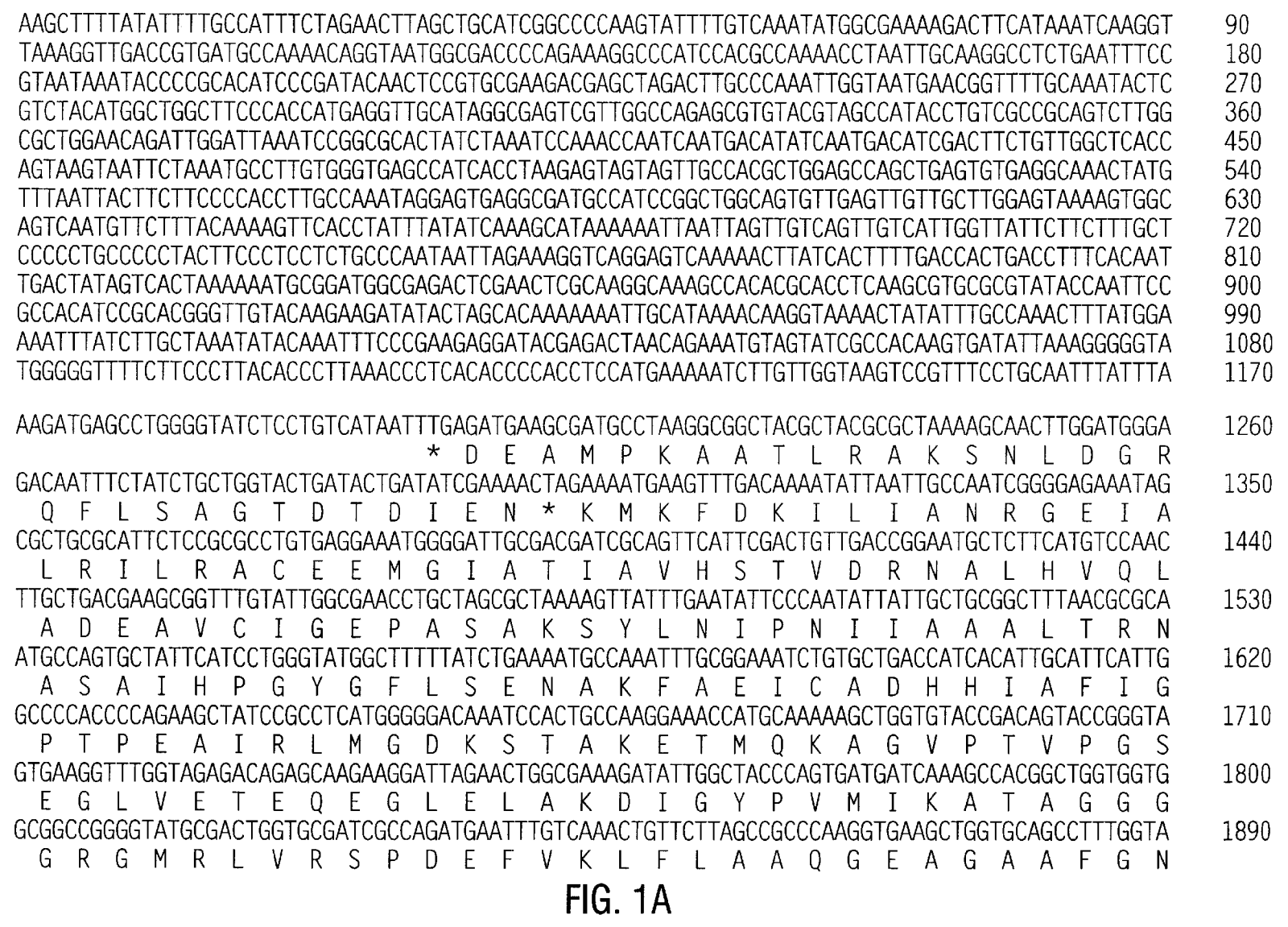

Preferably, a polypeptide is a biotin carboxylase enzyme of a cyanobacterium, which enzyme is a subunit of acetyl-CoA carboxylase and participates in the carboxylation of acetyl-CoA. In a preferred embodiment, a polypeptide encoded by such a polynucleotide has the amino acid residue sequence of FIGS. 1A and 1B or FIG. 2A and FIG. 2B, (SEQ ID NO:5 and SEQ ID NO:6) or a functional equivalent of those sequences.

A polynucleotide preferably includes the DNA sequence of SEQ ID NO:1 (FIG. 1A and FIG. 1B) or the DNA sequence of SEQ ID NO:1 (FIG. 1A and FIG. 1B) from about nucleotide position 1300 to about nucleotide position 2650.

The polynucleotide of SEQ ID NO:1 contains a gene that encodes the enzyme biotin carboxylase (BC) from the cyanobacterium Anabaena. This gene was cloned in the following way: total DNA from Anabaena was digested with various restriction enzymes, fractionated by gel electrophoresis, and blotted onto GeneScreen Plus (DuPont). The blot was hybridized at low stringency (1M NaCl, 57° C.) with a probe consisting of a SstII-PstI fragment containing about 90% of the coding region of the fabG gene from *E. coli*. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18.

Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1M NaCl, 65° C.), a cosmid library of Anabaena DNA inserts averaging 40 kb in size. Five were found among 1920 tested, all of which contained the same size HindIII and NheI fragments as those identified by the *E. coli* probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1A and FIG. 1B (SEQ ID NO:1 and SEQ ID NO:2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the *E. coli* fabG probe in digests of total Synechococcus DNA. Both fragments were subcloned from the cosmid into Bluescript KS and 2.4 kb, including the coding part of the fabG gene, were sequenced. The complete sequence of the coding region of the Synechococcus fabG gene is shown in FIG. 2A and FIG. 2B (SEQ ID NO:5 and SEQ ID NO:6).

In another aspect, the present invention provides an isolated and purified polynucleotide of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred polynucleotide that encodes that polypeptide includes the DNA sequence of SEQ ID NO:110 (FIG. 8).

B. Plants

Another polynucleotide contemplated by the present invention encodes a plant polypeptide having the ability to catalyze the carboxylation of acetyl-CoA. Such a plant polypeptide is preferably a monocotyledonous or a dicotyledonous plant acetyl-CoA carboxylase enzyme.

An exemplary and preferred monocotyledonous plant is wheat, rice, maize, barley, rye, oats or timothy grass. An exemplary and preferred dicotyledonous plant is soybean, rape, sunflower, tobacco, Arabidopsis, petunia, pea, Canola, bean, tomato, potato, lettuce, spinach, alfalfa, cotton or carrot.

A monocotyledonous plant polypeptide is preferably wheat ACC, which ACC includes the amino acid residue sequence of SEQ ID NO:109 (FIG. 6A, FIG. 6B and FIG. 6C) or a functional equivalent thereof. A preferred polynucleotide that encodes such a polypeptide includes the DNA sequence of SEQ ID NO:108 (FIG. 6A, FIG. 6B and FIG. 6C).

Amino acid sequences of biotin carboxylase (BC) from Anabaena and Synechococcus show great similarity with amino acid residue sequences from other ACC enzymes as well as with the amino acid residue sequences of other biotin-containing enzymes (See FIG. 3). Based on that homology, the nucleotide sequences shown in FIG. 3A, FIG. 3B, FIG. 3C, FIG. 3D, FIG. 3E, and FIG. 3F (SEQ ID NO:112 and SEQ ID NO;113) were chosen for the construction of primers for polymerase chain reaction amplification of a corresponding region of the gene for ACC from wheat. Those primers have the nucleotide sequences shown below:

```
Primer 1
5' TCGAATTCGTNATNATHAARGC 3'   (SEQ ID NO:112);

Primer 2
5' GCTCTAGAGKRTGYTCNACYTG 3'  (SEQ ID NO:113);
``` where N is A, C, G or T; H is A, C or T; R is A or G; Y is T or C and K is G or T. Primers 1 and 2 comprise a 14-nucleotide specific sequence based on a conserved amino acid sequence and an 8-nucleotide extension at the 5'-end of the primer to provide anchors for rounds of amplification after the first round and to provide convenient restriction sites for analysis and cloning.

cDNA amplification began with a preparation of total polyA-containing mRNA from eight day-old green plants (*Triticum aestivum* var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by heat and low molecular weight material was removed by filtration.

The PCR was initiated by the addition of polymerase at 95° C. Amplification was for 45 cycles, each 1 min at 95°, 1 min at 42–46° and 2 min at 72° C. Both the reactions using Anabaena DNA and the single-stranded wheat cDNA as template yielded about 440 base pair (bp) products. The wheat product was eluted from a gel and reamplified using the same primers. That product, also 440 bp, was cloned into the Invitrogen (San Diego, Calif.) vector pCR1000 using their A/T tail method, and sequenced.

In eukaryotic ACCs, a BCCP domain is located about 300 amino acids away from the end of the BC domain, on the C-terminal side. Therefore, it is possible to amplify the cDNA covering the interval between the BC and BCCP domains using primers from the C-terminal end of the BC domain and the conserved MKM region of the BCCP. The BC primer was based on the wheat cDNA sequence obtained as described above. Those primers, each with 6- or 8-base 5'-extensions, are shown below and in FIG. 5.

```
Primer 3
5' GCTCTAGAATACTATTTCCTG 3'   (SEQ ID NO:114)

Primer 4
5' TCGAATTCWNCATYTTCATNRC 3'  (SEQ ID NO:115)
```

N, R and Y are as defined above. W is A or T. The BC primer (Primer 3) was based on the wheat cDNA sequence obtained as described above. The MKM primer (primer 4) was first checked by determining whether it would amplify the fabE gene coding BCCP from Anabaena DNA. This PCR was primed at the other end by using a primer based on the N-terminal amino acid residue sequence as determined on protein purified from Anabaena extracts by affinity chromatography. Those primers are shown below and in FIG. 7.

```
Primer 5
5' GCTCTAGAYTTYAAYGARATHMG 3'  (SEQ ID NO:116)

Primer 4
5' TCGAATTCWNCATYTTCATNRC 3'   (SEQ ID NO:115)
```

H, N, R, T, Y and W are as defined above. M is A or C. This amplification (using the conditions described above) yielded the correct fragment of the Anabaena fabE gene, which was used to identify cosmids that contained the entire fabE gene and flanking DNA. An about 4 kb XbaI fragment containing the gene was cloned into the vector Bluescript KS for sequencing.

Primers 3 and 4 were then used to amplify the intervening sequence in wheat cDNA. Again, the product of the first PCR was eluted and reamplified by another round of PCR, then cloned into the Invitrogen vector pCRII.

The complete 1.1 kb of the amplified DNA was sequenced, shown in FIG. 6A, FIG. 6B, and FIG. 6C (SEQ ID NO:108), nucleotides 376–1473. The nucleotide sequence of the BC domain is also shown in FIG. 6 (SEQ ID NO:108), nucleotides 1–422. Three clones of the BC domain gave the sequence shown. Four clones of the 1.1-kb fragment differed at several positions, corresponding to three closely related sequences, all of which are indicated in the Figure. Most of the sequence differences are in the third codon position and are silent in terms of the amino acid sequence.

The amino acid sequence of the polypeptide predicted from the cDNA sequence for this entire fragment of wheat cDNA (1473 nucleotides) is compared with the amino acid sequences of other ACC enzymes and related enzymes from various sources in FIG. 3A, FIG. 3B, FIG. 3C, FIG. 3D, FIG. 3E, and FIG. 3F. The most significant identities are with the ACC of rat, chicken and yeast, as shown in the table below. Less extensive similarities are evident with the BC subunits of bacteria and the BC domains of other enzymes such as pyruvate carboxylase of yeast and propionyl CoA carboxylase of rat. The amino acid identities between wheat ACC and other biotin-dependent enzymes, within the BC domain (amino acid residues 312–630 in FIG. 3A, FIG. 3B, FIG. 3C, FIG. 3D, FIG. 3E, and FIG. 3F) are shown below in Table 1.

TABLE 1

|  | % identity with wheat ACC | % identity with rat ACC |
|---|---|---|
| rat ACC | 58 | (100) |
| chicken ACC | 57 | |
| yeast ACC | 56 | |
| Synechococcus ACC | 32 | |
| Anabaena ACC | 30 | |
| E. coli ACC | 33 | |
| rat propionyl CoA carboxylase | 32 | 31 |
| yeast pyruvate carboxylase | 31 | |

C. Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected ACC gene sequence, e.g., a sequence such as that shown in FIG. 1A and FIG. 1B, FIG. 2A and FIG. 2B, FIG. 6A, FIG. 6B, and FIG. 6C, or FIG. 8 (SEQ ID NO:110 and SEQ ID NO:111). The ability of such nucleic acid probes to specifically hybridize to an ACC gene sequence lend them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of an ACC gene from a cyanobacterium or a plant using PCR technology. Segments of ACC genes from other organisms can also be amplified by PCR using such primers.

To provide certain of the advantages in accordance with the present invention, a preferred nucleic acid sequence employed for hybridization studies or assays includes sequences that are complementary to at least a 10 to 30 or so long nucleotide stretch of an ACC sequence, such as that shown in FIGS. 1, 2, 6 or 8 (SEQ ID NO:110 and SEQ ID NO:111). A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an ACC coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

D. Expression Vector

The present invention contemplates an expression vector comprising a polynucleotide of the present invention. Thus, in one embodiment an expression vector is an isolated and purified DNA molecule comprising a promoter operatively linked to an coding region that encodes a polypeptide having the ability to catalyze the carboxylation of a biotin carboxyl carrier protein of a cyanobacterium, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Where an expression vector of the present invention is to be used to transform a cyanobacterium, a promoter is selected that has the ability to drive and regulate expression in cyanobacteria. Promoters that function in bacteria are well known in the art. An exemplary and preferred promoter for the cyanobacterium Anabaena is the glnA gene promoter. An exemplary and preferred promoter for the cyanobacterium Synechococcus is the psbAI gene promoter. Alternatively, the cyanobacterial fabG gene promoters themselves can be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chua et al., *Science*, 244:174–181 (1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue specific or developmentally specific promoters affecting dicots or monocots.

Where the promoter is a near-constitutive promoter such as CaMV 35S, increases in polypeptide expression are found in a variety of transformed plant tissues (e.g. callus, leaf, seed and root). Alternatively, the effects of transformation can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See. e.g., Vodkin et al., *Cell*, 34:1023 (1983) and Lindstrom et al., *Developmental Genetics*, 11:160 (1990).

An expression vector containing a coding region that encodes a polypeptide of interest is engineered to be under control of the Lectin promoter and that vector is introduced into plants using, for example, a protoplast transformation method. Dhir et al., *Plant Cell Reports*, 10:97 (1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al. *Proc. Natl. Acad. Sci. U.S.A.*, 87:4144–48 (1990)), corn alcohol dehydrogenase 1 (Vogel et al., *J. Cell Biochem.*, (supplement 13D, 312) (1989)), corn zein 19KD gene (storage protein) (Boston et al., *Plant Physiol.*, 83:742–46), corn light harvesting complex (Simpson, *Science*, 233:34 (1986), corn heat shock protein (O'Dell et al., *Nature*, 313:810–12 (1985), pea small subunit RuBP Carboxylase (Poulsen et al., *Mol. Gen. Genet.*, 205:193–200 (1986); Cashmore et al., *Gen. Eng. of Plants*, Plenum Press, New York, 29–38 (1983), Ti plasmid mannopine synthase (Langridge et al., *Proc. Natl. Acad. Sci. USA*, 86:3219–3223 (1989), Ti plasmid nopaline synthase (Langridge et al., *Proc. Natl. Acad. Sci. USA*, 86:3219–3223 (1989), petunia chalcone isomerase (Van Tunen et al., *EMBO J.*, 7:1257 (1988), bean glycine rich protein 1 (Keller et al., *EMBO J.*, 8:1309–14 (1989), CaMV 35s transcript (O'Dell et al., *Nature*, 313:810–12 (1985) and Potato patatin (Wenzler et al., *Plant Mol. Biol.*, 12:41–50 (1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other plant integrating vector systems are known to function in plants including pCaMVCN transfer control vector described by Fromm et al., *Proc. Natl. Acad. Sci. USA*, 82:5824 (1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to catalyze the carboxylation of a biotin carboxyl carrier protein of a cyanobacterium is preferably a biotin carboxylase enzyme of a cyanobacterium, which enzyme is a subunit of acetyl-CoA carboxylase and participates in the carboxylation of acetyl-CoA. In a preferred embodiment, such a polypeptide has the amino acid residue sequence of FIG. 1 or FIG. 2, or a functional equivalent of those sequences. In accordance with such an embodiment, a coding region comprises the entire DNA sequence of SEQ ID NO:1 (FIG. 1) or the DNA sequence of SEQ ID NO:1 (FIG. 1A and FIG. 1B) from about nucleotide position 1300 to about nucleotide position 2650 or the DNA sequence of SEQ ID NO:5 (FIG. 2A and FIG. 2B).

In another embodiment, an expression vector comprises a coding region of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred such coding region includes the DNA sequence of SEQ ID NO:110 (FIG. 8).

In still yet another embodiment, an expression vector comprises a coding region that encodes a plant polypeptide having the ability to catalyze the carboxylation of acetyl-CoA. Such a plant polypeptide is preferably a monocotyledonous or a dicotyledonous plant acetyl-CoA carboxylase enzyme.

A preferred monocotyledonous plant polypeptide encoded by such a coding region is preferably wheat ACC, which ACC includes the amino acid residue sequence of SEQ ID NO:109 (FIG. 6A, FIG. 6B, and FIG. 6C) or a functional equivalent thereof. A preferred coding region includes the DNA sequence of SEQ ID NO:108 (FIG. 6A, FIG. 6B, and FIG. 6C).

III. Polypeptide

The present invention contemplates a polypeptide that defines a whole or a portion of an ACC of a cyanobacterium or a plant. In one embodiment, thus, the present invention provides an isolated polypeptide having the ability to catalyze the carboxylation of a biotin carboxyl carrier protein of a cyanobacterium such as Anabaena or Synechococcus. Preferably, a biotin carboxyl carrier protein includes the amino acid sequence of SEQ ID NO:111 and the polypeptide has FIG. 1A and FIG. 1B or FIG. 2A and FIG. 2B (SEQ ID NO:5 and SEQ ID NO:6).

The present invention also contemplates an isolated and purified biotin carboxyl carrier protein of a cyanobacterium such as Anabaena, which protein includes the amino acid residue sequence of SEQ ID NO:111.

In another embodiment, the present invention contemplates an isolated and purified plant polypeptide having a molecular weight of about 220 KD, dimers of which have the ability to catalyze the carboxylation of acetyl-CoA. Such a polypeptide preferably includes the amino acid residue sequence of SEQ ID NO:109.

Modification and changes may be made in the structure of polypeptides of the present invention and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like or even counterveiling properties (e.g., antagonistic v. agonistic).

In making such changes, the hydropathic index of amino acids may be considered. The importance of the hydropathic amino acid index in conferring interactive biologic function on a protein is generally understood in the art (Kyte & Doolittle, J. Mol. Biol., 157:105–132, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteinelcystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been asssigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The present invention thus contemplates functional equivalents of the polypeptides set forth above. A polypeptide of the present invention is prepared by standard techniques well known to those skilled in the art. Such techniques include, but are not limited to, isolation and purification from tissues known to contain that polypeptide and expression from cloned DNA using transformed cells.

IV. Transformed or Transgenic Cells or Plants

A cyanobacterium, a plant cell or a plant transformed with an expression vector of the present invention is also contemplated. A transgenic cyanobacterium, plant cell or plant derived from such a transformed or transgenic cell is also contemplated.

Means for transforming cyanobacteria are well known in the art. Typically, means of transformation are similar to those well known means used to transform other bacteria such as *E. coli*. Synechococcus can be transformed simply by incubation of log-phase cells with DNA. (Golden, et al., 1987)

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes. In addition, Agrobacteria containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. USA*, 84:5345 (1987). Therefore, commercially important cereal grains such as rice, corn, and wheat must usually be transformed using alternative methods. However, as mentioned above, the transformation of asparagus using Agrobacterium can also be achieved. See, for example, Bytebier, et al., *Proc. Natl. Acad. Sci. USA*, 84:5345 (1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet.*, 204:204 (1986); Callis et al., *Genes and Development*, 1:1183 (1987); and Marcotte et al., *Nature*, 335:454 (1988).

Application of these systems to different plant strains depends upon the ability to regenerate that particular plant strain from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant strains that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized. (Vasil, 1992)

Using that latter technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stable transgenic tobacco plants as described by Gordon-Kamm, W. J. et al., *The Plant Cell*, 2:603–618 (1990); Klein, T. M. et al., *Plant Physiol.*, 91:440–444 (1989); Klein, T. M. et al., *Proc. Natl. Acad. Sci. USA*, 85:8502–8505 (1988); and Tomes, D. T. et al., *Plant Mol. Biol.*, 14:261–268 (1990). Transformation of tissue explants eliminates the need for passage through a protoplast stage and thus speeds the production of transgenic plants.

Thus, the amount of a gene coding for a polypeptide of interest (i.e., a polypeptide having carboxylation activity) can be increased in monocotyledonous plants such as corn by transforming those plants using particle bombardment methods. Maddock et al., *Third International Congress of Plant Molecular Biology, Abstract* 372 (1991). By way of example, an expression vector containing an coding region for a dicotyledonous ACC and an appropriate selectable marker is transformed into a suspension of embryonic maize (corn) cells using a particle gun to deliver the DNA coated on microprojectiles. Transgenic plants are regenerated from transformed embryonic calli that express ACC. Particle bombardment has been used to successfully transform wheat (Vasil et al., 1992).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo 1986*, Butterworth, Stoneham, Mass., pp. 27–54 (1986).

The development or regeneration of plants from either single plant protoplasts or various explants is well known in the art. See, for example, *Methods for Plant Molecular Bilogy*, A. Weissbach and H. Weissbach, eds., Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described by Horsch et al., *Science*, 227:1229–1231 (1985). In this procedure, transformants are cultured in the presence of a selection agent and in a medium that induces the regeneration of shoots in the plant strain being transformed as described by Fraley et al., *Proc. Natl. Acad. Sci. U.S.A.*, 80:4803 (1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants.

A transgenic plant of the present invention containing a desired polypeptide is cultivated using methods well known to one skilled in the art. Any of the transgenic plants of the present invention can be cultivated to isolate the desired ACC or fatty acids which are the products of the series of reactions of which that catalyzed by ACC is the first.

A transgenic plant of this invention thus has an increased amount of an coding region (e.g. gene) that encodes a polypeptide of interest. A preferred transgenic plant is an independent segregant and can transmit that gene and its activity to its progeny. A more preferred transgenic plant is homozygous for that gene, and transmits that gene to all of its offspring on sexual mating.

Seed from a transgenic plant is grown in the field or greenhouse, and resulting sexually mature transgenic plants are self-pollinated to generate true breeding plants. The progeny from these plants become true breeding lines that are evaluated for, by way of example, herbicide resistance, preferably in the field, under a range of environmental conditions.

The commercial value of a transgenic plant with increased herbicide resistance or with altered fatty acid production is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, herbicide resistance is preferably bred into a large number of parental lines so that many hybrid combinations can be produced.

V. Process of Increasing Herbicide Resistance

Herbicides such as aryloxyphenoxypropionates and cyclohexanediones inhibit the growth of monocotyledonous weeds by interfering with fatty acid biosynthesis of herbicide sensitive plants. ACC is the target enzyme for those herbicides. Dicotyledonous plants, other eukaryotic organisms and prokaryotic organisms are resistant to those compounds.

Thus, the resistance of sensitive monocotyledonous plants to herbicides can be increased by providing those plants with ACC that is not sensitive to herbicide inhibition. The present invention therefore provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a herbicide resistant polypeptide, a dicotyledonous plant polypeptide such as an acetyl-CoA carboxylase enzyme from soybean, rape, sunflower, tobacco, Arabidopsis, petunia, Canola, pea, bean, tomato, potato, lettuce, spinach, alfalfa, cotton or carrot, or functional equivalent thereof. A promoter and a transcription-terminating region are preferably the same as set forth above.

Transformed monocotyledonous plants can be identified using herbicide resistance. A process for identifying a transformed monocotyledonous plant cell comprises the steps of:

(a) transforming the monocotyledonous plant cell with a DNA molecule that encodes a dicotyledonous acetyl-CoA carboxylase enzyme; and (b) determining the resistance of the plant cell to a herbicide and thereby the identification of the transformed monocotyledonous plant cell.

Means for transforming a monocotyledonous plant cell are the same as set forth above.

The resistance of a transformed plant cell to a herbicide is preferably determined by exposing such a cell to an effective herbicidal dose of a preselected herbicide and maintaining that cell for a period of time and under culture conditions sufficient for the herbicide to inhibit ACC, alter fatty acid biosynthesis or retard growth. The effects of the herbicide can be studied by measuring plant cell ACC activity, fatty acid synthesis or growth.

An effective herbicidal dose of a given herbicide is that amount of the herbicide that retards growth or kills plant cells not containing herbicide-resistant ACC or that amount of a herbicide known to inhibit plant growth. Means for determining an effective herbicidal dose of a given herbicide are well known in the art. Preferably, a herbicide used in such a process is an aryloxyphenoxypropionate or cyclohexanedione herbicide.

VI. Process of Altering ACC Activity

Acetyl-CoA carboxyase catalyzes the carboxylation of acetyl-CoA. Thus, the carboxylation of acetyl-CoA in a cyanobacterium or a plant can be altered by, for example, increasing an ACC gene copy number or changing the composition (e.g., nucleotide sequence) of an ACC gene. Changes in ACC gene composition can alter gene expression at either the transcriptional or translational level. Alternatively, changes in gene composition can alter ACC function (e.g., activity, binding) by changing primary, secondary or tertiary structure of the enzyme. By way of example, certain changes in ACC structure are associated with changes in the resistance of that altered ACC to herbicides. The copy number of such a gene can be increased by transforming a cyanobacterium or a plant cell with an appropriate expression vector comprising a DNA molecule that encodes ACC.

In one embodiment, therefore, the present invention contemplates a process of altering the carboxylation of acetyl-CoA in a cell comprising transforming the cell with a DNA molecule comprising a promoter operatively linked to a coding region that encodes a polypeptide having the ability to catalyze the carboxylation of acetyl-CoA, which coding region is operatively linked to a transcription-terminating region, whereby the promoter is capable of driving the transcription of the coding region in the cyanobacterium.

In a preferred embodiment, a cell is a cyanobacterium or a plant cell, a polypeptide is a cyanobacterial ACC or a plant ACC. Exemplary and preferred expression vectors for use in such a process are the same as set forth above.

Where a cyanobacterium is transformed with a plant ACC DNA molecule, that cyanobacterium can be used to identify herbicide resistant mutations in the gene encoding ACC. In accordance with such a use, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed or transfected cyanobacteria;

(b) inactivating cyanobacterial acetyl-CoA carboxylase;

(c) exposing the transformed cyanobacteria to an effective herbicidal amount of a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

Means for transforming cyanobacteria as well as expression vectors used for such transformation are preferably the same as set forth above. In a preferred embodiment, cyanobacteria are transformed or transfected with an expression vector comprising an coding region that encodes wheat ACC.

Cyanobacteria resistant to the herbicide are identified. Identifying comprises growing or culturing transformed cells in the presence of the herbicide and recovering those cells that survive herbicide exposure.

Transformed, herbicide-resistant cells are then grown in culture, collected and total DNA extracted using standard techniques. ACC DNA is isolated, amplified if needed and then characterized by comparing that DNA with DNA from ACC known to be inhibited by that herbicide.

VII. Process for Determining Herbicide Resistance Inheritibility

In yet another aspect, the present invention provides a process for determining the inheritance of plant resistance to herbicides of the aryloxyphenocypropionate or cyclohexanedione class. That process comprises the steps of:

(a) measuring resistance to herbicides of the aryloxyphenocypropionate or cyclohexanedione class in a parental plant line and in progeny of the parental plant line to;

(b) purifying DNA from the parental plant line and the progeny;

(c) digesting the DNA with restriction enzymes to form DNA fragments;

(d) fractionating the fragments on a gel;

(e) transferring the fragments to a filter support;

(f) annealing the fragments with a labelled RFLP probe consisting of a DNA molecule that encodes acetyl-CoA carboxylase or a portion thereof;

(g) detecting the presence of complexes between the fragments and the RFLP probe; and (h) correlating the herbicide resistance of step (a) with the complexes of step (g) and thereby the inheritance of herbicide resistance.

In a preferred embodiment, the herbicide resistant variant of acetyl-CoA carboxylase is a dicotyledonous plant acetyl-CoA carboxylase enzyme or a portion thereof. In another preferred embodiment, the herbicide resistant variant of acetyl-CoA carboxylase is a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

The inheritability of phenotypic traits such as herbicide resistance can be determined using RFLP analysis. Restriction fragment length polymorphisms (RFLPs) are due to sequence differences detectable by lengths of DNA fragments generated by digestion with restriction enzymes and typically revealed by agarose gel electrophoresis. There are large numbers of restriction endonucleases available, characterized by their recognition sequences and source.

Restriction fragment length polymorphism analyses are conducted, for example, by Native Plants Incorporated (NPI). This service is available to the public on a contractual basis. For this analysis, the genetic marker profile of the parental inbred lines is determined. If parental lines are essentially homozygous at all relevant loci (i.e., they should have only one allele at each locus), the diploid genetic marker profile of the hybrid offspring of the inbred parents should be the sum of those parents, e.g., if one parent had the allele A at a particular locus, and the other parent had B, the hybrid AB is by inference.

Probes capable of hybridizing to specific DNA segments under appropriate conditions are prepared using standard techniques well known to those skilled in the art. The probes are labelled with radioactive isotopes or fluorescent dyes for ease of detection. After restriction fragments are separated by size, they are identified by hybridization to the probe. Hybridization with a unique cloned sequence permits the identification of a specific chromosomal region (locus). Because all alleles at a locus are detectable, RFLP's are co-dominant alleles, thereby satisfying a criteria for a genetic marker. They differ from some other types of markers, e.g., from isozymes, in that they reflect the primary DNA sequence, they are not products of transcription or translation. Furthermore, different RFLP profiles result from different arrays of restriction endonucleases.

The foregoing examples illustrate particular embodiments of the present invention. It will be readily apparent to a skilled artisan that changes, modification and alterations can be made to those embodiments without departing from the true scope or spirit of the invention.

EXAMPLE 1

Isolation of Cyanobacterial ACC Polynucleotides

The polynucleotide of SEQ ID NO:1 contains a gene that encodes the enzyme biotin carboxylase (BC) enzyme from the cyanobacterium Anabaena 7120. This gene was cloned from a total DNA extract of Anabaena that was digested with various restriction enzymes, fractionated by gel electrophoresis, and blotted onto GeneScreen Plus (DuPont).

The blot was hybridized at low stringency (1M NaCl, 57° C.) with a probe consisting of a SstII-PstI fragment containing about 90% of the coding region of the fabG gene from *E. coli*. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18. Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1M NaCl, 65° C.), a cosmid library of Anabaena DNA inserts averaging 40 kb in size. Five were found among 1920 tested, all of which contained the same size HindIII and NheI fragments as those identified by the *E. coli* probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1A and FIG. 1B (SEQ ID NO:5 and SEQ ID NO:2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the *E. coli* fabG probe in digests of total Synechococcus DNA. Both fragments were subcloned from the cosmid into Bluescript KS and 2.4 kb, including the coding part of the fabG gene, were sequenced. The complete sequence of the coding region of the Anacystis fabG gene is shown in FIG. 2A and FIG. 2B (SEQ ID NO:5 and SEQ ID NO:6).

EXAMPLE 2

Plant ACC

Figure 5:
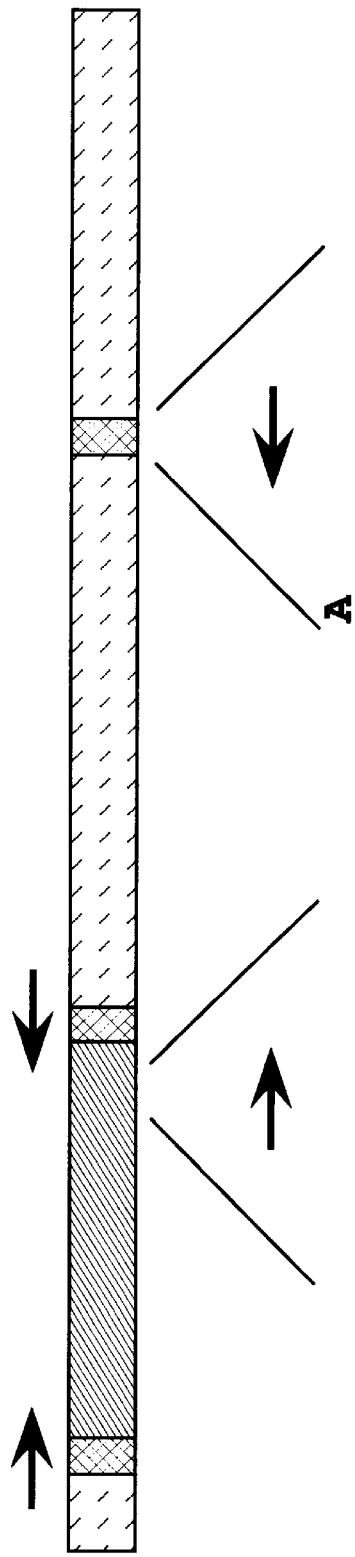
FIG. 5 shows the sequences of the oligonucleotides (SEQ ID NOS:114 and 115) used as primers for the PCR used to amplify the region of wheat ACC cDNA between the BC and BCCP domains.

The amino acid sequences of the fabG genes encoding BC from Anabaena and Synechococcus are aligned with sequences of ACC and other biotin-containing enzymes from several sources in FIG. 3A, FIG. 3B, FIG. 3C, FIG. 3D, FIG. 3E, and FIG. 3F. This comparison allows the designation of several areas of significant conservation among all the proteins, indicated by stars in the Figure. Based on this alignment, the sequences shown in FIG. 4 were chosen for the construction of primers for the polymerase chain reaction, in order to amplify the corresponding region of the gene for ACC from wheat. The primers used for this amplification are shown in FIG. 4. Each consists of a 14-nucleotide specific sequence based on the amino acid sequence and an 8-nucleotide extension at the 5'-end of the primer to provide anchors for rounds of amplification after the first round and to provide convenient restriction sites for future analysis and cloning.

cDNA amplification began with a preparation of total polyA-containing mRNA from eight day-old green plants (*Triticum aestivum* var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by incubation at 90° C. and low molecular weight material was removed by filtration through centricon 100. All components of the PCR. (from the Cetus/Perkin-Elmer kit) together with the two primers shown in FIG. 4, except the Taq DNA polymerase, were incubated for 3–5 min at 95° C. The PCR was initiated by the addition of polymerase. Conditions were established and optimized using Anabaena DNA as template, in order to provide the best yield and lowest level of non-specific products for amplification of the target BC gene from Anabaena DNA. Amplification was for 45 cycles, each 1 min at 95°, 1 min at 42–46° and 2 min at 72° C. Both the reactions using Anabaena DNA and the single-stranded wheat cDNA as template yielded about 440-bp products. The wheat product was eluted from a gel and reamplified using the same primers. That product, also 440 bp, was cloned into the Invitrogen vector pCR1000 using their A/T tail method, and sequenced. The nucleotide sequence is shown in FIG. 5.

In eukaryotic ACCs, the BCCP domain is located about 300 amino acids away from the end of the BC domain, on the C-terminal side. Therefore, it is possible to amplify the cDNA covering that interval using primers from the C-terminal end of the BC domain and the conserved MKM region of the BCCP. The BC primer was based on the wheat cDNA sequence obtained as described above. These primers, each with 6- or 8-base 5'-extensions, are shown in FIG. 6B.

Figure 7:
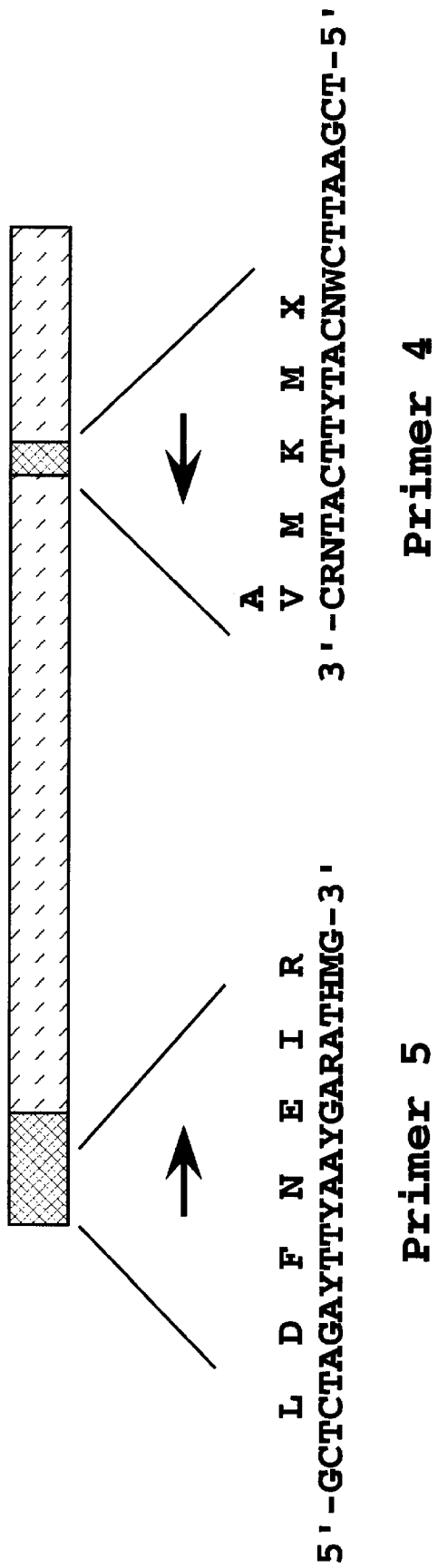
FIG. 7 shows the sequences (SEQ ID NOS:115 and 116) of the oligonucleotides used as primers to amplify most of the fabE gene encoding the biotin carboxyl carrier protein from DNA of Anabaena.

The MKM primer was first checked by determining whether it would amplify the fabE gene encoding BCCP from Anabaena DNA. This PCR was primed at the other end by using a primer based on the N-terminal amino acid sequence, determined on protein purified from Anabaena extracts by affinity chromatography, shown in FIG. 6A. This amplification (using the conditions described above)worked, yielding the correct fragment of the Anabaena fabE gene, whose complete sequence is shown in FIG. 7.

The PCR-amplified fragment of the Anabaena fabE gene was used to identify cosmids (three detected in a library of 1920) that contain the entire fabE gene and flanking DNA. A 4-kb XbaI fragment containing the gene was cloned into the vector Bluescript KS for sequencing. The two primers shown in FIG. 6A, FIG. 6B, and FIG. 6C were then used to amplify the intervening sequence in wheat cDNA. Again, the product of the first PCR was eluted and reamplified by another round of PCR, then cloned into the Invitrogen vector pCRII. The complete 1.1 kb of the amplified DNA was sequenced, also shown in FIG. 5. Applicants respectfully submit that the foregoing amendments do not introduce any new material into the application. The amendment was necessitated by the formal drawings requirement causing several sequences in the figures to be printed on separate pages in order to meet the size and margin requirements.

The foregoing examples illustrate particular embodiments of the present invention. One of ordinary skill in the art will readily appreciate that changes, modifications and alterations to those embodiments can be made without departing from the true scope or spirit of the invention.

References

The references listed below and all references cited herein are incorporated herein by reference to the extent that they supplement, explain, provide a background for, or teach methodology, techniques, and/or compositions employed herein.

1. J. R. Knowles. 1989. The mechanism of biotin-dependent enzymes. Annu. Rev. Biochem. 58: 195–221.
2. Alix, J.-H. 1989. A rapid procedure for cloning genes from I libraries by complementation of E. coli defective mutants: application to the fabE region of the E. coli chromosome. DNA 8: 779–789.
3. Muramatsu, S., and T. Mizuno. 1989. Nucleotide sequence of the fabE gene and flanking regions containing a bent DNA sequence of Escherichia coli Nucleic Acids Res. 17: 3982.
4. Li, S., and J. E. Cronan. 1992. The gene encoding the biotin carboxylase subunit of Escherichia coli acetyl-CoA carboxylase. J. Biol. Chem. 267: 855.
5. Lopez-Casillas, F., D. H. Bai, X. Luo, I. S. Kong, M. A. Hermodson, and K. H. Kim. 1988. Structure of the coding sequence and primary amino acid sequence of rat Acetyl-coenzyme A carboxylase. Proc. Natl. Acad. Sci. USA 85: 5784–5788.
6. Takai, T., C. Yokoyama, K. Wada, and T. Tanabe. 1988. Primary structure of chicken liver acetyl-coenzyme A carboxylase deduced from cDNA sequence. J. Biol. Chem.: 2651–2657.
    6a. W. A. Feel, S. S. Chirala and S. J. Wakil 1992. Cloning of the yeast FAS3 gene and primary structure of yeast acetyl-CoA carboxylase. Proc Natl Acad, Sci USA 89: 4534–4538.
7. J. L. Harwood. 1988. Fatty acid metabolism. Ann. Rev. Physiol. Plant Mol. Biol. 39: 101–138.
8. Egin-Buhler, B., and J. Ebel. 1983. Improved purification and further characterization of ACC from culture cells of parsley. Eur. J. Biochem. 133: 335–339.
9. Wurtele, E. S. and Nikolau, B. J. 1990. Arch. Biochem. Biophys. 278: 179–186.
10. Slabas, A. R. and Hellyer, A. 1985. Plant Sci. 39: 177–182.
11. Samols, D., C. G. Thornton, V. L. Murtif, G. K. Kumar, F. C. Haase, and H. G. Wood. 1988. Evolutionary conservation among biotin enzymes. J. Biol. Chem. 263: 6461–6464.
12. H. K. Lichtenthaler. 1990. Mode of action of herbicides affecting acetyl-CoA carboxylase and fatty acid biosynthesis. Z. Naturforsch. 45c: 521–528.
13. I. Pecker, D. Chamovitz, H. Linden, G. Sandmann and J. Hirschberg. 1992. A single polypeptide catalyzing the conversion of phytoene to z-carotene is transcriptionally regulated during tomato fruit ripening. Proc Natl Acad Sci USA 89: 4962–4666.
14. G. K. Lamppa, G. Morelli and N-H Chua (1985). Structure and developmental regulation of a wheat gene encoding the major chlorophyll a/b-binding polypeptide. Mol. Cell Biol. 5: 1370–1378.
15. H. Haymerle, J. Herz, G. M. Bressan, R. Frank and K. K. Stanley (1986). Efficient construction of cDNA libraries in plasmid expression vectors using an adaptor strategy. Nucl. Acids Res. 14: 8615–8629.
16. V. Vasil, A. M. Castillo, M. E. Fromm and I. K. Vasil (1992). Herbicide-resistant fertile transgenic wheat plants obtained by microprojectile bombardment of regenerable embryogenic callus. Biotechnology 10: 667–674.
17. S. S. Golden, T. Brusslen and R. Haselkom (1987), Genetic Engineering of the Cyanobacterial Chromosome. Methods Enzymology 153: 215–231.

What is claimed is:

1. An isolated nucleic acid segment comprising the nucleic acid sequence of SEQ ID NO:110, or the complement thereof, or a sequence which hybridizes to the sequence of SEQ ID NO:110 under conditions of high stringency that include a NaCl concentration of about 0.02M–0.15M at temperatures of about 50° C. to about 70° C.

2. The nucleic acid segment of claim 1, further defined as an RNA segment.

3. The nucleic acid of claim 1, further defined as encoding a protein comprising the amino acid sequence of SEQ ID NO:111.

4. The nucleic acid segment of claim 1, further defined as encoding a protein or peptide that comprises at least a fifteen amino acid contiguous sequence from SEQ ID NO:111.

5. A nucleic acid segment that encodes a peptide of from about 15 to about 145 amino acids in length, wherein said peptide comprises at least a fifteen-amino acid contiguous sequence from SEQ ID NO:111.

6. The nucleic acid segment of claim 5, further defined as encoding a peptide of from 15 to about 100 amino acids in length.

7. The nucleic acid segment of claim 6, further defined as encoding a peptide of from 15 to about 50 amino acids in length.

8. The nucleic acid segment of claim 1 or 5, further comprising a vector.

9. The nucleic acid segment of claim 1, or 5, wherein said nucleic acid segment is operatively linked to a promoter, said promoter expressing said nucleic acid segment.

10. A host cell comprising the nucleic acid segment of claim 1 or 3.

11. The host cell of claim 10, further defined as a plant cell or a bacterial cell.

12. The host cell of claim 11, wherein said bacterial cell is an *E. coli* cell, and said plant cell is a monocotyledonous or a dicotyledonous plant cell.

13. The host cell of claim 12, wherein said monocotyledonous plant cell is a wheat, rice, maize, barley, rye, oats, or timothy grass cell.

14. The host cell of claim 12, wherein said dicotyledonous plant cell is a soybean, rape, sunflower, tobacco, Arabidopsis, petunia, canola, pea, bean, tomato, potato, lettuce, spinach, carrot, alfalfa, or cotton cell.

15. The host cell of claim 10 wherein the cell is Anabaena spp., or a Synechococcus spp. cell.

16. An isolated nucleic acid segment comprising:
   (a) a nucleic acid segment comprising a sequence region that consists of at least 20 contiguous nucleotides that have the same sequence as, or are complementary to, 20 contiguous nucleotides of SEQ ID NO:110, or
   (b) a nucleic acid segment of from about 20 to about 4,000 nucleotides in length that hybridizes to the nucleic acid segment of SEQ ID NO:110; or the complement thereof, under conditions of high stringency stringency that include a NaCl concentration of about 0.02M–0.15M at temperatures of about 50° C. to about 70° C.

17. The nucleic acid segment of claim 16, further defined as comprising a sequence region that consists of at least about 20 contiguous nucleotides that have the same sequence as, or are complementary to, at least about 20 contiguous nucleotides of SEQ ID NO:110.

18. The nucleic acid segment of claim 16, further defined as comprising a nucleic acid segment of from about 20 to about 4,000 nucleotides in length that hybridizes to the nucleic acid segment of SEQ ID NO:110, or the complement thereof, under conditions of high stringency that include a NaCl concentration of about 0.02M–0.15M at temperatures of about 50° C. to about 70° C.

19. A method of using a DNA segment that encodes a cyanobacterial biotin carboxyl carrier protein or peptide, comprising the steps of:
   (a) preparing a vector in which a cyanobacterial biotin carboxyl carrier protein or peptide-encoding DNA segment of claim 1 is positioned under the control of a promoter;
   (b) introducing said vector into a host cell;
   (c) culturing said host cell under conditions effective to allow expression of the encoded biotin carboxyl carrier protein or peptide; and
   (d) collecting said biotin carboxyl carrier protein or peptide.

* * * * *

UNITED STATES PATENT AND TRADEMARK OFFICE
CERTIFICATE OF CORRECTION

PATENT NO.    :   5,972,644

DATED         :   October 26, 1999

INVENTOR(S)   :   Robert Haselkorn, Piotr Gornicki

It is certified that error appears in the above-identified patent and that said Letters Patent is hereby corrected as shown below:

In claim 9, column 101, line 49, after "1" please delete --,-- therefor.

Signed and Sealed this

Twenty-third Day of May, 2000

*Attest:*

Q. TODD DICKINSON

*Attesting Officer*     *Director of Patents and Trademarks*